US008389208B2

(12) United States Patent
Sutton et al.

(10) Patent No.: US 8,389,208 B2
(45) Date of Patent: Mar. 5, 2013

(54) BIOLOGICAL INDICATOR

(75) Inventors: J. Mark Sutton, Salisbury (GB); Neil David Hammond Raven, Salisbury (GB)

(73) Assignee: Health Protection Agency (GB)

( * ) Notice: Subject to any disclaimer, the term of this patent is extended or adjusted under 35 U.S.C. 154(b) by 1243 days.

(21) Appl. No.: 10/599,098

(22) PCT Filed: Mar. 22, 2005

(86) PCT No.: PCT/GB2005/001056

§ 371 (c)(1), (2), (4) Date: Aug. 27, 2009

(87) PCT Pub. No.: WO2005/093085
PCT Pub. Date: Oct. 6, 2005

(65) Prior Publication Data
US 2009/0317794 A1 Dec. 24, 2009

(30) Foreign Application Priority Data

Mar. 22, 2004 (GB) .................................. 0406427.5

(51) Int. Cl.
*C12Q 1/70* (2006.01)

(52) U.S. Cl. ........................................... 435/5; 436/518

(58) Field of Classification Search ........................ None
See application file for complete search history.

(56) References Cited

U.S. PATENT DOCUMENTS

| | | | | |
|---|---|---|---|---|
| 4,584,272 | A | 4/1986 | Imahori et al. | |
| 4,608,335 | A | 8/1986 | Fossati | |
| 5,418,167 | A | 5/1995 | Matner et al. | |
| 6,913,896 | B1 * | 7/2005 | Raven et al. | 435/7.92 |
| 2003/0162243 | A1 | 8/2003 | Foltz et al. | |
| 2011/0177539 | A1 * | 7/2011 | Sutton et al. | 435/8 |

FOREIGN PATENT DOCUMENTS

| | | |
|---|---|---|
| AU | 2005225596 | 10/2009 |
| CA | 2558359 | 3/2012 |
| CN | 200580009130.0 | 5/2008 |
| CN | 200580009130.0 | 2/2009 |
| CN | 200580009130.0 | 6/2009 |
| CN | 200580009130.0 | 4/2010 |
| CN | 200580009130.0 | 11/2010 |
| CN | 201110045849.7 | 3/2012 |
| EP | 05718095.2 | 3/2008 |
| EP | 05718095.2 | 7/2009 |
| EP | 05718095.2 | 7/2010 |
| GB | 2005/001056 | 6/2006 |
| IN | 3014/KOLNP/2006 | 7/2010 |
| JP | 57065184 | 4/1982 |
| JP | 2007-504461 | 2/2011 |
| WO | WO 00/46357 | 8/2000 |
| WO | WO 02/33056 | 4/2002 |
| WO | WO 02/053723 | 7/2002 |
| WO | WO 2004/003226 | 1/2004 |

OTHER PUBLICATIONS

Kath et al. Identification, Cloning, and Expression of the Gene for Adenylate Kinase from the Thermoacidophilic Archaebacterium Sulfolobus acidocaldarius. Archives of Biochemistry and Biophysics. vol. 307, Issue 2, Dec. 1993, pp. 405-410.*
Aflalo, C., et al., "Continuous monitoring of adenosine 5'-triphosphate in the microenvironment of immobilized enzymes by firefly luciferase", Biochemistry, vol. 26, pp. 3913-3920, (1987).
Burdette, D.S., et al., "Effect of thermal and chemical denaturants on thermoanaerobacter ethanolicus secondary-alcohol dehydrogenase stability and activity", Enzyme and Microbial Technology, vol. 27, pp. 11-18, (2000).
Crameri, A., et al., "Improved green fluorescent protein by molecular evolution using DNA shuffling", Nature Biotechnology, vol. 14, pp. 315-319, (1996).
Criswell, A.R., et al., "Structures of thermophilic and mesophilic adenylate kinases from the genus *Methanococcus*", J. Mol. Biology, vol. 330, pp. 1087-1099, (2003).
Daniel, R.M., et al., "A correlation between protein thermostability and resistance to proteolysis", Biochem J., vol. 207, pp. 641-644, (1982).
Gupta, M.N., "Thermostabilization of proteins", Biotechnology and Applied Biochemistry, vol. 14, pp. 1-11, (1991).
Hayashi, T., et al., "Analyses of biochemical substances by the use of immobilized pyruvate kinase and lactate dehydrogenase", Rept. National Food Research Institute, No. 40, pp. 102-105, (1982).
International Preliminary Report on Patentability for PCT application No. PCT/GB2005/001056 dated Jun. 13, 2006.
International Search Report and Written Opinion for PCT application No. PCT/GB2005/001056 dated Sep. 12, 2005.
Kawashima, K., "A method to prepare bead-shaped immobilized enzyme", Enz. Engineer, vol. 4, pp. 159-160, (1978).
Klibanov, A.M., "Stabilization of enzymes against thermal inactivation", Advances in Applied Microbiology, vol. 29, pp. 1-28, (1983).
Klibanov, A.M., "Enzyme stabilization by immobilization", Analytical Biochemistry, vol. 93, pp. 1-25, (1979).
Liao, H.H., "Thermostable mutants of kanamycin nucleotidyltransferase are also more stable to proteinase K, urea, detergents, and water-miscible organic solvents", Enzyme Microb Technology, vol. 15, No. 4, pp. 286-292, (1993).
Mannens, G., et al., "Purification and immobilization of acetate kinase from desulfovibrio vulgaris", Biotechnology Letters, vol. 10, No. 8, pp. 563-568, (1988).
Melik-Nubarov, N.S., "Protein stabilization via hydrophilization: stabilization of α-chymotrypsin by reductive alkylation with glyoxylic acid", Biotechnology Letters, vol. 9, No. 10, pp. 725-730, (1987).
Michel, P.E., et al., "A transient enzymatic inhibition as an efficient tool for the discriminating bioluminescent analysis of three adenylic nucleotides with a fiberoptic sensor based on a compartmentalized tri-enzymatic sensing layer", Analytica Chimica Acta, vol. 360, pp. 89-99, (1998).
Nakajima, H., et al., "Continuous ATP regeneration process with stable acetate kinase", Journal of Applied Biochemistry, vol. 6, pp. 19-28, (1984).
Rees, D.C., et al., "Some thermodynamic implications for the thermostability of proteins", Protein Science, vol. 10, pp. 1187-1194, (2001).
Scandurra, R., et al., "Protein thermostability in extremophiles", Biochimie, vol. 80, pp. 933-941, (1998).

(Continued)

*Primary Examiner* — Michelle S Horning
(74) *Attorney, Agent, or Firm* — Evan Law Group LLC

(57) ABSTRACT

A kinase is used in a biological indicator for validation of treatment processes designed to reduce the amount or activity of a biological agent in a sample. The indication can be used for validation of sterilization treatment. The formation of ATP from a substrate comprising ADP is measured via the liciferin/luciferate system in a luminameter. Thermostable adenylate kinase from *sulfolobus acidocaldarius* is especially suitable for the validation of procedures to inactivate transmissible spongiform encephalopathy agents.

23 Claims, 9 Drawing Sheets

OTHER PUBLICATIONS

Slegers, G., et al., "Co-immobilized pyruvate kinase and lactate dehydrogenase as recycling system for ATP", Enzyme Microb. Technology, vol. 8, pp. 153-156, (1986).

Stemmer, W.P.C., "Rapid evolution of a protein in vitro by DNA shuffling", Nature, vol. 370, pp. 389-391, (1994).

Taylor, D.M., "Resistance of transmissible spongiform encephalopathy agents to decontamination", Contrib. Microbiol., vol. 7, pp. 58-67, (2001).

Taylor, D.M., "Principles and practice of disinfection, preservation and sterilization", Chapter 7, Transmissible degenerative encephalopathies: inactivation of the unconventional causal agents, Blackwell Scientific Publications, Oxford, (Russel, A.D., Hugo, W.B., and Ayliffe, G.A.J., eds), pp. 222-236, (1999).

Taylor, D.M., et al., "Thermostability of mouse-passaged BSE and scrapie is independent of host PrP genotype: implications for the nature of the causal agents", Journal of General Virology, vol. 83, pp. 3199-3204, (2002).

GB Search Report for GB application No. GB0406427.5 dated May 26, 2004.

GB Search Report for GB application No. GB0406427.5 dated Oct. 15, 2004.

Vartanian, J-P., et al., "Hypermutagenic PCR involving all four transitions and a sizeable proportion of transversions", Nucleic Acids Research, vol. 24, No. 14, pp. 2627-2631, (1996).

Vonrhein, C., et al., "The structure of a trimeric archaeal adenylate kinase", Journal of Molecular Biology, vol. 282, pp. 167-179, (1998).

Zdanovsky, et al., "Simple and efficient method for heterologous expression of clostridial proteins", Applied and Environmental Microbiology, vol. 66, No. 8, pp. 3166-3173, (2000).

Wang, X. et al., "Research progression in improving biological activity and stability of proteins", Biotechniques, vol. 16, issue 6, pp. 84-86, (2004) with Statement of Relevancy (translation of Chinese Office Action citing reference).

* cited by examiner

A.

B.

A.

B.

ID

SEQUENCE LISTING

<160> NUMBER OF SEQ ID NOS: 30

<210> SEQ ID NO 1
<211> LENGTH: 195
<212> TYPE: PRT
<213> ORGANISM: Sulfolobus solfataricus

<400> SEQUENCE: 1

Met Lys Ile Gly Ile Val Thr Gly Ile Pro Gly Val Gly Lys Thr Thr
1               5                   10                  15

Val Leu Ser Phe Ala Asp Lys Ile Leu Thr Glu Lys Gly Ile Ser His
            20                  25                  30

Lys Ile Val Asn Tyr Gly Asp Tyr Met Leu Asn Thr Ala Leu Lys Glu
                35                  40                  45

Gly Tyr Val Lys Ser Arg Asp Glu Ile Arg Lys Leu Gln Ile Glu Lys
        50                  55                  60

Gln Arg Glu Leu Gln Ala Leu Ala Ala Arg Ile Val Glu Asp Leu
65                  70                  75                  80

Ser Leu Leu Gly Asp Glu Gly Ile Gly Leu Ile Asp Thr His Ala Val
                85                  90                  95

Ile Arg Thr Pro Ala Gly Tyr Leu Pro Gly Leu Pro Arg His Val Ile
                100                 105                 110

Glu Val Leu Ser Pro Lys Val Ile Phe Leu Leu Glu Ala Asp Pro Lys
                115                 120                 125

Ile Ile Leu Glu Arg Gln Lys Arg Asp Ser Ser Arg Ala Arg Thr Asp
                130                 135                 140

Tyr Ser Asp Thr Ala Val Ile Asn Glu Val Ile Gln Phe Ala Arg Tyr
145                 150                 155                 160

Ser Ala Met Ala Ser Ala Val Leu Val Gly Ala Ser Val Lys Val Val
                165                 170                 175

Val Asn Gln Glu Gly Asp Pro Ser Ile Ala Ala Ser Glu Ile Ile Asn
                180                 185                 190

Ser Leu Met
        195

<210> SEQ ID NO 2
<211> LENGTH: 194
<212> TYPE: PRT
<213> ORGANISM: Sulfolobus acidocaldarius

<400> SEQUENCE: 2

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
                20                  25                  30

Lys Ile Ile Asn Tyr Gly Asp Phe Met Leu Ala Thr Ala Leu Lys Leu
                35                  40                  45

Gly Tyr Ala Lys Asp Arg Asp Glu Met Arg Lys Leu Ser Val Glu Lys
        50                  55                  60

Gln Lys Lys Leu Gln Ile Asp Ala Ala Lys Gly Ile Ala Glu Glu Ala
65                  70                  75                  80

Arg Ala Gly Gly Glu Gly Tyr Leu Phe Ile Asp Thr His Ala Val Ile
                85                  90                  95

Arg Thr Pro Ser Gly Tyr Leu Pro Gly Leu Pro Ser Tyr Val Ile Thr
                100                 105                 110

Glu Ile Asn Pro Ser Val Ile Phe Leu Leu Glu Ala Asp Pro Lys Ile
                115                 120                 125

Ile Leu Ser Arg Gln Lys Arg Asp Thr Thr Arg Asn Arg Asn Asp Tyr
                130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
                180                 185                 190

Met Lys

```
<210> SEQ ID NO 3
<211> LENGTH: 197
<212> TYPE: PRT
<213> ORGANISM: Sulfolobus tokodaii

<400> SEQUENCE: 3

Met Ser Lys Met Lys Ile Gly Ile Val Thr Gly Ile Pro Gly Val Gly
1               5                   10                  15

Lys Thr Thr Val Leu Ser Lys Val Lys Glu Ile Leu Glu Glu Lys Lys
            20                  25                  30

Ile Asn Asn Lys Ile Val Asn Tyr Gly Asp Tyr Met Leu Met Thr Ala
        35                  40                  45

Met Lys Leu Gly Tyr Val Asn Asn Arg Asp Glu Met Arg Lys Leu Pro
    50                  55                  60

Val Glu Lys Gln Lys Gln Leu Gln Ile Glu Ala Ala Arg Gly Ile Ala
65                  70                  75                  80

Asn Glu Ala Lys Glu Gly Gly Asp Gly Leu Leu Phe Ile Asp Thr His
                85                  90                  95

Ala Val Ile Arg Thr Pro Ser Gly Tyr Leu Pro Gly Leu Pro Lys Tyr
            100                 105                 110

Val Ile Glu Glu Ile Asn Pro Arg Val Ile Phe Leu Leu Glu Ala Asp
        115                 120                 125

Pro Lys Val Ile Leu Asp Arg Gln Lys Arg Asp Thr Ser Arg Ser Arg
    130                 135                 140

Ser Asp Tyr Ser Asp Glu Arg Ile Ile Ser Glu Thr Ile Asn Phe Ala
145                 150                 155                 160

Arg Tyr Ala Ala Met Ala Ser Ala Val Leu Val Gly Ala Thr Val Lys
                165                 170                 175

Ile Val Ile Asn Val Gly Asp Pro Ala Val Ala Ala Asn Glu Ile
            180                 185                 190

Ile Asn Ser Met Leu
        195

<210> SEQ ID NO 4
<211> LENGTH: 196
<212> TYPE: PRT
<213> ORGANISM: Pyrococcus furiosus

<400> SEQUENCE: 4

Met Pro Phe Val Val Ile Ile Thr Gly Ile Pro Gly Val Gly Lys Ser
1               5                   10                  15

Thr Ile Thr Arg Leu Ala Leu Gln Arg Thr Lys Ala Lys Phe Arg Leu
            20                  25                  30

Ile Asn Phe Gly Asp Leu Met Phe Glu Glu Ala Val Lys Ala Gly Leu
        35                  40                  45

Val Lys His Arg Asp Glu Met Arg Lys Leu Pro Leu Lys Ile Gln Arg
    50                  55                  60

Glu Leu Gln Met Lys Ala Ala Lys Lys Ile Thr Glu Met Ala Lys Glu
65                  70                  75                  80

His Pro Ile Leu Val Asp Thr His Ala Thr Ile Lys Thr Pro His Gly
                85                  90                  95

Tyr Met Leu Gly Leu Pro Tyr Glu Val Val Lys Thr Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
    130                 135                 140
```

```
Gln Arg His Gln Asp Leu Asn Arg Ala Ala Ile Ala Tyr Ala Met
145                 150                 155                 160

His Ser Asn Ala Leu Ile Lys Ile Ile Glu Asn His Glu Asp Lys Gly
            165                 170                 175

Leu Glu Glu Ala Val Asn Glu Leu Val Lys Ile Leu Asp Leu Ala Val
        180                 185                 190

Asn Glu Tyr Ala
        195

<210> SEQ ID NO 5
<211> LENGTH: 196
<212> TYPE: PRT
<213> ORGANISM: Pyrococcus horikoshii

<400> SEQUENCE: 5

Met Pro Phe Val Val Ile Ile Thr Gly Ile Pro Gly Val Gly Lys Ser
1               5                   10                  15

Thr Ile Thr Lys Leu Ala Leu Gln Arg Thr Arg Ala Lys Phe Lys Leu
            20                  25                  30

Ile Asn Phe Gly Asp Leu Met Phe Glu Glu Ala Leu Lys Leu Lys Leu
        35                  40                  45

Val Lys His Arg Asp Glu Met Arg Lys Leu Pro Leu Glu Val Gln Arg
    50                  55                  60

Glu Leu Gln Met Asn Ala Ala Lys Lys Ile Ala Glu Met Ala Lys Asn
65                  70                  75                  80

Tyr Pro Ile Leu Leu Asp Thr His Ala Thr Ile Lys Thr Pro His Gly
                85                  90                  95

Tyr Leu Leu Gly Leu Pro Tyr Glu Val Ile Lys Ile Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
    130                 135                 140

Gln Arg His Gln Asp Leu Asn Arg Ala Ala Ala Ile Thr Tyr Ala Met
145                 150                 155                 160

His Ser Asn Ala Leu Ile Lys Ile Ile Glu Asn His Glu Asp Lys Gly
            165                 170                 175

Leu Glu Glu Ala Val Asn Glu Leu Val Lys Ile Leu Asp Leu Ala Val
        180                 185                 190

Lys Glu Tyr Ala
        195

<210> SEQ ID NO 6
<211> LENGTH: 196
<212> TYPE: PRT
<213> ORGANISM: Pyrococcus abyssi

<400> SEQUENCE: 6

Met Ser Phe Val Val Ile Ile Thr Gly Ile Pro Gly Val Gly Lys Ser
1               5                   10                  15

Thr Ile Thr Arg Leu Ala Leu Gln Arg Thr Lys Ala Lys Phe Lys Leu
            20                  25                  30

Ile Asn Phe Gly Asp Leu Met Phe Glu Glu Ala Val Lys Ala Gly Leu
        35                  40                  45

Val Asn His Arg Asp Glu Met Arg Lys Leu Pro Leu Glu Ile Gln Arg
    50                  55                  60
```

```
Asp Leu Gln Met Lys Val Ala Lys Ile Ser Glu Met Ala Arg Gln
 65                  70                  75                  80

Gln Pro Ile Leu Leu Asp Thr His Ala Thr Ile Lys Thr Pro His Gly
                 85                  90                  95

Tyr Leu Leu Gly Leu Pro Tyr Glu Val Ile Lys Thr Leu Asn Pro Asn
            100                 105                 110

Phe Ile Val Ile Ile Glu Ala Thr Pro Ser Glu Ile Leu Gly Arg Arg
            115                 120                 125

Leu Arg Asp Leu Lys Arg Asp Arg Asp Val Glu Thr Glu Glu Gln Ile
        130                 135                 140

Gln Arg His Gln Asp Leu Asn Arg Ala Ala Ile Ala Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Glu Ile Leu Asp Leu Ala Val
            180                 185                 190

Lys Glu Tyr Ala
        195

<210> SEQ ID NO 7
<211> LENGTH: 192
<212> TYPE: PRT
<213> ORGANISM: Methanococcus thermolithotrophicus

<400> SEQUENCE: 7

Met Lys Asn Lys Leu Val Val Thr Gly Val Pro Gly Val Gly Gly
  1               5                  10                  15

Thr Thr Ile Thr Gln Lys Ala Met Glu Lys Leu Ser Glu Glu Gly Ile
                 20                  25                  30

Asn Tyr Lys Met Val Asn Phe Gly Thr Val Met Phe Glu Val Ala Gln
             35                  40                  45

Glu Glu Asn Leu Val Glu Asp Arg Asp Gln Met Arg Lys Leu Asp Pro
         50                  55                  60

Asp Thr Gln Lys Arg Ile Gln Lys Leu Ala Gly Arg Lys Ile Ala Glu
 65                  70                  75                  80

Met Val Lys Glu Ser Pro Val Val Asp Thr His Ser Thr Ile Lys
                 85                  90                  95

Thr Pro Lys Gly Tyr Leu Pro Gly Leu Pro Val Trp Val Leu Asn Glu
            100                 105                 110

Leu Asn Pro Asp Ile Ile Val Val Glu Thr Ser Gly Asp Glu Ile
            115                 120                 125

Leu Ile Arg Arg Leu Asn Asp Glu Thr Arg Asn Arg Asp Leu Glu Thr
        130                 135                 140

Thr Ala Gly Ile Glu Glu His Gln Ile Met Asn Arg Ala Ala Ala Met
145                 150                 155                 160

Thr Tyr Gly Val Leu Thr Gly Ala Thr Val Lys Ile Ile Gln Asn Lys
                165                 170                 175

Asn Asn Leu Leu Asp Tyr Ala Val Glu Glu Leu Ile Ser Val Leu Arg
            180                 185                 190

<210> SEQ ID NO 8
<211> LENGTH: 192
<212> TYPE: PRT
<213> ORGANISM: Methanococcus voltae

<400> SEQUENCE: 8

Met Lys Asn Lys Val Val Val Val Thr Gly Val Pro Gly Val Gly Ser
```

```
  1               5                  10                 15
Thr Thr Ser Ser Gln Leu Ala Met Asp Asn Leu Arg Lys Glu Gly Val
                20                 25                 30

Asn Tyr Lys Met Val Ser Phe Gly Ser Val Met Phe Glu Val Ala Lys
            35                 40                 45

Glu Glu Asn Leu Val Ser Asp Arg Asp Gln Met Arg Lys Met Asp Pro
        50                 55                 60

Glu Thr Gln Lys Arg Ile Gln Lys Met Ala Gly Arg Lys Ile Ala Glu
65                  70                 75                 80

Met Ala Lys Glu Ser Pro Val Ala Val Asp Thr His Ser Thr Val Ser
                85                 90                 95

Thr Pro Lys Gly Tyr Leu Pro Gly Leu Pro Ser Trp Val Leu Asn Glu
            100                105                110

Leu Asn Pro Asp Leu Ile Ile Val Glu Thr Thr Gly Asp Glu Ile
        115                120                125

Leu Met Arg Arg Met Ser Asp Glu Thr Arg Val Arg Asp Leu Asp Thr
        130                135                140

Ala Ser Thr Ile Glu Gln His Gln Phe Met Asn Arg Cys Ala Ala Met
145                 150                155                160

Ser Tyr Gly Val Leu Thr Gly Ala Thr Val Lys Ile Val Gln Asn Arg
                165                170                175

Asn Gly Leu Leu Asp Gln Ala Val Glu Glu Leu Thr Asn Val Leu Arg
            180                185                190
```

<210> SEQ ID NO 9
<211> LENGTH: 195
<212> TYPE: PRT
<213> ORGANISM: Methanococcus jannaschii

<400> SEQUENCE: 9

```
Met Met Met Met Lys Asn Lys Val Val Ile Val Gly Val Pro Gly
1               5                  10                 15

Val Gly Ser Thr Thr Val Thr Asn Lys Ala Ile Glu Glu Leu Lys Lys
                20                 25                 30

Glu Gly Ile Glu Tyr Lys Ile Val Asn Phe Gly Thr Val Met Phe Glu
            35                 40                 45

Ile Ala Lys Glu Glu Gly Leu Val Glu His Arg Asp Gln Leu Arg Lys
        50                 55                 60

Leu Pro Pro Glu Glu Gln Lys Arg Ile Gln Lys Leu Ala Gly Lys Lys
65                  70                 75                 80

Ile Ala Glu Met Ala Lys Glu Phe Asn Ile Val Val Asp Thr His Ser
                85                 90                 95

Thr Ile Lys Thr Pro Lys Gly Tyr Leu Pro Gly Leu Pro Ala Trp Val
            100                105                110

Leu Glu Glu Leu Asn Pro Asp Ile Ile Val Leu Val Glu Ala Glu Asn
        115                120                125

Asp Glu Ile Leu Met Arg Arg Leu Lys Asp Glu Thr Arg Gln Arg Asp
        130                135                140

Phe Glu Ser Thr Glu Asp Ile Gly Glu His Ile Phe Met Asn Arg Cys
145                 150                155                160

Ala Ala Met Thr Tyr Ala Val Leu Thr Gly Ala Thr Val Lys Ile Ile
                165                170                175

Lys Asn Arg Asp Phe Leu Leu Asp Lys Ala Val Gln Glu Leu Ile Glu
            180                185                190

Val Leu Lys
```

<210> SEQ ID NO 10
<211> LENGTH: 191
<212> TYPE: PRT
<213> ORGANISM: Methanopyrus kandleri

<400> SEQUENCE: 10

Met Gly Tyr Val Ile Val Ala Thr Gly Val Pro Gly Val Gly Ala Thr
1               5                   10                  15

Thr Val Thr Thr Glu Ala Val Lys Glu Leu Glu Gly Tyr Glu His Val
            20                  25                  30

Asn Tyr Gly Asp Val Met Leu Glu Ile Ala Lys Glu Gly Leu Val
        35                  40                  45

Glu His Arg Asp Glu Ile Arg Lys Leu Pro Ala Glu Lys Gln Arg Glu
    50                  55                  60

Ile Gln Arg Leu Ala Ala Arg Ile Ala Lys Met Ala Glu Glu Lys
65                  70                  75                  80

Glu Gly Ile Ile Val Asp Thr His Cys Thr Ile Lys Thr Pro Ala Gly
                85                  90                  95

Tyr Leu Pro Gly Leu Pro Ile Trp Val Leu Glu Leu Gln Pro Asp
            100                 105                 110

Val Ile Val Leu Ile Glu Ala Asp Pro Asp Glu Ile Met Met Arg Arg
        115                 120                 125

Val Lys Asp Ser Glu Glu Arg Gln Arg Asp Tyr Asp Arg Ala His Glu
    130                 135                 140

Ile Glu Glu His Gln Lys Met Asn Arg Met Ala Ala Met Ala Tyr Ala
145                 150                 155                 160

Ala Leu Thr Gly Ala Thr Val Lys Ile Ile Glu Asn His Asp Asp Arg
                165                 170                 175

Leu Glu Glu Ala Val Arg Glu Phe Val Glu Thr Val Arg Ser Leu
            180                 185                 190

<210> SEQ ID NO 11
<211> LENGTH: 192
<212> TYPE: PRT
<213> ORGANISM: Methanotorris igneus

<400> SEQUENCE: 11

Met Lys Asn Lys Val Val Val Thr Gly Val Pro Gly Val Gly Gly
1               5                   10                  15

Thr Thr Leu Thr Gln Lys Thr Ile Glu Lys Leu Lys Glu Glu Gly Ile
            20                  25                  30

Glu Tyr Lys Met Val Asn Phe Gly Thr Val Met Phe Glu Val Ala Lys
        35                  40                  45

Glu Glu Gly Leu Val Glu Asp Arg Asp Gln Met Arg Lys Leu Asp Pro
    50                  55                  60

Asp Thr Gln Lys Arg Ile Gln Lys Leu Ala Gly Arg Lys Ile Ala Glu
65                  70                  75                  80

Met Ala Lys Glu Ser Asn Val Ile Val Asp Thr His Ser Thr Val Lys
                85                  90                  95

Thr Pro Lys Gly Tyr Leu Ala Gly Leu Pro Ile Trp Val Leu Glu Glu
            100                 105                 110

Leu Asn Pro Asp Ile Ile Val Ile Val Glu Thr Ser Ser Asp Glu Ile
        115                 120                 125

Leu Met Arg Arg Leu Gly Asp Ala Thr Arg Asn Arg Asp Ile Glu Leu
    130                 135                 140

```
Thr Ser Asp Ile Asp Glu His Gln Phe Met Asn Arg Cys Ala Ala Met
145                 150                 155                 160

Ala Tyr Gly Val Leu Thr Gly Ala Thr Val Lys Ile Ile Lys Asn Arg
            165                 170                 175

Asp Gly Leu Leu Asp Lys Ala Val Glu Glu Leu Ile Ser Val Leu Lys
        180                 185                 190

<210> SEQ ID NO 12
<211> LENGTH: 197
<212> TYPE: PRT
<213> ORGANISM: Pyrobaculum aerophilum

<400> SEQUENCE: 12

Met Lys Ile Val Ile Val Ala Leu Pro Gly Ser Gly Lys Thr Thr Ile
1               5                   10                  15

Leu Asn Phe Val Lys Gln Lys Leu Pro Asp Val Lys Ile Val Asn Tyr
            20                  25                  30

Gly Asp Val Met Leu Glu Ile Ala Lys Lys Arg Phe Gly Ile Gln His
        35                  40                  45

Arg Asp Glu Met Arg Lys Lys Ile Pro Val Asp Glu Tyr Arg Lys Val
50                  55                  60

Gln Glu Glu Ala Ala Glu Tyr Ile Ala Ser Leu Thr Gly Asp Val Ile
65                  70                  75                  80

Ile Asp Thr His Ala Ser Ile Lys Ile Gly Gly Tyr Tyr Pro Gly
                85                  90                  95

Leu Pro Asp Arg Ile Ile Ser Lys Leu Lys Pro Asp Val Ile Leu Leu
            100                 105                 110

Leu Glu Tyr Asp Pro Lys Val Ile Leu Glu Arg Arg Lys Lys Asp Pro
        115                 120                 125

Asp Arg Phe Arg Asp Leu Glu Ser Glu Glu Ile Glu Met His Gln
130                 135                 140

Gln Ala Asn Arg Tyr Tyr Ala Phe Ala Ala Ala Asn Ala Gly Glu Ser
145                 150                 155                 160

Thr Val His Val Leu Asn Phe Arg Gly Lys Pro Glu Ser Arg Pro Phe
            165                 170                 175

Glu His Ala Glu Val Ala Ala Glu Tyr Ile Val Asn Leu Ile Leu Arg
        180                 185                 190

Thr Arg Gln Lys Ser
        195

<210> SEQ ID NO 13
<211> LENGTH: 220
<212> TYPE: PRT
<213> ORGANISM: Thermotoga maritima

<400> SEQUENCE: 13

Met Met Ala Tyr Leu Val Phe Leu Gly Pro Pro Gly Ala Gly Lys Gly
1               5                   10                  15

Thr Tyr Ala Lys Arg Ile Gln Glu Lys Thr Gly Ile Pro His Ile Ser
            20                  25                  30

Thr Gly Asp Ile Phe Arg Asp Ile Val Lys Lys Glu Asn Asp Glu Leu
        35                  40                  45

Gly Lys Lys Ile Lys Glu Ile Met Glu Lys Gly Glu Leu Val Pro Asp
50                  55                  60

Glu Leu Val Asn Glu Val Val Arg Arg Leu Ser Gly Lys Asp Cys
65                  70                  75                  80
```

```
Glu Lys Gly Phe Ile Leu Asp Gly Tyr Pro Arg Thr Val Ala Gln Ala
                85                  90                  95

Glu Phe Leu Asp Ser Phe Leu Glu Ser Gln Asn Lys Gln Leu Thr Ala
                100                 105                 110

Ala Val Leu Phe Asp Val Pro Glu Asp Val Val Gln Arg Leu Thr
                115                 120                 125

Ser Arg Arg Ile Cys Pro Lys Cys Gly Arg Ile Tyr Asn Met Ile Ser
            130                 135                 140

Leu Pro Pro Lys Glu Asp Glu Leu Cys Asp Asp Cys Lys Val Lys Leu
145                 150                 155                 160

Val Gln Arg Asp Asp Lys Glu Glu Thr Val Arg His Arg Tyr Lys
                165                 170                 175

Val Tyr Leu Glu Lys Thr Gln Pro Val Ile Asp Tyr Tyr Gly Lys Lys
                180                 185                 190

Gly Ile Leu Lys Arg Val Asp Gly Thr Ile Gly Ile Asp Asn Val Val
                195                 200                 205

Ala Glu Val Leu Lys Ile Ile Gly Trp Ser Asp Lys
                210                 215                 220

<210> SEQ ID NO 14
<211> LENGTH: 204
<212> TYPE: PRT
<213> ORGANISM: Aeropyrum pernix

<400> SEQUENCE: 14

Met Lys Val Arg His Pro Phe Lys Val Val Val Thr Gly Val Pro
1               5                   10                  15

Gly Val Gly Lys Thr Thr Val Ile Lys Glu Leu Gln Gly Leu Ala Glu
                20                  25                  30

Lys Glu Gly Val Lys Leu His Ile Val Asn Phe Gly Ser Phe Met Leu
                35                  40                  45

Asp Thr Ala Val Lys Leu Gly Leu Val Glu Asp Arg Asp Lys Ile Arg
            50                  55                  60

Thr Leu Pro Leu Arg Arg Gln Leu Glu Leu Gln Arg Glu Ala Ala Lys
65                  70                  75                  80

Arg Ile Val Ala Glu Ala Ser Lys Ala Leu Gly Gly Asp Gly Val Leu
                85                  90                  95

Ile Ile Asp Thr His Ala Leu Val Lys Thr Val Ala Gly Tyr Trp Pro
                100                 105                 110

Gly Leu Pro Lys His Val Leu Asp Glu Leu Lys Pro Asp Met Ile Ala
                115                 120                 125

Val Val Glu Ala Ser Pro Glu Glu Val Ala Ala Arg Gln Ala Arg Asp
                130                 135                 140

Thr Thr Arg Tyr Arg Val Asp Ile Gly Gly Val Glu Gly Val Lys Arg
145                 150                 155                 160

Leu Met Glu Asn Ala Arg Ala Ala Ser Ile Ala Ser Ala Ile Gln Tyr
                165                 170                 175

Ala Ser Thr Val Ala Ile Val Glu Asn Arg Glu Gly Gly Ala Ala Lys
                180                 185                 190

Ala Ala Glu Glu Leu Leu Arg Leu Ile Lys Asn Leu
                195                 200

<210> SEQ ID NO 15
<211> LENGTH: 216
<212> TYPE: PRT
<213> ORGANISM: Archaeoglobus fulgidus
```

<400> SEQUENCE: 15

```
Met Asn Leu Ile Phe Leu Gly Pro Pro Ala Gly Lys Gly Thr Gln
1               5                   10                  15

Ala Lys Arg Val Ser Glu Lys Tyr Gly Ile Pro Gln Ile Ser Thr Gly
            20                  25                  30

Asp Met Leu Arg Glu Ala Val Ala Lys Gly Thr Glu Leu Gly Lys Lys
        35                  40                  45

Ala Lys Glu Tyr Met Asp Lys Gly Glu Leu Val Pro Asp Glu Val Val
    50                  55                  60

Ile Gly Ile Val Lys Glu Arg Leu Gln Gln Pro Asp Cys Glu Lys Gly
65                  70                  75                  80

Phe Ile Leu Asp Gly Phe Pro Arg Thr Leu Ala Gln Ala Glu Ala Leu
                85                  90                  95

Asp Glu Met Leu Lys Glu Leu Asn Lys Lys Ile Asp Ala Val Ile Asn
            100                 105                 110

Val Val Val Pro Glu Glu Val Val Lys Arg Ile Thr Tyr Arg Arg
        115                 120                 125

Thr Cys Arg Asn Cys Gly Ala Val Tyr His Leu Ile Tyr Ala Pro Pro
130                 135                 140

Lys Glu Asp Asn Lys Cys Asp Lys Cys Gly Gly Glu Leu Tyr Gln Arg
145                 150                 155                 160

Asp Asp Lys Glu Glu Thr Val Arg Glu Arg Tyr Arg Val Tyr Lys Gln
                165                 170                 175

Asn Thr Glu Pro Leu Ile Asp Tyr Tyr Arg Lys Lys Gly Ile Leu Tyr
            180                 185                 190

Asp Val Asp Gly Thr Lys Asp Ile Glu Gly Val Trp Lys Glu Ile Glu
        195                 200                 205

Ala Ile Leu Glu Lys Ile Lys Ser
    210                 215
```

<210> SEQ ID NO 16
<211> LENGTH: 220
<212> TYPE: PRT
<213> ORGANISM: Pyrococcus abyssi

<400> SEQUENCE: 16

```
Met Asn Ile Leu Ile Phe Gly Pro Pro Gly Ser Gly Lys Ser Thr Gln
1               5                   10                  15

Ala Arg Arg Ile Thr Glu Arg Tyr Gly Leu Thr Tyr Ile Ala Ser Gly
            20                  25                  30

Asp Ile Ile Arg Ala Glu Ile Lys Ala Arg Thr Pro Leu Gly Ile Glu
        35                  40                  45

Met Glu Arg Tyr Leu Ser Arg Gly Asp Leu Ile Pro Asp Thr Ile Val
    50                  55                  60

Asn Thr Leu Ile Ile Ser Lys Leu Arg Arg Val Arg Glu Asn Phe Ile
65                  70                  75                  80

Met Asp Gly Tyr Pro Arg Thr Pro Glu Gln Val Ile Thr Leu Glu Asn
                85                  90                  95

Tyr Leu Tyr Asp His Gly Ile Lys Leu Asp Val Ala Ile Asp Ile Tyr
            100                 105                 110

Ile Thr Lys Glu Glu Ser Val Arg Arg Ile Ser Gly Arg Arg Ile Cys
        115                 120                 125

Ser Lys Cys Gly Ala Val Tyr His Val Glu Phe Asn Pro Pro Lys Val
    130                 135                 140

Pro Gly Lys Cys Asp Ile Cys Gly Gly Glu Leu Ile Gln Arg Pro Asp
```

```
                    145                 150                 155                 160
Asp Arg Pro Glu Ile Val Glu Lys Arg Tyr Asp Ile Tyr Ser Lys Asn
                165                 170                 175

Met Glu Pro Ile Ile Lys Phe Tyr Gln Lys Gln Gly Ile Tyr Val Arg
            180                 185                 190

Ile Asp Gly His Gly Ser Ile Asp Glu Val Trp Glu Arg Ile Arg Pro
        195                 200                 205

Leu Leu Asp Tyr Ile Tyr Asn Gln Glu Asn Arg Arg
    210                 215                 220

<210> SEQ ID NO 17
<211> LENGTH: 196
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (61)..(61)
<223> OTHER INFORMATION: The amino acid "X" may be K or E.
<220> FEATURE:
<221> NAME/KEY: MISC_FEATURE
<222> LOCATION: (75)..(75)
<223> OTHER INFORMATION: The amino acid "X" may be T or A.
<220> FEATURE:
<221> NAME/KEY: MISC_FEATURE
<222> LOCATION: (98)..(98)
<223> OTHER INFORMATION: The amino acid "X" may be M or L.
<220> FEATURE:
<221> NAME/KEY: MISC_FEATURE
<222> LOCATION: (157)..(157)
<223> OTHER INFORMATION: The amino acid "X" may be A, or a small
      hydrophobic residue (e.g. I or L) or a large hydrophobic residue
      (e.g. F), that increases the thermal stability of the enzyme.

<400> SEQUENCE: 17

Met Pro Phe Val Val Ile Ile Thr Gly Ile Pro Gly Val Gly Lys Ser
1               5                   10                  15

Thr Ile Thr Arg Leu Ala Leu Gln Arg Thr Lys Ala Lys Phe Arg Leu
            20                  25                  30

Ile Asn Phe Gly Asp Leu Met Phe Glu Glu Ala Val Lys Ala Gly Leu
        35                  40                  45

Val Lys His Arg Asp Glu Met Arg Lys Leu Pro Leu Xaa Ile Gln Arg
    50                  55                  60

Glu Leu Gln Met Lys Ala Ala Lys Lys Ile Xaa Glu Met Ala Lys Glu
65                  70                  75                  80

His Pro Ile Leu Val Asp Thr His Ala Thr Ile Lys Thr Pro His Gly
                85                  90                  95

Tyr Xaa Leu Gly Leu Pro Tyr Glu Val Val Lys Thr Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
    130                 135                 140

Gln Arg His Gln Asp Leu Asn Arg Ala Ala Ile Xaa Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
            180                 185                 190

Asn Glu Tyr Ala
        195
```

```
<210> SEQ ID NO 18
<211> LENGTH: 196
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (47)..(47)
<223> OTHER INFORMATION: The amino acid "X" may be G, or may be any
      other residue that increases the thermal stability of the enzyme.
<220> FEATURE:
<221> NAME/KEY: MISC_FEATURE
<222> LOCATION: (157)..(157)
<223> OTHER INFORMATION: The amino acid "X" may be A, or a small
      hydrophobic residue (e.g. I or L) or a large hydrophobic residue
      (e.g. F), that increases the thermal stability of the enzyme.

<400> SEQUENCE: 18

Met Pro Phe Val Val Ile Ile Thr Gly Ile Pro Gly Val Gly Lys Ser
1               5                   10                  15

Thr Ile Thr Lys Leu Ala Leu Gln Arg Thr Arg Ala Lys Phe Lys Leu
            20                  25                  30

Ile Asn Phe Gly Asp Leu Met Phe Glu Glu Ala Leu Lys Leu Xaa Leu
        35                  40                  45

Val Lys His Arg Asp Glu Met Arg Lys Leu Pro Leu Glu Val Gln Arg
    50                  55                  60

Glu Leu Gln Met Asn Ala Ala Lys Lys Ile Ala Glu Met Ala Lys Asn
65                  70                  75                  80

Tyr Pro Ile Leu Leu Asp Thr His Ala Thr Ile Lys Thr Pro His Gly
                85                  90                  95

Tyr Leu Leu Gly Leu Pro Tyr Glu Val Ile Lys Ile Leu Asn Pro Asn
            100                 105                 110

Phe Ile Val Ile Ile Glu Ala Thr Pro Ser Glu Ile Leu Gly Arg Arg
        115                 120                 125

Leu Arg Asp Leu Lys Arg Asp Arg Asp Val Glu Thr Glu Glu Gln Ile
    130                 135                 140

Gln Arg His Gln Asp Leu Asn Arg Ala Ala Ala Ile Xaa Tyr Ala Met
145                 150                 155                 160

His Ser Asn Ala Leu Ile Lys Ile Ile Glu Asn His Glu Asp Lys Gly
                165                 170                 175

Leu Glu Glu Ala Val Asn Glu Leu Val Lys Ile Leu Asp Leu Ala Val
            180                 185                 190

Lys Glu Tyr Ala
        195

<210> SEQ ID NO 19
<211> LENGTH: 194
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (103)..(103)
<223> OTHER INFORMATION: The amino acid "X" may be A or M.

<400> SEQUENCE: 19

Met Lys Ile Gly Ile Val Thr Gly Ile Pro Gly Val Gly Lys Ser Thr
1               5                   10                  15

Val Leu Ala Lys Val Lys Glu Ile Leu Asp Asn Gln Gly Ile Asn Asn
            20                  25                  30
```

```
Lys Ile Ile Asn Tyr Gly Asp Phe Met Leu Ala Thr Ala Leu Lys Leu
            35                  40                  45

Gly Tyr Ala Lys Asp Arg Asp Glu Met Arg Lys Leu Ser Val Glu Lys
 50                  55                  60

Gln Lys Lys Leu Gln Ile Asp Ala Ala Lys Gly Ile Ala Glu Glu Ala
 65                  70                  75                  80

Arg Ala Gly Gly Glu Gly Tyr Leu Phe Ile Asp Thr His Ala Val Ile
                85                  90                  95

Arg Thr Pro Ser Gly Tyr Xaa Pro Gly Leu Pro Ser Tyr Val Ile Thr
                100                 105                 110

Glu Ile Asn Pro Ser Val Ile Phe Leu Leu Glu Ala Asp Pro Lys Ile
            115                 120                 125

Ile Leu Ser Arg Gln Lys Arg Asp Thr Thr Arg Asn Arg Asn Asp Tyr
130                 135                 140

Ser Asp Glu Ser Val Ile Leu Glu Thr Ile Asn Phe Ala Arg Tyr Ala
145                 150                 155                 160

Ala Thr Ala Ser Ala Val Leu Ala Gly Ser Thr Val Lys Val Ile Val
                165                 170                 175

Asn Val Glu Gly Asp Pro Ser Ile Ala Ala Asn Glu Ile Ile Arg Ser
                180                 185                 190

Met Lys

<210> SEQ ID NO 20
<211> LENGTH: 403
<212> TYPE: PRT
<213> ORGANISM: Thermotoga maritima

<400> SEQUENCE: 20

Met Arg Val Leu Val Ile Asn Ser Gly Ser Ser Ile Lys Tyr Gln
 1               5                  10                  15

Leu Ile Glu Met Glu Gly Glu Lys Val Leu Cys Lys Gly Ile Ala Glu
                 20                  25                  30

Arg Ile Gly Ile Glu Gly Ser Arg Leu Val His Arg Val Gly Asp Glu
                35                  40                  45

Lys His Val Ile Glu Arg Glu Leu Pro Asp His Glu Glu Ala Leu Lys
 50                  55                  60

Leu Ile Leu Asn Thr Leu Val Asp Glu Lys Leu Gly Val Ile Lys Asp
 65                  70                  75                  80

Leu Lys Glu Ile Asp Ala Val Gly His Arg Val Val His Gly Gly Glu
                85                  90                  95

Arg Phe Lys Glu Ser Val Leu Val Asp Glu Glu Val Leu Lys Ala Ile
                100                 105                 110

Glu Glu Val Ser Pro Leu Ala Pro Leu His Asn Pro Ala Asn Leu Met
            115                 120                 125

Gly Ile Lys Ala Ala Met Lys Leu Leu Pro Gly Val Pro Asn Val Ala
130                 135                 140

Val Phe Asp Thr Ala Phe His Gln Thr Ile Pro Gln Lys Ala Tyr Leu
145                 150                 155                 160

Tyr Ala Ile Pro Tyr Glu Tyr Tyr Glu Lys Tyr Lys Ile Arg Arg Tyr
                165                 170                 175

Gly Phe His Gly Thr Ser His Arg Tyr Val Ser Lys Arg Ala Ala Glu
                180                 185                 190

Ile Leu Gly Lys Lys Leu Glu Glu Leu Lys Ile Ile Thr Cys His Ile
                195                 200                 205
```

```
Gly Asn Gly Ala Ser Val Ala Ala Val Lys Tyr Gly Lys Cys Val Asp
            210                 215                 220

Thr Ser Met Gly Phe Thr Pro Leu Glu Gly Leu Val Met Gly Thr Arg
225                 230                 235                 240

Ser Gly Asp Leu Asp Pro Ala Ile Pro Phe Phe Ile Met Glu Lys Glu
                245                 250                 255

Gly Ile Ser Pro Gln Glu Met Tyr Asp Ile Leu Asn Lys Lys Ser Gly
                260                 265                 270

Val Tyr Gly Leu Ser Lys Gly Phe Ser Ser Asp Met Arg Asp Ile Glu
                275                 280                 285

Glu Ala Ala Leu Lys Gly Asp Glu Trp Cys Lys Leu Val Leu Glu Ile
290                 295                 300

Tyr Asp Tyr Arg Ile Ala Lys Tyr Ile Gly Ala Tyr Ala Ala Ala Met
305                 310                 315                 320

Asn Gly Val Asp Ala Ile Val Phe Thr Ala Gly Val Gly Glu Asn Ser
                325                 330                 335

Pro Ile Thr Arg Glu Asp Val Cys Ser Tyr Leu Glu Phe Leu Gly Val
                340                 345                 350

Lys Leu Asp Lys Gln Lys Asn Glu Glu Thr Ile Arg Gly Lys Glu Gly
                355                 360                 365

Ile Ile Ser Thr Pro Asp Ser Arg Val Lys Val Leu Val Pro Thr
370                 375                 380

Asn Glu Glu Leu Met Ile Ala Arg Asp Thr Lys Gly Ile Val Glu Lys
385                 390                 395                 400

Ile Gly Arg

<210> SEQ ID NO 21
<211> LENGTH: 478
<212> TYPE: PRT
<213> ORGANISM: Pyrococcus horikoshii

<400> SEQUENCE: 21

Met Arg Arg Met Lys Leu Pro Ser His Lys Thr Lys Ile Val Ala Thr
1               5                   10                  15

Ile Gly Pro Ala Thr Asn Ser Lys Lys Met Ile Lys Lys Leu Ile Glu
                20                  25                  30

Ala Gly Met Asn Val Ala Arg Ile Asn Phe Ser His Gly Thr Phe Glu
                35                  40                  45

Glu His Ala Lys Ile Ile Glu Met Val Arg Glu Gln Ser Gln Lys Leu
        50                  55                  60

Asp Arg Arg Val Ala Ile Leu Ala Asp Leu Pro Gly Leu Lys Ile Arg
65                  70                  75                  80

Val Gly Glu Ile Lys Gly Gly Tyr Val Glu Leu Glu Arg Gly Glu Lys
                85                  90                  95

Val Thr Leu Thr Thr Lys Asp Ile Glu Gly Asp Glu Thr Thr Ile Pro
                100                 105                 110

Val Glu Tyr Lys Asp Phe Pro Lys Leu Val Ser Lys Gly Asp Val Ile
                115                 120                 125

Tyr Leu Ser Asp Gly Tyr Ile Val Leu Arg Val Glu Asp Val Lys Glu
                130                 135                 140

Asn Glu Val Glu Ala Val Val Ile Ser Gly Gly Lys Leu Phe Ser Arg
145                 150                 155                 160

Lys Gly Ile Asn Ile Pro Lys Ala Tyr Leu Pro Val Glu Ala Ile Thr
                165                 170                 175

Pro Arg Asp Ile Glu Ile Met Lys Phe Ala Ile Glu His Gly Val Asp
```

```
                    180                 185                 190
Ala Ile Gly Leu Ser Phe Val Gly Asn Val Tyr Asp Val Leu Lys Ala
                195                 200                 205

Lys Ser Phe Leu Glu Arg Asn Gly Ala Gly Asp Thr Phe Val Ile Ala
            210                 215                 220

Lys Ile Glu Arg Pro Asp Ala Val Arg Asn Phe Asn Glu Ile Leu Asn
225                 230                 235                 240

Ala Ala Asp Gly Ile Met Ile Ala Arg Gly Asp Leu Gly Val Glu Met
                245                 250                 255

Pro Ile Glu Gln Leu Pro Ile Leu Gln Lys Arg Leu Ile Arg Lys Ala
            260                 265                 270

Asn Met Glu Gly Lys Pro Val Ile Thr Ala Thr Gln Met Leu Val Ser
275                 280                 285

Met Thr Met Glu Lys Val Pro Thr Arg Ala Glu Val Thr Asp Val Ala
        290                 295                 300

Asn Ala Ile Leu Asp Gly Thr Asp Ala Val Met Leu Ser Glu Glu Thr
305                 310                 315                 320

Ala Val Gly Lys Phe Pro Ile Glu Ala Val Glu Met Met Ala Arg Ile
                325                 330                 335

Ala Lys Val Thr Glu Glu Tyr Arg Glu Ser Phe Gly Ile Thr Arg Met
            340                 345                 350

Arg Glu Phe Leu Glu Gly Thr Lys Arg Gly Thr Ile Lys Glu Ala Ile
        355                 360                 365

Thr Arg Ser Ile Ile Asp Ala Ile Cys Thr Ile Gly Ile Lys Phe Ile
    370                 375                 380

Leu Thr Pro Thr Lys Thr Gly Arg Thr Ala Arg Leu Ile Ser Arg Phe
385                 390                 395                 400

Lys Pro Lys Gln Trp Ile Leu Ala Phe Ser Thr Arg Glu Lys Val Cys
                405                 410                 415

Asn Asn Leu Met Phe Ser Tyr Gly Val Tyr Pro Phe Cys Met Glu Glu
            420                 425                 430

Gly Phe Asn Glu Asn Asp Ile Val Arg Leu Ile Lys Gly Leu Gly Leu
        435                 440                 445

Val Gly Ser Asp Asp Ile Val Leu Met Thr Glu Gly Lys Pro Ile Glu
    450                 455                 460

Lys Thr Val Gly Thr Asn Ser Ile Lys Ile Phe Gln Ile Ala
465                 470                 475

<210> SEQ ID NO 22
<211> LENGTH: 452
<212> TYPE: PRT
<213> ORGANISM: Sulfolobus solfataricus

<400> SEQUENCE: 22

Met Arg Lys Thr Lys Ile Val Ala Thr Leu Gly Pro Ser Ser Glu Glu
1               5                   10                  15

Lys Val Lys Glu Leu Ala Glu Tyr Val Asp Val Phe Arg Ile Asn Phe
            20                  25                  30

Ala His Gly Asp Glu Thr Ser His Arg Lys Tyr Phe Asp Leu Ile Arg
        35                  40                  45

Thr Tyr Ala Pro Glu Ser Ile Ile Val Asp Leu Pro Gly Pro Lys
    50                  55                  60

Leu Arg Leu Gly Glu Leu Lys Glu Pro Ile Glu Val Lys Lys Gly Asp
65                  70                  75                  80

Lys Ile Val Phe Ser Gln Lys Asp Gly Ile Pro Val Asp Asp Glu Leu
```

```
            85                  90                  95
Phe Tyr Ser Ala Val Lys Glu Asn Ser Asp Ile Leu Ile Ala Asp Gly
            100                 105                 110

Thr Ile Arg Val Arg Val Lys Ser Lys Ala Lys Asp Arg Val Glu Gly
            115                 120                 125

Thr Val Ile Glu Gly Gly Ile Leu Leu Ser Arg Lys Gly Ile Asn Ile
            130                 135                 140

Pro Asn Val Asn Leu Lys Ser Gly Ile Thr Asp Asn Asp Leu Lys Leu
145                 150                 155                 160

Leu Lys Arg Ala Leu Asp Leu Gly Ala Asp Tyr Ile Gly Leu Ser Phe
                165                 170                 175

Val Ile Ser Glu Asn Asp Val Lys Lys Val Lys Glu Phe Val Gly Asp
                180                 185                 190

Glu Ala Trp Val Ile Ala Lys Ile Glu Lys Ser Glu Ala Leu Lys Asn
                195                 200                 205

Leu Thr Asn Ile Val Asn Glu Ser Asp Gly Ile Met Val Ala Arg Gly
            210                 215                 220

Asp Leu Gly Val Glu Thr Gly Leu Glu Asn Leu Pro Leu Ile Gln Arg
225                 230                 235                 240

Arg Ile Val Arg Thr Ser Arg Val Phe Gly Lys Pro Val Ile Leu Ala
                245                 250                 255

Thr Gln Val Leu Thr Ser Met Ile Asn Ser Pro Ile Pro Thr Arg Ala
                260                 265                 270

Glu Ile Ile Asp Ile Ser Asn Ser Ile Met Gln Gly Val Asp Ser Ile
            275                 280                 285

Met Leu Ser Asp Glu Thr Ala Ile Gly Asn Tyr Pro Val Glu Ser Val
            290                 295                 300

Arg Thr Leu His Asn Ile Ile Ser Asn Val Glu Lys Ser Val Lys His
305                 310                 315                 320

Arg Pro Ile Gly Pro Leu Asn Ser Glu Ser Asp Ala Ile Ala Leu Ala
                325                 330                 335

Ala Val Asn Ala Ser Lys Val Ser Lys Ala Asp Val Ile Val Val Tyr
                340                 345                 350

Ser Arg Ser Gly Asn Ser Ile Leu Arg Val Ser Arg Leu Arg Pro Glu
            355                 360                 365

Arg Asn Ile Ile Gly Val Ser Pro Asp Pro Arg Leu Ala Lys Lys Phe
            370                 375                 380

Lys Leu Cys Tyr Gly Val Ile Pro Ile Ser Ile Asn Lys Lys Met Gln
385                 390                 395                 400

Ser Ile Asp Glu Ile Ile Asp Val Ser Ala Lys Leu Met Gln Glu Lys
                405                 410                 415

Ile Lys Asp Leu Lys Phe Lys Lys Ile Val Ile Val Gly Gly Asp Pro
                420                 425                 430

Lys Gln Glu Ala Gly Lys Thr Asn Phe Val Ile Val Lys Thr Leu Glu
            435                 440                 445

Gln Gln Lys Lys
        450

<210> SEQ ID NO 23
<211> LENGTH: 466
<212> TYPE: PRT
<213> ORGANISM: Thermotoga maritima

<400> SEQUENCE: 23

Met Arg Ser Thr Lys Ile Val Cys Thr Val Gly Pro Arg Thr Asp Ser
```

-continued

```
1               5                   10                  15
Tyr Glu Met Ile Glu Lys Met Ile Asp Leu Gly Val Asn Val Phe Arg
                20                  25                  30

Ile Asn Thr Ser His Gly Asp Trp Asn Glu Gln Glu Gln Lys Ile Leu
                35                  40                  45

Lys Ile Lys Asp Leu Arg Glu Lys Lys Lys Pro Val Ala Ile Leu
    50                  55                  60

Ile Asp Leu Ala Gly Pro Lys Ile Arg Thr Gly Tyr Leu Glu Lys Glu
65                  70                  75                  80

Phe Val Glu Leu Lys Glu Gly Gln Ile Phe Thr Leu Thr Thr Lys Glu
                    85                  90                  95

Ile Leu Gly Asn Glu His Ile Val Ser Val Asn Leu Ser Ser Leu Pro
                100                 105                 110

Lys Asp Val Lys Lys Gly Asp Thr Ile Leu Leu Ser Asp Gly Glu Ile
            115                 120                 125

Val Leu Glu Val Ile Glu Thr Thr Asp Thr Glu Val Lys Thr Val Val
    130                 135                 140

Lys Val Gly Gly Lys Ile Thr His Arg Arg Gly Val Asn Val Pro Thr
145                 150                 155                 160

Ala Asp Leu Ser Val Glu Ser Ile Thr Asp Arg Asp Arg Glu Phe Ile
                165                 170                 175

Lys Leu Gly Thr Leu His Asp Val Glu Phe Phe Ala Leu Ser Phe Val
                180                 185                 190

Arg Lys Pro Glu Asp Val Leu Lys Ala Lys Glu Glu Ile Arg Lys His
            195                 200                 205

Gly Lys Glu Ile Pro Val Ile Ser Lys Ile Glu Thr Lys Lys Ala Leu
    210                 215                 220

Glu Arg Leu Glu Glu Ile Ile Lys Val Ser Asp Gly Ile Met Val Ala
225                 230                 235                 240

Arg Gly Asp Leu Gly Val Glu Ile Pro Ile Glu Glu Val Pro Ile Val
                245                 250                 255

Gln Lys Glu Ile Ile Lys Leu Ser Lys Tyr Tyr Ser Lys Pro Val Ile
            260                 265                 270

Val Ala Thr Gln Ile Leu Glu Ser Met Ile Glu Asn Pro Phe Pro Thr
    275                 280                 285

Arg Ala Glu Val Thr Asp Ile Ala Asn Ala Ile Phe Asp Gly Ala Asp
                290                 295                 300

Ala Leu Leu Leu Thr Ala Glu Thr Ala Val Gly Lys His Pro Leu Glu
305                 310                 315                 320

Ala Ile Lys Val Leu Ser Lys Val Ala Lys Glu Ala Glu Lys Lys Leu
                325                 330                 335

Glu Phe Phe Arg Thr Ile Glu Tyr Asp Thr Ser Asp Ile Ser Glu Ala
                340                 345                 350

Ile Ser His Ala Cys Trp Gln Leu Ser Glu Ser Leu Asn Ala Lys Leu
                355                 360                 365

Ile Ile Thr Pro Thr Ile Ser Gly Ser Thr Ala Val Arg Val Ser Lys
            370                 375                 380

Tyr Asn Val Ser Gln Pro Ile Val Ala Leu Thr Pro Glu Glu Lys Thr
385                 390                 395                 400

Tyr Tyr Arg Leu Ser Leu Val Arg Lys Val Ile Pro Val Leu Ala Glu
                405                 410                 415

Lys Cys Ser Gln Glu Leu Glu Phe Ile Glu Lys Gly Leu Lys Lys Val
            420                 425                 430
```

-continued

Glu Glu Met Gly Leu Ala Glu Lys Gly Asp Leu Val Val Leu Thr Ser
          435                 440                 445

Gly Val Pro Gly Lys Val Gly Thr Thr Asn Thr Ile Arg Val Leu Lys
    450                 455                 460

Val Asp
465

<210> SEQ ID NO 24
<211> LENGTH: 477
<212> TYPE: PRT
<213> ORGANISM: Pyrococcus furiosus

<400> SEQUENCE: 24

Met Arg Arg Val Lys Leu Pro Ser His Lys Thr Lys Ile Val Ala Thr
1               5                   10                  15

Ile Gly Pro Ala Thr Asn Ser Arg Lys Met Ile Lys Gln Leu Ile Lys
            20                  25                  30

Ala Gly Met Asn Val Ala Arg Ile Asn Phe Ser His Gly Ser Phe Glu
        35                  40                  45

Glu His Ala Arg Val Ile Glu Ile Ile Arg Glu Glu Ala Gln Lys Leu
    50                  55                  60

Asp Arg Arg Val Ala Ile Leu Ala Asp Leu Pro Gly Leu Lys Ile Arg
65                  70                  75                  80

Val Gly Glu Ile Lys Gly Gly Tyr Val Glu Leu Lys Arg Gly Glu Lys
                85                  90                  95

Val Ile Leu Thr Thr Lys Asp Val Glu Gly Asp Glu Thr Thr Ile Pro
            100                 105                 110

Val Asp Tyr Lys Gly Phe Pro Asn Leu Val Ser Lys Gly Asp Ile Ile
        115                 120                 125

Tyr Leu Asn Asp Gly Tyr Ile Val Leu Lys Val Glu Asn Val Arg Glu
    130                 135                 140

Asn Glu Val Glu Ala Val Val Leu Ser Gly Gly Lys Leu Phe Ser Arg
145                 150                 155                 160

Lys Gly Val Asn Ile Pro Lys Ala Tyr Leu Pro Val Glu Ala Ile Thr
                165                 170                 175

Pro Lys Asp Phe Glu Ile Met Lys Phe Ala Ile Glu His Gly Val Asp
            180                 185                 190

Ala Ile Gly Leu Ser Phe Val Gly Ser Val Tyr Asp Val Leu Lys Ala
        195                 200                 205

Lys Ser Phe Leu Glu Lys Asn Asn Ala Glu Asp Val Phe Val Ile Ala
    210                 215                 220

Lys Ile Glu Arg Pro Asp Ala Val Arg Asn Phe Asp Glu Ile Leu Asn
225                 230                 235                 240

Ala Ala Asp Gly Ile Met Ile Ala Arg Gly Asp Leu Gly Val Glu Met
                245                 250                 255

Pro Ile Glu Gln Leu Pro Ile Leu Gln Lys Leu Ile Arg Lys Ala
            260                 265                 270

Asn Met Glu Gly Lys Pro Val Ile Thr Ala Thr Gln Met Leu Val Ser
        275                 280                 285

Met Thr Thr Glu Lys Val Pro Thr Arg Ala Glu Val Thr Asp Val Ala
    290                 295                 300

Asn Ala Ile Leu Asp Gly Thr Asp Ala Val Met Leu Ser Glu Glu Thr
305                 310                 315                 320

Ala Ile Gly Lys Phe Pro Ile Glu Thr Val Glu Met Met Gly Lys Ile
                325                 330                 335

```
Ala Lys Val Thr Glu Glu Tyr Arg Glu Ser Phe Gly Leu Ser Arg Ile
            340                 345                 350

Arg Glu Phe Met Glu Ile Lys Lys Gly Thr Ile Lys Glu Ala Ile Thr
            355                 360                 365

Arg Ser Ile Ile Asp Ala Ile Cys Thr Ile Asp Ile Lys Phe Ile Leu
        370                 375                 380

Thr Pro Thr Arg Thr Gly Arg Thr Ala Arg Leu Ile Ser Arg Phe Lys
385                 390                 395                 400

Pro Lys Gln Trp Ile Leu Ala Phe Ser Thr Asn Glu Arg Val Cys Asn
                405                 410                 415

Asn Leu Met Phe Ser Tyr Gly Val Tyr Pro Phe Cys Leu Glu Glu Gly
            420                 425                 430

Phe Asp Glu Asn Asp Ile Val Arg Leu Ile Lys Gly Leu Gly Leu Val
        435                 440                 445

Glu Ser Asp Asp Met Val Leu Met Thr Glu Gly Lys Pro Ile Glu Lys
    450                 455                 460

Thr Val Gly Thr Asn Ser Ile Lys Ile Phe Gln Ile Ala
465                 470                 475

<210> SEQ ID NO 25
<211> LENGTH: 408
<212> TYPE: PRT
<213> ORGANISM: Methanosarcina thermophila

<400> SEQUENCE: 25

Met Lys Val Leu Val Ile Asn Ala Gly Ser Ser Leu Lys Tyr Gln
1               5                   10                  15

Leu Ile Asp Met Thr Asn Glu Ser Ala Leu Ala Val Gly Leu Cys Glu
            20                  25                  30

Arg Ile Gly Ile Asp Asn Ser Ile Ile Thr Gln Lys Lys Phe Asp Gly
        35                  40                  45

Lys Lys Leu Glu Lys Leu Thr Asp Leu Pro Thr His Lys Asp Ala Leu
    50                  55                  60

Glu Glu Val Val Lys Ala Leu Thr Asp Glu Phe Gly Val Ile Lys
65                  70                  75                  80

Asp Met Gly Glu Ile Asn Ala Val Gly His Arg Val Val His Gly Gly
                85                  90                  95

Glu Lys Phe Thr Thr Ser Ala Leu Tyr Asp Glu Gly Val Glu Lys Ala
            100                 105                 110

Ile Lys Asp Cys Phe Glu Leu Ala Pro Leu His Asn Pro Pro Asn Met
        115                 120                 125

Met Gly Ile Ser Ala Cys Ala Glu Ile Met Pro Gly Thr Pro Met Val
    130                 135                 140

Ile Val Phe Asp Thr Ala Phe His Gln Thr Met Pro Pro Tyr Ala Tyr
145                 150                 155                 160

Met Tyr Ala Leu Pro Tyr Asp Leu Tyr Glu Lys His Gly Val Arg Lys
                165                 170                 175

Tyr Gly Phe His Gly Thr Ser His Lys Tyr Val Ala Glu Arg Ala Ala
            180                 185                 190

Leu Met Leu Gly Lys Pro Ala Glu Glu Thr Lys Ile Ile Thr Cys His
        195                 200                 205

Leu Gly Asn Gly Ser Ser Ile Thr Ala Val Glu Gly Gly Lys Ser Val
    210                 215                 220

Glu Thr Ser Met Gly Phe Thr Pro Leu Glu Gly Leu Ala Met Gly Thr
225                 230                 235                 240
```

```
Arg Cys Gly Ser Ile Asp Pro Ala Ile Val Pro Phe Leu Met Glu Lys
                245                 250                 255

Glu Gly Leu Thr Thr Arg Glu Ile Asp Thr Leu Met Asn Lys Lys Ser
            260                 265                 270

Gly Val Leu Gly Val Ser Gly Leu Ser Asn Asp Phe Arg Asp Leu Asp
        275                 280                 285

Glu Ala Ala Ser Lys Gly Asn Arg Lys Ala Glu Leu Ala Leu Glu Ile
    290                 295                 300

Phe Ala Tyr Lys Val Lys Lys Phe Ile Gly Glu Tyr Ser Ala Val Leu
305                 310                 315                 320

Asn Gly Ala Asp Ala Val Val Phe Thr Ala Gly Ile Gly Glu Asn Ser
                325                 330                 335

Ala Ser Ile Arg Lys Arg Ile Leu Thr Gly Leu Asp Gly Ile Gly Ile
            340                 345                 350

Lys Ile Asp Asp Glu Lys Asn Lys Ile Arg Gly Gln Glu Ile Asp Ile
        355                 360                 365

Ser Thr Pro Asp Ala Lys Val Arg Val Phe Val Ile Pro Thr Asn Glu
    370                 375                 380

Glu Leu Ala Ile Ala Arg Glu Thr Lys Glu Ile Val Glu Thr Glu Val
385                 390                 395                 400

Lys Leu Arg Ser Ser Ile Pro Val
                405

<210> SEQ ID NO 26
<211> LENGTH: 585
<212> TYPE: DNA
<213> ORGANISM: Sulfolobus acidocaldarius

<400> SEQUENCE: 26
atgaagattg gtattgtaac tggaattcct ggtgtaggga aaagtactgt cttggctaaa      60
gttaaagaga tattggataa tcaaggtata aataacaaga tcataaatta tggagatttt    120
atgttagcaa cagcattaaa attaggctat gctaaagata gagacgaaat gagaaaatta    180
tctgtagaaa agcagaagaa attgcagatt gatgcggcta aggtatagc tgaagaggca     240 agagcaggtg gagaaggata tctgttcata gatacgcatg ctgtgatacg tacaccctct    300
ggatatttac ctggtttacc gtcatatgta attacagaaa taaatccgtc tgttatcttt    360
ttactggaag ctgatcctaa gataatatta tcaaggcaaa agagagatac aacaaggaat    420
agaaatgatt atagtgacga atcagttata ttagaaacca taaacttcgc tagatatgca    480
gctactgctt ctgcagtatt agccggttct actgttaagg taattgtaaa cgtggaagga    540
gatcctagta tagcagctaa tgagataata aggtctatga agtaa                    585

<210> SEQ ID NO 27
<211> LENGTH: 585
<212> TYPE: DNA
<213> ORGANISM: Artificial Sequence
<220> FEATURE:
<223> OTHER INFORMATION: Synthetic

<400> SEQUENCE: 27
atgaaaatcg gtatcgttac cggtatcccg ggtgttggta aatctaccgt tctggctaaa     60
gttaaagaaa tcctggacaa ccagggtatc aacaacaaaa tcatcaacta cggtgacttc    120
atgctggcta ccgctctgaa actgggttac gctaaagacc gtgacgaaat gcgtaaactg    180
tctgttgaaa aacagaaaaa actgcagatc gacgctgcta aggtatcgc tgaagaagct     240 cgtgctggtg gtgaaggtta cctgttcatc gacacccacg ctgttatccg taccccgtct    300
```

-continued

```
ggttacctgc cgggtctgcc gtcttacgtt atcaccgaaa tcaacccgtc tgttatcttc    360
ctgctggaag ctgacccgaa atcatcctg tctcgtcaga acgtgacac cacccgtaac    420 cgtaacgact actctgacga atctgttatc ctggaaacca tcaacttcgc tcgttacgct    480
gctaccgctt ctgctgttct ggctggttct accgttaaag ttatcgttaa cgttgaaggt    540
gacccgtcta cgctgctaa cgaaatcatc cgttctatga aatag                     585
```

<210> SEQ ID NO 28
<211> LENGTH: 663
<212> TYPE: DNA
<213> ORGANISM: Thermotoga maritima

<400> SEQUENCE: 28

```
atgatggcgt accttgtctt ctaggacct ccaggtgcag gaaaaggaac ctacgcaaag    60
agattgcagg aaataacggg gattcctcat atatccaccg gtgacatttt cagggacatt    120
gtaaaaaaag agaacgacga gcttgggaaa agataaaag gatcatgga agggggagaa    180 ctcgttccgg acgaactcgt gaacgaggtt gtgaaaagaa gactctcaga aaagattgt    240 gaaagaggat tcatactgga cggctatcca gaaccgttg ctcaggcgga attcctcgac    300 ggcttttga aaactcaaaa caaagagctc acggctgctg tactctttga agttcctgag    360
gaagtggtcg ttcagaggct cacggccaga aggatctgcc cgaaatgtgg aagaatttac    420
aatttgattt cgctccctcc aaaagaagac gaactgtgcg atgattgtaa agtgaagctc    480
gttcagagag aagacgacaa agaagaaaca gtgagacaca gatacaaggt ttatctcgaa    540
aagacacagc cagtgattga ttactacgat aaaaagggca ttctcaaacg agtggatggt    600
accataggaa tagacaacgt gatcgctgaa gtgttaaaga taatagggtg gagtgataaa    660
tga                                                                   663
```

<210> SEQ ID NO 29
<211> LENGTH: 660
<212> TYPE: DNA
<213> ORGANISM: Artificial Sequence
<220> FEATURE:
<223> OTHER INFORMATION: Synthetic

<400> SEQUENCE: 29

```
atgatggcct atctggtttt tcttggtcca ccggggggcag gcaaaggtac atatgcgaaa    60
cgtttacagg aaatcaccgg catcccgcac attagcacgg gcgacatttt tcgtgatatt    120
gtcaaaaagg aaaatgacga attaggtaag aaaattaaag aaattatgga gcgcggcgag    180
ttggtgccgg acgaactggt gaatgaagtt gtcaaacgtc ggctgtctga aaaggattgc    240
gaacgtggct ttatttggga cggttacccg cgtacagtag ctcaggcaga gtttctcgac    300
ggcttcctga agactcagaa taaggagtta acggctgcgg tcctgttcga ggtgcctgaa    360
gaggtggtcg ttcagcgtct gaccgcgcgg cgtatctgcc cgaagtgtgg tcgtatttac    420
aacctgattt cacttcctcc aaaagaagat gaactgtgtg atgactgcaa agtaaaactg    480
gtgcaacgcg aagatgataa agaggaaact gtgcgccatc gctacaaagt atatctggaa    540 aaacccaac cggttatcga ttattatgat aaaaaaggca ttttgaaacg cgttgatggg    600
accatcggca tcgataacgt gattgccgaa gttctcaaaa tcattgggtg gagtgataaa    660
```

<210> SEQ ID NO 30
<211> LENGTH: 651
<212> TYPE: DNA
<213> ORGANISM: Artificial Sequence -continued

```
<220> FEATURE:
<223> OTHER INFORMATION: Synthetic

<400> SEQUENCE: 30
atgaacctga ttttcctggg tccgcctggg gcaggcaaag gcacccaggc gaaacgtgtg      60
tctgaaaagt acggtatccc gcagattagt accggcgata tgctgcgtga agcggttgct     120
aagggtacgg aactggggaa aaaggcgaaa gaatatatgg acaaagggga acttgttccg     180
gatgaagtag ttattggaat cgtgaaagaa cgcctccagc aaccggattg tgagaagggc     240
tttattctgg acggttttcc gcgtacgtta gcacaagccg aagctctgga cgaaatgtta     300
aaagaattga ataagaaaat tgacgccgta atcaacgtgt tcgtaccgga agaggaagtt     360
gtcaagcgta ttacctatcg tcgcacttgc cgcaattgcg gcgccgtgta ccatctcatt     420
tatgcacctc caaaagagga taataaatgt gataaatgcg gcggtgagct ttatcagcgt     480
gatgacgata aagaagagac agtccgcgag cgttaccgtg tgtataaaca gaacacagag     540
ccattgatcg attattaccg taaaaaggga atcctgtatg atgtggatgg tactaaagac     600
atcgaaggag tttggaaaga aattgaggcg attctggaaa aaattaaaag c              651
```

BIOLOGICAL INDICATOR

The invention relates to a biological indicator suitable for the validation of processes, including heat-based inactivation processes and inactivation procedures in general, and more specifically for the validation of procedures to inactivate transmissible spongiform encephalopathy (TSE) agents.

Creutzfeldt-Jakob Disease (CJD) is a relatively rare form of human neurodegenerative disorder presenting as either a familial, sporadic or iatrogenic disease at a frequency of approximately 1 case per million population. The emergence of a new variant form (vCJD) of the disease, predominantly in a younger age group, and possibly due to consumption of bovine spongiform encephalopathy (BSE)-infected meat products, has raised the possibility of a large increase in the numbers of cases. These factors have important public health consequences. A large proportion of the UK population has potentially been exposed to the disease via food during the late 1980s. Whilst the number of cases to date has been relatively low (149 cases to February 2004) there remains a significant risk, from all forms of CJD, via other transmission routes including surgery, transplants, transfusion or contaminated medical products. A number of these routes have been implicated in the iatrogenic spread of the disease in a clinical setting and others have been defined in animal models.

The agents responsible for causing all forms of CJD in humans are highly resistant to inactivation by standard methods. Validated methods for the decontamination of surgical instruments are urgently required. A variety of treatments, including chemical treatments and the use of high temperatures and pressures with wet or dry heat, have been tested but none are adequate [Taylor, D. M. (1999) in: Principles and practice of disinfection, preservation and sterilisation. (Russell, A. D., Hugo, W. B. and Ayliffe, G. A. J., Eds): pp. 222-236 Blackwell Scientific Publications, Oxford; Taylor, D. M. (2001) Contrib Microbiol. 7, 58-67; Taylor, D. M., Fernie, K, Steele, P. J., McConnell, I. and Somerville, R. A. (2002) J Gen Virol. 83, 3199-3294]. Incineration is effective, but precludes any recovery or reuse of raw materials or equipment. The use of high concentrations of sodium hydroxide (up to 2M) or high levels of sodium hypochlorite (up to 20000 ppm) have been shown to significantly reduce the levels of TSE agents, but have a deleterious effect on surgical instruments and may be harmful to the operator. A wide variety of other methods have been proposed as means of inactivating TSE agents on surgical instruments and are currently in development. These include a variety of gaseous phase sterilants including vapour phase hydrogen peroxide, ozone and ethylene oxide. Other methods have been proposed as a specific anti-TSE pre-treatment prior to routine sterilisation and these include treatment of the surgical instruments using thermostable proteases under defined conditions of pH and temperature.

Inactivation of *Bacillus stearothermophilus* spores is a method routinely used to validate the correct performance of autoclaves. Such indicators may represent a relevant indication that a bacteria or virus has been inactivated by the process, with the process usually validated as reducing the level of infectious agent by an order of $10^6$. However, the uniquely stable properties of the TSE agents mean that a much more robust indicator is required to provide a relevant indication of the performance of processes to inactivate such agents.

Other biological indicators, based on thermostable spores or enzymatic preparations are well known to those familiar with the art. All have the drawback that they are unable to validate inactivation of an infectious agent in excess of a $10^6$ reduction in activity.

Inactivation of TSE agents is also a significant issue for the disposal of Bovine Spongiform Encephalopathy (BSE)-infectious materials and in the preparation of raw materials of animal origin. There is now a good body of scientific evidence that the emergence and spread of BSE was via changes in rendering practice with highly infectious neuronal tissue being fed back to cattle via meat-and-bone-meal supplements. There is also good evidence that BSE was the cause of vCJD, almost certainly as the result of eating contaminated beef products. For this reason any cattle that die of BSE, together with spinal cord and brain tissue from all cattle, are currently removed from the food chain and disposed of by an alternative route. This has the result that enormous amounts of animal waste is currently being accumulated or disposed of by incineration. The treatment of such material with thermostable proteases is one possible solution. Again there is a requirement for a validation procedure to ensure that any infectious material is destroyed in an appropriate process.

It is an object of the present invention to provide an alternative and/or improved biological indicator and uses thereof.

Accordingly, in a first aspect of the invention, there is provided a biological process indicator for validating a treatment process for reducing the amount or activity of a biological agent in a sample, comprising a kinase. In a preferred embodiment, the indicator further comprises a solid support, wherein the kinase is immobilised in or immobilised on said solid support. In a particularly preferred embodiment, the kinase is a thermostable kinase.

In a use of the invention, a biological indicator is included in a sample that is being subjected to a treatment that is intended to reduce its content of a potential contaminant, especially an infectious agent. It is known from previous tests that the reduction in activity of the indicator kinase by the treatment can be correlated with reduction in amount or activity of the contaminant. To determine whether the amount/activity of the contaminant has been reduced below an acceptable level, the activity of the indicator kinase is measured before and after, or during, the treatment. When a level of activity is reached that is known to correlate with an acceptable reduction in the contaminant, the treatment is then regarded as validated. If the contaminant is an infectious agent, then the sample may be regarded as sterile.

In a particular use of the invention, thermostable kinase is the reporter in a method of indicating the possible presence of an agent (e.g. an infectious agent) following a cleaning or inactivation procedure. First, a sample containing thermostable adenylate, acetate or pyruvate kinase is exposed to a cleaning/inactivation procedure (e.g. one or more of a selected temperature, pH or protease concentration). The next step is to remove any contaminating enzymatic activity by heat treatment, e.g., at from 60 to 80° C. for at least 10 minutes (i.e. under conditions that do not significantly affect the thermostable kinase). The thermostable kinase is then reacted at a temperature of between 30° C. and 70° C. with a substrate (e.g. ADP) to allow the generation of ATP. The formation of ATP can be measured by bioluminescent detection using luciferin/luciferase and a suitable luminometer at 20-30° C. for 10 minutes to 1 hour. The reading from the luminometer gives a reading of the residual kinase activity, i.e. the activity of the kinase following exposure to the cleaning/inactivation treatment. Based on data that have been previously derived from separate experiments, the method is completed by correlating the residual kinase activity with the possible presence of an infectious agent within the treated sample.

In one embodiment, contaminating enzymatic activity or ATP in a sample may be removed by an initial treatment step (e.g. a selected temperature, pH or protease concentration), prior to addition of the indicator.

Kinase enzymes have been found to be capable of generating a signal that is detectable over an extremely wide range. Generally, the kinase is detected using a substrate comprising ADP which is converted to ATP, itself used to generate light, eg. using luciferin/luciferase, detected using a luminometer. The wide range makes the indicator particularly suitable for validation as the kinase remains detectable even after many logs reduction in amount/activity. For sterility, most national institutes regard a 6 log reduction in the amount or activity of a biological agent as required before sterility can be validated. The kinases of the invention offer the potential of validating reduction in the amount or activity of agents well beyond 6 logs, to 8 logs and more, thus increasing the scope of monitoring offered at present.

In preferred embodiments of the invention, the kinase is thermostable, and is hence suitable for use in validation of processes carried out at high temperature. Thermostable kinases are also found to be resistant to other extreme environments, and are for example often found resistant to extremes of pH and resistant to exposure to proteolytic enzymes. So the kinases of the invention can be used for monitoring treatments of biological agents that employ one or a combination or all of high pH, high temperature and proteases.

By thermostable is meant that at least 95% of the activity of the kinase is retained after exposure to 70 degrees C. for 30 minutes. Preferred enzymes of the invention are very thermostable and will retain at least 95% activity after heating to 80 degrees C. for 10 minutes. The kinases from mesophilic organisms and even a variety of thermophilic organisms, such as *Bacillus stearothermophilus* (used widely as a biological indicator) do not meet these criteria, but may nevertheless be suitable as indicators for treatments carried out at lower temperatures.

The kinases used in particular embodiments of the invention are adenylate kinase, acetate kinase and pyruvate kinase, or combinations thereof. Further, the adenylate, acetate and pyruvate kinase enzymes may be obtained from *Pyrococcus furiousus, P. abyssi, P. horikoshii, P. woesii, Sulfolobus solfataricus, S. acidocaldarius, S. shibatae, Rhodothermus marinus, Thermococcus litoralis, Thermatoga maritima, Thermatoga neapolitana* and *Methanococcus* spp. Adenylate kinase is especially preferred and has been used in examples of the invention set out in detail below. The kinases catalyse formation of ATP from a substrate comprising ADP, and the ATP is then readily detected using known methods and reagents. Specific kinases suitable for the invention are set out in SEQ ID NO.s 1-30.

ATP bioluminescent detection is a preferred means of detecting kinase activity. A standard luciferin-luciferase assay method can detect as little as $10^{-15}$ moles of ATP. By coupling an enzymatic amplification to the bioluminescent detection methods it is possible to detect as few as $10^{-20}$ moles of kinase. This type of format therefore offers remarkable sensitivity for the detection of molecules using binding species linked to adenylate kinase (AK) as described in WO 02/053723.

Use of a kinase, e.g. AK, coupled to bioluminescent detection has a number of other significant advantages. The assay gives a direct relationship between enzymatic activity and light production over a much larger range than other comparable assay formats. Thus whilst an assay using a traditional reporter enzyme such as horseradish peroxidase or alkaline phosphatase will give a proportional response over 5-6 log dilutions, the AK-luciferase assay can provide a dynamic range of at least 8 logs. As direct indicators this makes them especially useful for processes which require a level of inactivation greater than the standard 6-log range as the signal can be made to be meaningful across the whole range of the assay, something that would not be possible using other assay formats. This is particularly relevant for TSE inactivation where, in a worse case scenario, as many as 8-logs of infectivity may be present on the surface of a surgical instrument, assuming the presence of 1 mg brain tissue at a level of up to $10^8$ TSE infectious units per mg. Under these circumstances an indicator of the invention, providing an 8-log range of signal is particularly valuable.

Given the type of processes for which a TSE indicator is required a high level of both thermal and physical stability is preferred. In an example below, the properties of a range of AK enzymes from thermophilic organisms were compared. Even AKs from thermophilic organisms such as the indicator strain *B. stearothermophilus* lose the majority of their activity at relatively low temperatures. For a kinase-based indicator to be included in e.g an autoclaving cycle, a significantly greater degree of thermostability, such as that demonstrated by the enzymes from the *Sulfolobus* species or *Pyrococcus furiosus*, is used.

A number of additives and changes to formulation that increase the stability of an enzyme, e.g. a kinase, to heat inactivation will be known to those familiar with the art. The thermostable kinases used in embodiments of this invention will require significantly less stabilisation given that they are already significantly more stable than other enzymes used for this type of process. AK enzymes described herein, in particular the AK enzymes from *Sulfolobus acidocaldarius, S. solfataricus, S. shibatae, Pyrococcus furiosus, Rhodothermus marinus* and *Thermococcus litoralis*, are significantly more stable at both 80° C. and 90° C. than even the enzyme from an organism normally used as an indicator of process sterilisation such as *Bacillus stearothermophilus*. In many cases these AK enzymes immobilised on a solid support may require no further stabilisation to provide the necessary range of activity to be measured following e.g. autoclaving, pasteurisation or equivalent.

The addition of stabilising agents such as sorbitol up to a concentration of 4M, or other polyols such as ethylene glycol, glycerol, or mannitol at a concentration of up to 2M may improve the thermostability of the enzyme. Other additives such as xylan, trehalose, gelatin may also provide additional stabilisation effects either individually or in combination. Addition of a range of divalent metal ions, most notably $Ca^{2+}$, $Mg^{2+}$ or $Mn^{2+}$ may also improve stability of the enzyme.

Chemical modification of the enzymes can also be used to improve their thermal stability. Reductive alkylation of surface exposed amino groups by glyoxylic acid (e.g Melik-Nubarov (1987) Biotech letts 9:725-730), addition of carbohydrates to the protein surface (e.g. Klibanov (1979) Anal. Biochem. 93:1-25) and amidation (e.g. Klibanov (1983) Adv. Appl. Microbiol. 29:1-28) may all increase the stability of the enzyme. Further methods including the use of chemical cross-linking agents and the use of various polymeric supports for enzyme immobilisation are also relevant methods for increasing the thermostability of enzymes (reviewed in Gupta (1991) Biotech. Appl. Biochem. 14:1-11).

Similar modifications are also relevant to the stabilisation of the indicator against other sterilisation processes such as hydrogen peroxide or ozone. In particular, processes where the access of the gaseous phase sterilant to the enzyme is restricted, for example by encapsulation in a suitable polymer or formulation with an additive to reduce penetration of the gas, will provide useful methods for increasing the stability of the enzyme if required.

Many of the treatments that are effective at increasing the thermal stability of enzymes are also relevant to the stabilisation for protease treatments, e.g. for the development of an indicator for the effective inactivation of TSE agents by protease treatment. In general a protein that shows high levels of thermostability is likely to also show a high degree of stability for degradative processes such as denaturation or protease treatment (See for example: Daniel R M, Cowan D A, Morgan H W, Curran M P, "A correlation between protein thermostability and resistance to proteolysis", Biochem J. 1982 207: 641-4; Rees D C, Robertson A D, "Some thermodynamic implications for the thermostability of proteins", Protein Sci. 2001 10:1187-94; Burdette D S, Tchernajencko V V, Zeikus J G. "Effect of thermal and chemical denaturants on *Thermoanaerobacter ethanolicus* secondary-alcohol dehydrogenase stability and activity", Enzyme Microb Technol. 2000 27:11-18; Scandurra R, Consalvi V, Chiaraluce R, Politi L, Engel P C., "Protein thermostability in extremophiles", Biochimie. 1998 November; 80(11):933-41; and Liao H H., "Thermostable mutants of kanamycin nucleotidyltransferase are also more stable to proteinase K, urea, detergents, and water-miscible organic solvents", Enzyme Microb Technol. 1993 April; 15(4):286-92). The thermostable kinases therefore generally show a higher degree of stability to the actions of the protease treatments designed to inactivate TSE agents than might an equivalent mesophilic kinases. Depending on the type of process used, a kinase can also be selected to favour other characteristics of the process. Thus for a protease treatment at alkaline pH the protocol tends towards the use of a thermostable kinase from a moderately alkalophilic organism such as *P. furiosus*, whereas a protease treatment at acidic pH might use a kinase from an acidophile such as *S. acidocaldarius* or *S. solfotaricus*.

If required to improve the stability of the kinase indicator to protease treatment a number of other options exist. A number of these are the same as those described above for the stabilisation of the enzyme against heat treatment.

For example formulations containing sorbitol, mannitol or other complex polymers reduce the levels of inactivation of the enzyme on the indicator surface. In addition treatments that specifically reduce the rate at which a protease substrate is degraded are particularly relevant to this application. For example the formulation of the kinase in a solution containing up to around 10 mg/ml (a 10-fold excess compared to the preferred concentration of the indicator) of a suitable carrier protein such as casein or albumin, that acts as alternative substrate for the protease, will specifically reduce the rate of digestion of the kinase indicator. Similarly the addition of free amino acids such as glycine, tyrosine, tryptophan or dipeptides to the formulation would provide a means of substrate level inhibition of the enzyme and reduce local inactivation of the kinase indicator.

The invention additionally provides methods for the production of various thermostable kinases by recombinant expression in bacteria for use as biological indicators.

The genetic modification of enzymes has been shown to provide significant increases in thermal stability and by analogy such mutations are also likely to significantly enhance the stability of the indicator enzymes in other processes such as protease treatment or gaseous phase "sterilisation". The comparison of the thermostability of the kinase enzymes shown in FIG. 1 taken with the defined 3-D structure of the trimeric (archaeal) AKs (Vonrhein et al (1998) J. Mol. Biol. 282:167-179 and Criswell et al (2003) J. Mol. Biol. 330:1087-1099) has identified amino acids that influence the stability of the enzyme.

Genetically engineered variants of kinases showing improved thermostability are also provided by and used in the invention, and can be generated in a number of ways. Essentially these involve the specific site-directed mutagenesis of amino acids believed to form part of the central core packing region of the trimeric molecule and random "directed evolution" methods where the whole molecule is subjected to subsequent rounds of mutagenesis and selection/screening of molecules with improved properties. The modifications outlined herein, e.g. in Examples 8-10, are based on a hybrid approach using a consensus based approach to define regions likely to influence the thermostability of the enzymes based on observed differences between structurally related molecules. This is followed by either defined changes to incorporate the amino acids that correlate with the best thermostability or a random replacement to incorporate every available amino acid at the positions defined as being essential for thermostability.

Specific modified enzymes of the invention are the various variants set out in Examples 8-10 and referred to collectively as SEQ ID NOs: 17-19 (though several variants are embraced by each reference).

The biological indicator can be adapted for use in a vessel in which an sample is being processed. For example, the indicator includes a solid support which is a matrix and the kinase is dispersed within the matrix. The matrix should be resistant to the process conditions and can help to provide protection to the kinase from the process—hence providing some stabilization to the indicator. The kinase can be located within a polymer matrix. The support can be designed to project into or be added to a processing vessel, and can be an indicator strip, a dip stick or a bead.

A variety of solid supports, with or without chemical modifications and with one or more kinase indicators in a variety of formulations, are embraced by the invention, depending e.g. on the requirements of the process to be validated. In one form the support is a plastic, ceramic, steel or other metallic or polymer surface onto which the kinase is dried as a means of immobilisation. The support can be a polycarbonate, polystyrene or polypropylene strip or dipstick, possibly with a flattened surface, onto which the kinase is applied. An additional type of support with a porous surface for attachment of kinase is also particularly useful as an indicator for gaseous processes. Kinase coated plastic, metallic or ceramic beads may also provide a valuable format for the indicator, again with specific relevance to monitoring gaseous processes. Such supports have advantages over solid supports for certain applications, as they provide a significantly increased surface area for the attachment of the indicator.

For the specific example of a device formulated for the validation of TSE inactivation processes, a steel surface such as a rod, disk or coupon is an effective indicator for surgical instrument decontamination. The binding of a thermostable adenylate kinase, for example, is a very good model of the aggregated form of the disease-related prion isoform ($PrP^{Sc}$) and as such provides a remarkably good indicator of $PrP^{Sc}$'s interaction with the surface of surgical steel.

Binding of kinase on or to the support of the indicator may be achieved by methods routinely used to link protein to surfaces, e.g. incubation of protein in 0.1M sodium bicarbonate buffer at about pH9.6 at room temperature for about 1 hour. Alternatively the protein is covalently coupled to the surface using any of a wide range of coupling chemistries known to those familiar with the art. For example an adenylate kinase derivitised with SPDP (Pierce chemicals; using manufacturer's instructions), reduced with DTT to provide free sulfhydryl groups for cross-linking, is covalently attached to a polystyrene support with a maleimide surface. Plastic surfaces with such sulfhydryl-binding surfaces are well described in the literature. An added benefit of this method of coupling is that, if required, the enzyme can be cleaved from the support eg. by reduction with DTT or MESNA, to allow the assay to be carried out separately to any indicator support. The adenylate kinase enzymes and other indicator kinases described by this invention have the property that their activity is retained upon derivitisation and cross-linking to such supports.

Alternatively an amine reactive surface on a polystyrene or polycarbonate support is used, with a bifunctional cross-linking agent such as monomeric glutaraldehyde, to provide direct non-cleavable cross-linking of the kinase via free amine groups on the protein. UV treatment can also be used to directly link the indicator to a suitable support. Steel surfaces can be treated in a similar way to plastic surfaces to mediate covalent attachment of the indicator kinase.

A wide variety of protein cross-linking reagents are available from companies such as Pierce chemical company (Perbio). Reagents reactive to sulfhydryl, amino, hydroxyl and carboxyl groups are designed for coupling proteins but they can equally be used for cross-linking proteins to either naturally reactive or coated solid supports such as plastics, other polymers, glass and metals. Reactive chemistries are also available for cross-linking the enzymes to carbohydrates. For example, the reagents BMPH ((N-[β-Maleimidopropionic acid]hydrazide.TFA), KMUH ((N-[k-Maleimidoundecanoic acid]hydrazide), and MPBH (4-(4-N-Maleimidophenyl)butyric acid hydrazide hydrochloride) can be used to cross link the kinase containing either a free sulfhydryl in the form of a cysteine residue or a chemically derivitised protein reduced to generate a sulfhydryl reactive group, to carbohydrates. This may be particularly important for a solid support which is either a complex carbohydrate (e.g. paper, cellulose-based membranes, gels or resins) or can be coated or treated with a carbohydrate solution to generate a suitably reactive surface.

For each type of support the kinase is preferably formulated in a solution that enhances binding and/or stabilises the bound protein. Such formulations include solutions containing up to 10% (w/v) sucrose, sorbitol, mannitol, cellulose, or polyethylene glycol (PEG). In addition the kinase can be formulated as part of a gel that is applied to the surface or lumen of a suitable support. Examples include alginate, agar or polyacrylamide matrices.

The indicator may also comprise an agent to stabilise the kinase, and suitable stabilising agents are selected from metal ions, sugars, sugar alcohols and gel-forming agents.

To facilitate use of the indicator, it may further comprise means to attach the indicator to a surface, such as a projection, recess or aperture for attachment of the support to a surface by means of a screw, nut and bolt or clamp.

In specific embodiments of the invention, purified kinase, e.g. adenylate kinase (AK), is formulated at a concentration of up to 1 mg/ml and coated onto solid supports. Preferably, between 1-2 mg, or 0.5-1 mg, or 0.1-0.5 mg, or 0.1 mg, of kinase is coated onto the solid support. For protease treatment, the kinase may be dried onto a polypropylene, polycarbonate or polystyrene surface similar to microtitre plates. For either standard autoclaving at 121° C. for 15-20 minutes or "prion-cycle" autoclaving at 134° C. for 18 minutes, a heat-stable support such as stainless steel may be used. For gas phase inactivation procedures such as hydrogen peroxide or ozone, polycarbonate solid support may be used, and can also be manufactured as a porous matrix to provide a greater degree of resistance to the inactivant if required.

A convenient solid support takes the form of a dipstick which is transferred directly from the inactivation procedure to a tube containing all the required assay components. This can be a tube luminometer attached to one of a range of "rapid read-out" hygiene monitors already on the market for the food and pharmaceutical industry. Alternatively it can take the form of a specialised instrument designed for the indicator in question, with a particular emphasis on maintaining the optimal temperatures required by the thermostable enzymes (see Example 24).

The present invention also provides a biological indicator comprising a plurality of enzymes detectable after differing levels of inactivation of the biological agent. A biological indicator of one embodiment comprises a support, a first enzyme located at a first position and a second enzyme located at a second position, separate from the first position. Both the first and second enzymes have activity in converting product to substrate and after exposure of the biological indicator to an inactivation process for an initial period of time activity of both enzymes can be detected. After exposure of the biological indicator to the inactivation process for a subsequent period of time, activity of the first enzyme cannot be detected but activity of the second enzyme can be detected. After exposure of the biological indicator to the inactivation process for a second subsequent period of time, activity of the second enzyme cannot be detected.

An advantage of this embodiment is that the indicator can be used to show an approximate level of inactivation of the biological agent achieved by the process without the need for a precise measurement to be taken. Thus, for example, when both enzymes are detectable this can indicate that the inactivation has not reached a certain threshold. When only the second enzyme can be detected this indicates that the first threshold of inactivation has been reached but a second threshold has not. Lastly, when neither enzyme can any longer be detected this indicates that the inactivation has passed the second threshold. If the first enzyme is detectable at up to 6 logs reduction in activity and the second enzyme is detectable at up to 8 logs reduction in activity, then being able to detect both enzymes indicates that inactivation has not reached 6 logs, being able to detect only the second enzyme indicates activity has been reduced by between 6 and 8 logs and being able to detect neither indicates that at least 8 logs reduction in activity has been achieved.

The first enzyme is suitably detectable at up to between 5 and 8 logs reduction in activity and the second enzyme is suitably detectable at 6 logs or greater reduction in activity. The first enzyme is preferably detectable at between 6 and 7 logs reduction in activity and the second enzyme is preferably detectable at between 7 and 8 logs reduction in activity. The biological indicator may further comprise a third enzyme located at a third position (separate from the first and second positions), wherein after exposure of the biological indicator to the inactivation process for the second subsequent period of time, the third enzyme can be detected, and after exposure of the biological indicator to the inactivation process for a third subsequent period of time, the third enzyme cannot be detected. The third enzyme is suitably detectable at 8 logs reduction in activity or greater.

Using a biological indicator of this type, having multiple enzymes that are detectable at differing levels treatment (e.g. a different exposure time), the progression of the inactivation progress can be watched and its end point anticipated readily.

The preferred enzymes of the multi-enzyme indicator are kinases, more preferably thermostable and more preferably as disclosed and described herein in relation to other embodiments of the invention.

In a second aspect of the invention, there is provided a kit (optionally a portable kit) for use in validating a treatment process for reducing the amount or activity of a biological agent in a sample, comprising:
(i) a biological process indicator according to the first aspect of the invention, and
(ii) substrate for the kinase.

To carry out measurement of the kinase amount/activity, the kit can include means for detecting ATP, e.g. luciferin/luciferase and optionally a luminometer. The substrate is preferably ADP.

From previous testing with known biological agents, data correlating reduction in the amount or activity of the biological agent with kinase activity can be prepared, and the kit therefore can also include one or more look-up tables correlating kinase activity with the reduction in amount or activity of a list of specified biological agents. In preferred embodiments, the kit is for monitoring TSE inactivation.

In a third aspect of the invention, there is provided a method of validating a treatment process, comprising:
(i) obtaining a sample that contains, or is suspected to contain, a biological agent;
(ii) subjecting the sample to a treatment in the presence of a defined amount of a kinase, wherein the treatment reduces the amount or activity of the biological agent;
(iii) measuring residual kinase activity and optionally calculating the reduction in kinase activity; and
(iv) comparing said residual activity to a predetermined kinase activity, or comparing said reduction in kinase activity to a predetermined reduction in kinase activity, wherein the predetermined kinase activity or predetermined reduction in kinase activity corresponds to a confirmed reduction in the amount or activity of the biological agent under the same treatment conditions.

In this context, the kinase may be any one of, and/or have any of the properties of, the kinases described in this specification. Preferably, the kinase is formulated as an indicator according to the first aspect of the invention.

The sample generally is provided without any kinase present, so the method may comprise obtaining a sample believed to contain the biological agent and adding a defined amount of kinase. The agent may not be present at all (although preferably the sample is known to contain the biological agent). The point of the validation is that, after carrying out the treatment, it is confirmed that any agent that might have been present has been removed/inactivated to an acceptable degree.

Typically, an operator measures kinase activity prior to treating the sample and after treating the sample. It is also possible that contaminating, usually mesophilic, kinase can get into the sample prior to assaying for kinase activity. It is thus preferred that the kinase that is added to the sample is thermostable and that the assay step includes inactivating mesophilic kinase, such as by treating the sample at 70 degrees C. for at least 30 minutes, preferably 80 degrees C. for at least 10 minutes, prior to measuring residual kinase activity.

In preferred embodiments, the kinase, prior to the treatment, has an activity of at least 10,000,000 Relative Light Units (RLU) per mg kinase, or at least 8,000,000 RLU per mg kinase, or at least 5,000,000 RLU per mg kinase, or at least 3,000,000 per mg kinase, or at least 1,000,000 RLU per mg kinase, or at least 500,000 RLU per mg kinase, when measured in the presence of luciferin/luciferase by a luminometer.

In preferred embodiments of the invention, the predetermined kinase activity is less than 10,000 RLU per mg kinase, or less than 1000 RLU per mg kinase, or less than 500 RLU per mg kinase, or less than 250 RLU per mg kinase, or less than 100 RLU per mg kinase, or less than 10 RLU per mg kinase, or less than 1 RLU per mg kinase, or is 0 RLU per mg kinase.

In preferred embodiments of the invention, the predetermined reduction in kinase activity is equal to or greater than a 1 log reduction, or a 2 log reduction, or a 3 log reduction, or a 4 log reduction, or a 5 log reduction, or a 6-log reduction, or a 7 log reduction, or an 8 log reduction or a 9 log reduction in kinase activity.

In other embodiments, the predetermined reduction in kinase activity corresponds to at least a 6 log reduction, or a 7 log reduction, or an 8 log reduction, or a 9 log reduction, in the amount or concentration of the kinase. In further embodiments, the predetermined reduction in kinase activity corresponds to a reduction in RLU of at least 800,000, or at least 900,000, or at least 950,000, or at least 990,000, or at least 999,000, or at least 999,900, or at least 999,990, or at least 999,999 RLU.

In preferred embodiments of the invention, the confirmed reduction in the amount or activity of the biological agent within the sample is at least 6 logs, preferably at least 7 logs, more preferably at least 8 logs, most preferably at least 9 logs.

In particularly preferred embodiments, the treatment is continued until the residual kinase activity or the reduction in the kinase activity corresponds to a confirmed reduction in the amount or activity of the biological agent of at least 6 logs, or at least 7 logs, or at least 8 logs, or at least 9 logs.

In a fourth aspect of the invention, there is provided a method of correlating the reduction in the amount or activity of a biological agent in a sample with the kinase activity of an indicator according to the first aspect of the invention, comprising:
(i) preparing a sample containing a defined amount of the biological agent and a sample containing a defined amount of the kinase;
(ii) subjecting the sample(s) to a treatment;
(iii) measuring the residual activity of the kinase and optionally calculating the reduction in kinase activity;
(iv) measuring residual amount or activity of the biological agent and optionally calculating the reduction in the amount or activity of the biological agent;
(v) repeating steps (i) to (v), wherein at least one of the treatment parameters is changed.

In one embodiment, the biological agent and the kinase may be present in the same sample.

In a preferred embodiment, the treatment parameter comprises one or more of time, temperature, pH, pressure, protease concentration, and concentration of sterilant or detergent.

In a particular embodiment, the treatment comprises heating the sample(s) at 50-140° C., preferably 80-100° C., more preferably 134-138° C.; the treatment parameter is time; and steps (i) to (iv) are repeated by subjecting the sample(s) to said treatment for periods of 1, 5, 10, 20, 40 and 60 minutes.

In a further embodiment, the treatment comprises exposing the sample(s) to a pH of 9-14, preferably pH 12 or above, more preferably about pH12; the treatment parameter is time; and steps (i) to (iv) are repeated by subjecting the sample(s) to said treatment for periods of 1, 5, 10, 20, 40 and 60 minutes.

In another embodiment, the treatment comprises exposing the sample(s) to a protease at a concentration of 0.5-2 mg/ml, preferably about 1 mg/ml, more preferably about 2 mg/ml; the treatment parameter is time; and steps (i) to (iv) are repeated by subjecting the sample(s) to said treatment for periods of 1, 5, 10, 20, 40 and 60 minutes.

The above method enables preparation of calibration data for future use of the indicator for validation of a treatment on samples containing, or suspected of containing a biological agent. The calibration of a number of treatment processes is described in Examples 21-23.

In a fifth aspect of the invention, there is provided use of a kinase, as an indicator for validating a treatment process for reducing the amount or activity of a biological agent in a sample. In this context, the kinase may be any one of, and/or have any of the properties of, the kinases described in this specification. Preferably, the kinase is formulated as an indicator according to the first aspect of the invention.

The use of the indicator of the invention to monitor/validate a variety of processes is now described.

In one embodiment, the indicator is used to validate the performance of a biological washing preparation in a wash cycle (see Example 14). Whilst validation of a wash cycle would potentially be of use in a domestic setting, its most advantageous use would be within a healthcare, pharmaceutical or food preparation setting, e.g. for validating decontamination of bedclothes, gowns or other items associated with patients suffering or exposed to infectious agents (e.g. an outbreak of methicillin resistant *Staphylococcus aureus* (MRSA) or Norwalk/Norwalk-like virus). In this context, the indicator of the invention has the advantage that it is relevant to biological material such as blood or other bodily fluids.

For the validation of a wash cycle, the indicator is prepared by cross-linking a suitable kinase onto a flexible wand, strip of cloth or other material suitable for inclusion within the cycle. The indicator is put into the washer with the remainder of the load. Preferably, the indicator may be fixed within a suitable holder on the inside of the washer to facilitate its recovery.

The wash cycle is then performed and the indicator removed and assessed prior to any further handling or processing of the load, using a "reader" which has been calibrated to indicate an acceptable level of residual kinase activity within the indicator—the acceptable level having been derived from previous calibration and assessment of suitable wash performance within the process. Such assessment might include the overall levels of soiling and the viable count of micro-organisms as assessed using suitable model organisms known to those familiar with the art. Based on the calibrated read-out, the load is passed for further processing or the wash cycle is repeated.

In a second embodiment, the indicator is used to validate processes for the inactivation of viruses (see Example 15). The detection of live viral isolates in the environment is problematic, particularly when associated with an emergency situation where speed and accuracy may be critical. The present invention provides the possibility of developing indicator systems that allow the monitoring of decontamination procedures essentially in real time. This would be particularly valuable for surface decontamination in healthcare and related facilities following either an outbreak (e.g. of Norwalk-like viruses) or a deliberate release of a viral agent (such as small pox).

An indicator for validating a viral inactivation process can take a variety of different forms, e.g. a wand or dipstick for monitoring an area sprayed or immersed with virucide, or a suspended indicator for monitoring a gaseous phase decontamination process. Alternatively, the indicator kinase can be sprayed onto a surface prior to decontamination and the levels of residual kinase activity subsequently assessed by swabbing of the surface.

In a further embodiment of the invention, the indicator is used for validating protease degradation of bacterial protein toxins, plant toxins such as ricin, and other toxic proteins, peptides, or peptide analogues (see Example 16).

Proteases show significant potential for the degradation of a wide range of protein toxins that are potential biowarfare/bioterror threat agents including botulinum toxin, anthrax toxins and ricin. They also have the potential to inactivate a wide range of other potentially toxic or harmful protein or peptide agents to enable decontamination of surfaces/facilities or the safe disposal of materials. In this context, the indicator of the invention, together with the surface/material to be decontaminated, are subjected to the protease decontamination procedure. At the end of the procedure, the indicator is removed and the level of residual kinase activity assessed according to the method of the invention. The level of residual kinase activity is then correlated with inactivation indices for the particular protein toxin, or group of toxins. Assuming the level activity is equal to or below the defined index value then the material can be safely disposed of or the surface/facility returned to use.

Preferably a suitable safety margin is built into the calibration of the inactivation indices to allow for any variability of the process performance. The additional stability of the enzymes used in this invention allow for this to be done with more certainty and greater dynamic range than a wide range of other enzymatic indicators, including those from "thermostable" organisms such as *Bacillus stearothermophilus*, as shown by the data showing the relative thermal stability of AKs form thermophilic organisms (FIG. 1, Example 2).

The indicator may also be used to validate protease decontamination procedures for cleaning down pharmaceutical production apparatus. A wide variety of pharmaceutical products use materials from either humans, or animals that might be contaminated with a wide variety of agents including prion (TSE) agents and viruses (e.g. West Nile virus, hepatitis, HIV). The risks may be exacerbated when the source of the material is of animal origin (e.g foetal calf serum, horse immunoglobulins) and where an intermediate processing stage may carry the risk of increasing the concentration of unidentified pathogens in a particular sample. The possibility of using a protease to clean down manufacturing facilities and apparatus (e.g. chromatography columns, vessels, pipework) between manufacturing batches has the potential to reduce or eliminate such risks, even when the contaminant has not been formally identified. This is particularly true for prion agents in, for example, blood fractionation apparatus where there is a significant risk of accumulation and of carrying an infection risk into the final product.

For validating this type of procedure, the indicator of the invention is ideally designed as a dipstick to be immersed in the protease treatment solution, or as a cartridge to be attached in line with the apparatus to be cleaned. By assessing the levels of residual kinase activity in the indicator device following the treatment, and correlating this with the acceptable levels of cleaning, a rapid and reliable monitor of performance can be developed.

In another embodiment of the invention, the indicator is used for validating gas phase inactivation of biological agents, such as TSE (see Example 17).

The potential of ozone or other gas phase sterilants to inactivate such agents is suggested by a wide range of publications and articles, however, as yet, no method has explicitly been shown to be effective. To support the development and introduction of this gas phase technology into healthcare, a means of validating the performance of the technology will be required. As agents such as TSE have already been shown to be far more resistant to this form of inactivation than conventional viral or bacterial agents, the methods currently available for validating gas phase inactivation are unlikely to be suitable. The present invention addresses this problem.

For this type of validation, the indicator kinase is attached onto a solid support by any suitable method, e.g. general adsorption and chemical cross-linking via amide, peptide, carbonyl, or cysteine bonds. For example, for ozone sterilisation, a rigid polyvinyl chloride (PVC), glass, steel, polyamide or polypropylene support may be used, with the kinase coupled to the support by any one of the chemical methods previously described. The indicator is then included in the batch of material/instruments to be sterilised, exposed to the ozone, and assessed against a suitably calibrated inactivation index designed for assessing corresponding inactivation of the agent in question. Successful inactivation allows onward processing or use of the material/instruments.

The indicator may optionally be attached to the internal face of a tube or equivalent internal space, such that the penetration of the gas is restricted. This provides for a monitor that is suitable for assessing the penetration of the gas into equivalent spaces in instruments with lumens, or through packed loads of material. Alternatively, the kinase may be attached to porous materials such as polystyrene beads, or may be immobilised within a gel or resin.

In a further embodiment of the invention, the indicator is used for validating liquid chemical sterilisation systems (e.g. Endoclens) as used for processing of endoscopes and related equipment (see Example 18).

A wide range of endoscopes are routinely used in medicine and are an important part of medical diagnosis and treatment. These instruments are extremely sensitive and have posed a very significant problem for routine cleaning and disinfection. Traditionally, and remaining in current practice, endoscopes are cleaned by hand before being decontaminated using a low temperature method. A range of chemical disinfectants and automated re-processing apparatus has been developed to address the specific issues of decontaminating sensitive pieces of equipment such as endoscopes, where traditional autoclaving is not possible. These methods have helped to reduce the levels of contamination on difficult to clean instruments, which have been associated with the iatrogenic transmission of a wide range of viral and bacterial pathogens. The current method of validating such processes is to monitor the flow rate and temperature of the washing solution. The indicator of the invention provides for a further means of validation that provides a read-out of actual cleaning effectiveness within the endoscope lumen.

For this type of validation, the indicator is attached to the internal surface of a tube designed to be of a similar overall internal diameter to the endoscope tube. This indicator apparatus is connected in series to the endoscope on the automatic reprocessing apparatus. The endoscope is then processed in the normal way. At the end of the process, preferably before the endoscope is removed form the apparatus, the indicator is detached and assessed for the level of kinase activity remaining. The level of activity may be correlated with previously defined thresholds for the acceptable performance of the process and, based on this assessment, the endoscope may be transferred for additional cleaning or decontamination or prepared for use. If the level of performance is not adequate then the instrument may be re-processed (using the same or more stringent conditions) with a new indicator attached as previously. The indicator apparatus is also suitable for validating the manual cleaning of endoscope and/or any other instrument with a lumen.

In preparing indicators for the above validation, it is preferred that the kinase adheres to its support via non-specific protein adsorption methods based on the hydrophobicity of the enzyme. FIG. 5 demonstrates the ability of different recombinant kinases to adhere to polystyrene in this way. FIG. 5 also demonstrates that certain kinases have more desirable properties for this type of application, e.g. the *S. acidocaldarius* kinase is significantly more adherent to this type of surface when compared with kinases from *T. maritima* and *A. fulgidus*. This may be different for other types of surface, especially where the attachment to the surface may be via charged amino acid residues. In this type of indicator, the straightforward removal of the kinase from the surface is the determining feature in assessing cleaning performance, rather than any change or modification to the kinase. As such, this type of "adsorbent" indicator has a very wide range of uses in assessing washing performance. This is particularly important for validating the ability of the process to effectively remove bio-films from the lumen of devices such as endoscopes as this is thought to be one of the key factors affecting performance. As such, a suitable non-infectious biofilm may be used as a matrix for the kinase, preferably using serum, sucrose solution, aqueous gel or other means of simulating a biofilm to ensure that the process is effective against this form of contamination. Other types of indicator suitable for validating such processes are similar to those previously described, where the kinase is covalently attached to the support surface to generate chemical linkages such as disulfide, amide or carbonyl bonds. In these cases, the effects of the wash and/or sterilant are exerted by modifying the kinase so that it is no longer active. This would be particularly relevant for chemical sterilants that work by breaking peptide bonds, cross-linking proteins or related methods that perturb the structure of proteins.

In a further embodiment of the invention, the indicator is used to monitor routine cleaning performance in washer-disinfectors, such as those used in hospitals (see Example 19).

In another embodiment of the invention, the indicator is used for monitoring glutaraldehyde or ortho-phthaldehyde (OPA) treatments. Glutaraldehyde and formaldehyde have been widely used as sterilants over many years. The chemical disinfectants work by multiply crosslinking proteins in a non-specific fashion to destroy their function. Ortho-phthaldehyde (OPA) has emerged recently as a new disinfectant in this family and is being widely used as it avoids some of the toxicity problems associated with glutaraldehyde. The indicator of the invention is suitable for the monitoring of all of this class of chemical disinfectants as the kinases are sensitive to non-specific crosslinking of this kind. In this type of indicator, the kinase is covalently attached to a suitable surface and exposed to the chemical sterilant along with the other items to be sterilised. The effectiveness of the process is assessed by removing the indicator and measuring residual enzyme activity. This activity is compared to defined threshold values that indicate the correct performance of the process.

The use of different types of kinase may provide additional sensitivity or susceptibility to the process as may be required for different applications. The thermostable adenylate kinases described in this specification can be broadly classified into two groups based on their molecular architecture. Thus the enzymes from *Sulfolobus* species are examples of enzymes that have a trimeric structure with a central hydrophobic core that is the principle determinant in maintaining their activity at high temperatures. The second group of enzymes are monomeric, exemplified by the adenylate kinases from *Thermotoga* species, but have a slightly longer polypeptide chain with an additional "lid" domain that affects the active site. These different types of thermostable enzymes will show differential sensitivity to this type of chemical sterilant due to the variable flexibility of their peptide chains during enzyme action. For any particular sterilant and/or concentration an empirical screen will identify enzymes with suitable susceptibilities for monitoring and validating these types of chemicals.

In a further embodiment of the invention, the indicator is used as an ultra-rapid read-out monitor for ethylene oxide, hydrogen peroxide or other gas phase processes.

A wide range of gas phase sterilants are currently being used by a variety of manufacturers for routine disinfection of bacterial and viral agents. The current methods exploit the oxidative properties of the gases to destroy peptide linkages. As such, the kinases of the present invention, with their robust physicochemical properties, are ideal for providing a very rapid read-out of inactivation. The indicator in this example is similar to those described previously, e.g. in relation to the ozone inactivation of agents such as TSE.

A particularly challenging issue for sterilisation and decontamination processes is the ability to validate sterility of large bulk liquids, as might be required in the manufacture of various medicines or other pharmaceutical products. Whilst current methods monitor the temperature, time, and/or pressure parameters of a particular process (depending on its precise nature), there are few, if any, available methods for validating actual sterilisation within the bulk liquid. This is difficult even within volumes of around 1 litre, but is almost impossible at larger volumes.

The present invention provides a number of possible solutions to address this problem (see Example 20). In its simplest form, the kinase may be added to the liquid to be sterilised at a concentration suitable for measuring defined levels of kinase inactivation at the end of the process and equating this to levels of sterilisation. Whilst this might not be desirable in certain types of processes, the inert nature of the kinase and the ubiquitous presence of equivalent enzyme activities in all organisms, may make it acceptable. The acceptability may be improved by the fact that many thermostable enzymes are highly condensed and thus have very low immunogenicity following inoculation into animals.

Where such direct additions are not acceptable, the kinase may be added to the bulk liquid in a dialysis sack, porous container or immobilised to a suitable support such that no part of the enzyme is released into the bulk liquid, but the sterilising conditions work on the indicator in the same way as for the whole sample. A wide variety of possible ways of containing or immobilising proteins, to allow general diffusion of the liquid sample but to restrict the movement of the indicator sample, will be known to those familiar with the art. Possible examples include, but are not limited to dialysis membranes, Visking tubing, porous membranes, protein-binding resins, rigid gels or solid supports as described for the other indicators discussed. The indicator may be attached to the surface by any one of the methods discussed previously, or simply encased within a suitable membrane without attachment, such that the indicator may be simply removed from the bulk liquid at completion of the process.

DEFINITIONS SECTION

The term "biological agent" encompasses both infectious and non-infectious agents. Specific examples of biological agents relevant to the present invention include bacteria, viruses, spores, proteins, peptides and prions (both the infectious $PrP^{Sc}$ form and the non-infectious $PrP^c$ form) and also the specific agents mentioned in Examples 14-20. In preferred embodiments of the invention, the biological agent is a transmissible spongiform encephalopathy.

The term "treatment" or "treatment process" encompasses any process that is designed to reduce the amount or activity of a biological agent in a sample. Suitable treatments include one or more of: a selected pH, temperature or pressure, exposing the sample to a protease or other enzyme, exposing the sample to a detergent, a chemical sterilant or a gas-phase sterilant. In a preferred embodiment, the treatment is designed to reduce the infectious activity (also known as the infectivity) of an infectious biological agent, such as TSE. In particularly preferred embodiments, the treatment comprises exposing the sample to a protease at a temperature of between 50-120° C., preferably 60° C. or above, more preferably 100° C. or above, and/or exposing the sample to a pH of at least 9, preferably at a pH of at least 12. The term "treatment" also encompasses cleaning and inactivation processes such as high temperature autoclaving with wet or dry steam, ozone sterilisation, $H_2O_2$ sterilisation, rendering or other method designed to eliminate or inactivate the biological agent.

The term "sample" encompasses any item, instrument, surface, fluid or material. Examples include, but are not limited to, surgical and medical instruments, hospital gowns, bedclothes, bulk liquids, culled animal material, pharmaceuticals, workbenches, walls and floors.

The term "RLU" means Relative Light Unit. Those familiar with the art will recognise that Relative Light Units are a relative, not absolute, measurement. The figures given in the specification relate to measurements taken using a Berthold Orion 96-well microplate luminometer with injector system using a "flash" method of light measurement for 2 seconds immediately after the addition of the luciferase/luciferin reagents (technical specification photomultiplier measuring light emitted at a wavelength of 300-650 nm). To address this issue, manufacturers have generated data for RLU "factors", which allow the data generated by a given luminometer to be normalised to a calibrated standard. Thus, comparisons can be made between different instruments. The RLU factor for the Berthold Orion 96-well microplate luminometer used in the experiments described in the present specification is 1. Accordingly, the RLU values given in the specification can be regarded as standardised/normalised RLU values.

In terms of absolute values, an RLU value can be related to the concentration of ATP required to give said value with the reagents as described in the method (e.g. of Example 1). As an approximate conversion, and given the linear relationship between RLU values and ATP concentration, the following values can be used:

| RLU | Approximate concentration of ATP/$\mu$M |
|---|---|
| 12,000,000 | 1000 |
| 1,200,000 | 100 |
| 120,000 | 10 |
| 12,000 | 1 |
| 1,200 | 0.1 |
| 120 | 0.01 |

The invention is now described in specific embodiments in the following examples and with reference to the accompanying drawings in which:—

Figure 4:
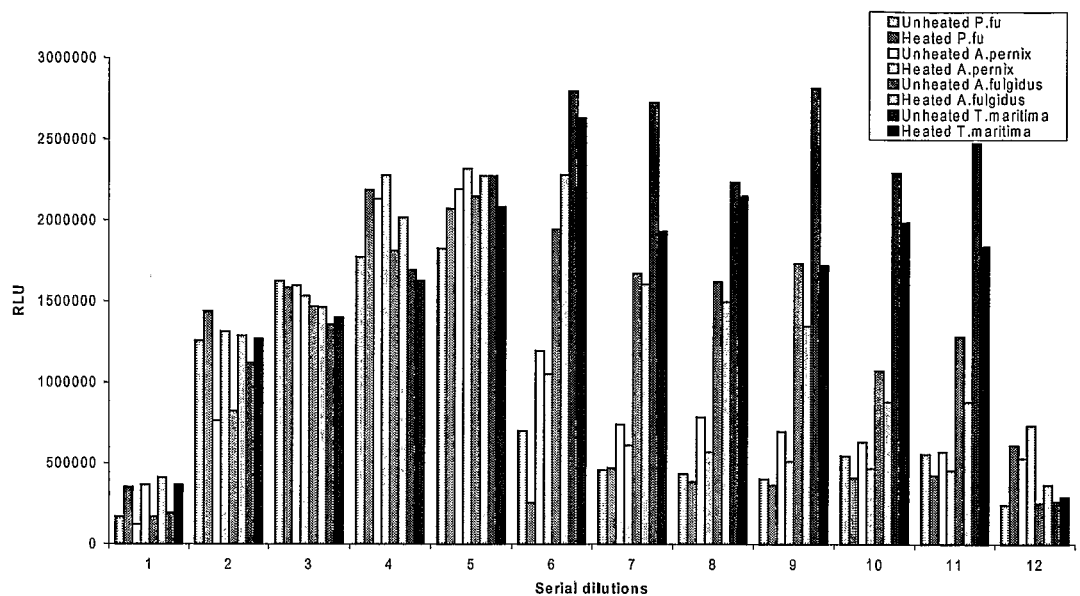
Figure 4:
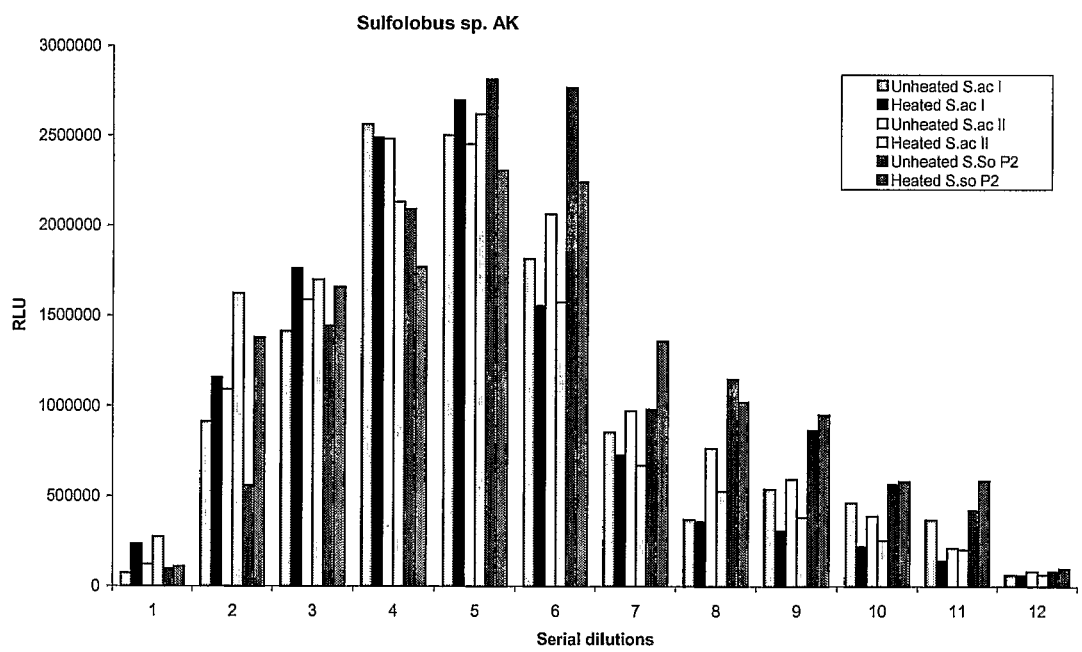

FIG. 4 shows the thermal stability of a range of AK enzymes recombinantly expressed in *E. coli*. Genes encoding AK enzymes were cloned and expressed as described in Example 4. All genes were expressed from the vector pET28a except for *S. acidocaldarius* clone I which was expressed from pET3a as described previously. Expression levels were similar for each clone but a proportion of the *Pyrococcus furiosus* (P.fu) enzyme was in the insoluble fraction and this is likely to have reduced the amount of this enzyme being assayed. The thermal stability of the recombinant enzymes was measured following incubation at 80° C. for 30 minutes in a crude *E. coli* lysate at 10-fold serial dilutions from 1 mg/ml total cellular protein (such that column 12 is equivalent to 1 fg/ml total protein). Enzymes from *Thermotoga maritima* and *Archaeoglobus fulgidus* showed significantly greater stability than the other enzymes tested, although the remaining enzymes (*Sulfolobus solfataricus* (S.so P2), *Aeropyrum pernix* and P.fu) showed similar activity to the *S. acidocaldarius* enzyme used as the basis of previous assays (data labelled as S.ac I).

Figure 5:
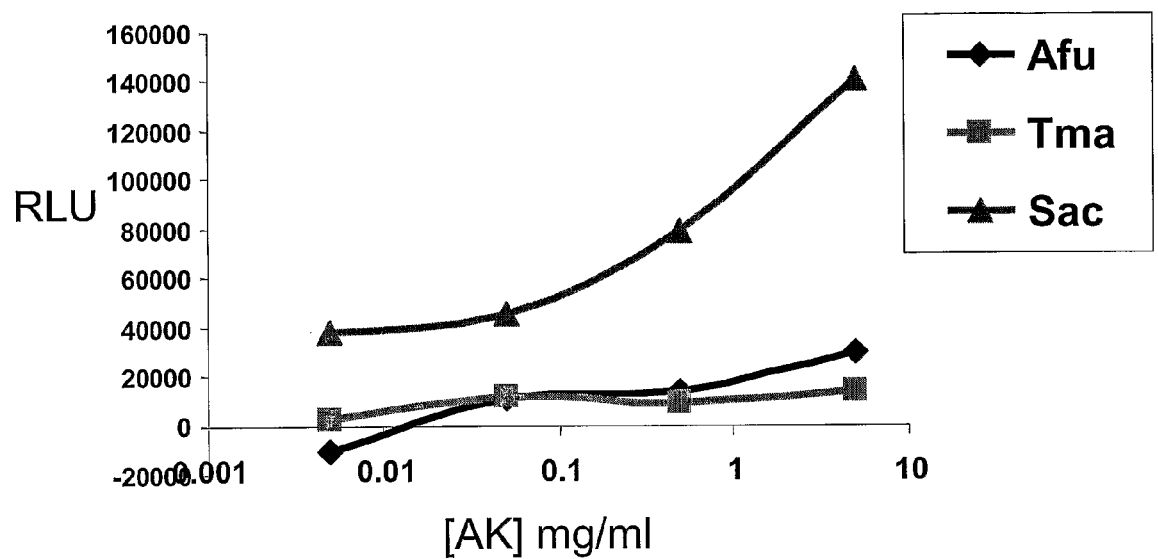

FIG. 5 shows the differential binding of thermostable adenylate kinases (tAK) to solid supports. To assess the relative binding of purified recombinant thermostable adenylate kinases to solid supports, demonstrating their potential use for direct absorbance type indicators, the binding of the enzyme to blocked plates was assessed. The surface of a standard polystyrene microtitre plate was blocked by the addition of 5% skimmed milk. The milk was removed and dilutions of tAKs from *Archaeoglobus fulgidus* (Afu), *Thermotoga maritima* (Tma) and *Sulfolobus acidocaldarius* (Sac) were applied to the plate. After washing, the amount of bound tAK was measured as described for the standard assay method (Example 1). The results demonstrate that the Sac tAK showed significantly higher binding to the blocked plate than either of the two alternative tAKs. Whilst the specific activity of the enzymes were not identical, both Afu and Tma tAKs showed higher activity than that from Sac, such that the real difference in binding is even more exaggerated than shown in the figure. As skimmed milk is a commonly used blocking agent for reducing protein binding to plates these results demonstrate that the Sac tAK has an extremely strong tendency for hydrophobic adsorption to the surface used in these experiments (polystyrene). This property of the enzyme, similar to that observed for the prion molecule to steel surfaces means that it is an extremely effective indicator for assessing a wide range of TSE inactivation and/or removal processes.

Figure 6:
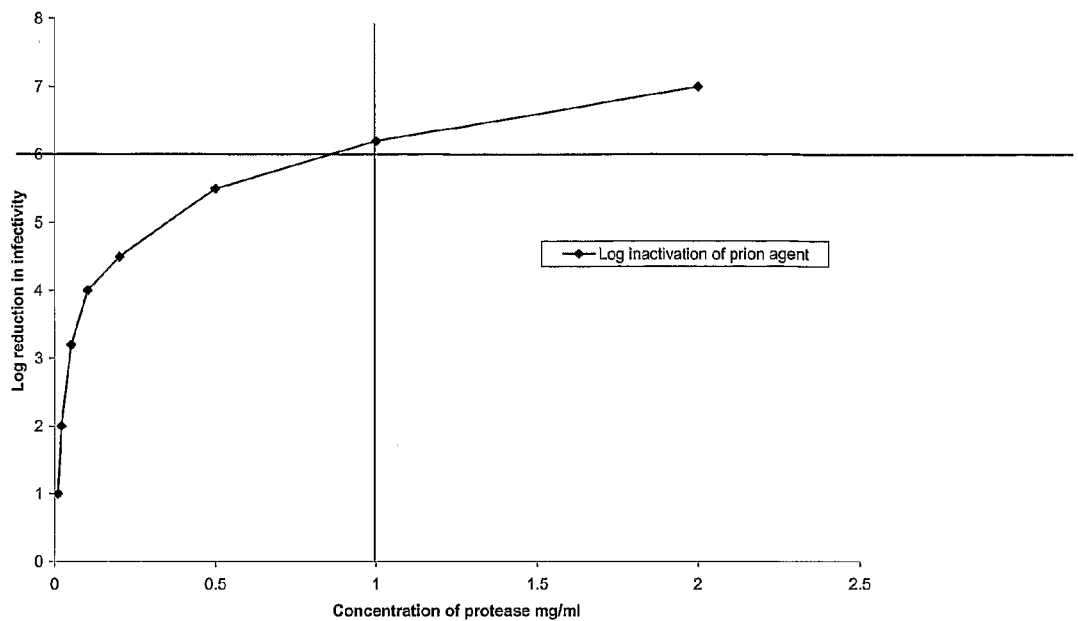
Figure 6:
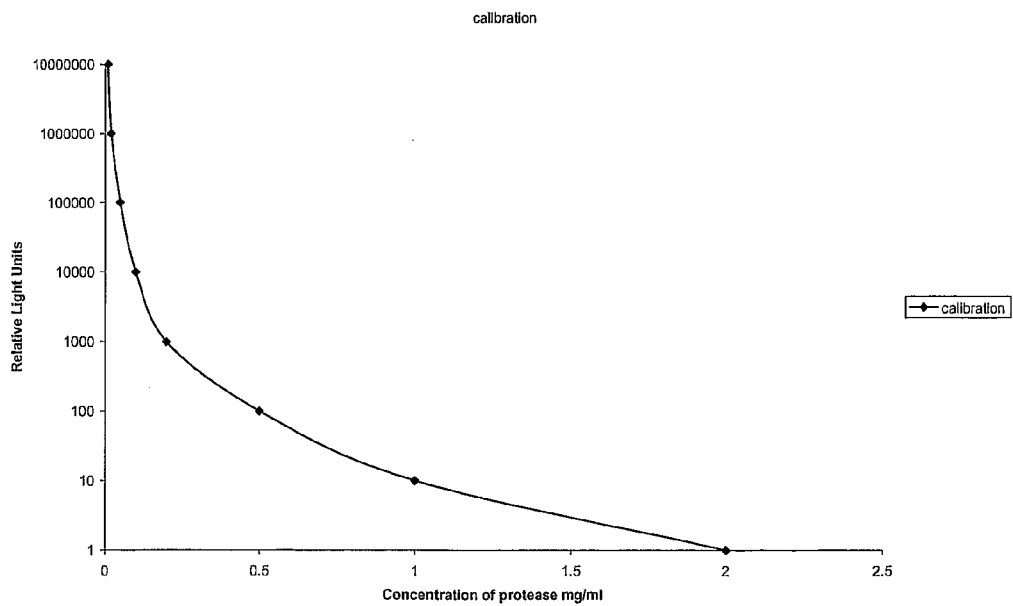

FIG. 6 shows the preparation of a calibration curve for a protease digestion treatment for inactivating prions.

Figure 7:
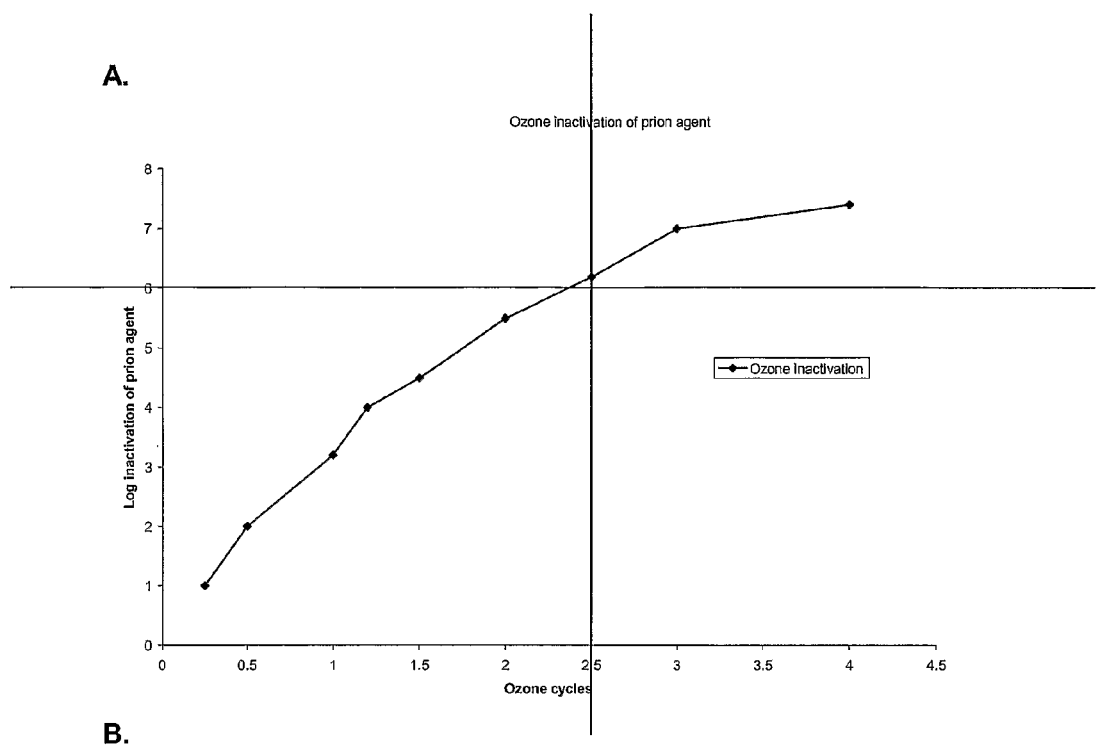
Figure 7:
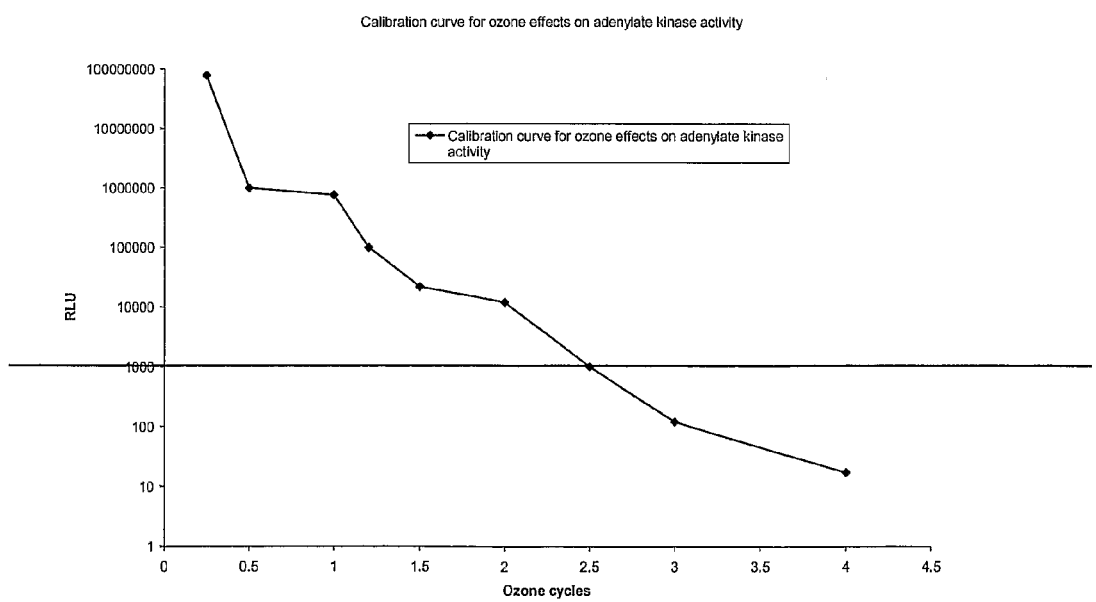

FIG. 7 shows the preparation of a calibration curve for a gas-phase ozone treatment for inactivating prions.

Figure 8:
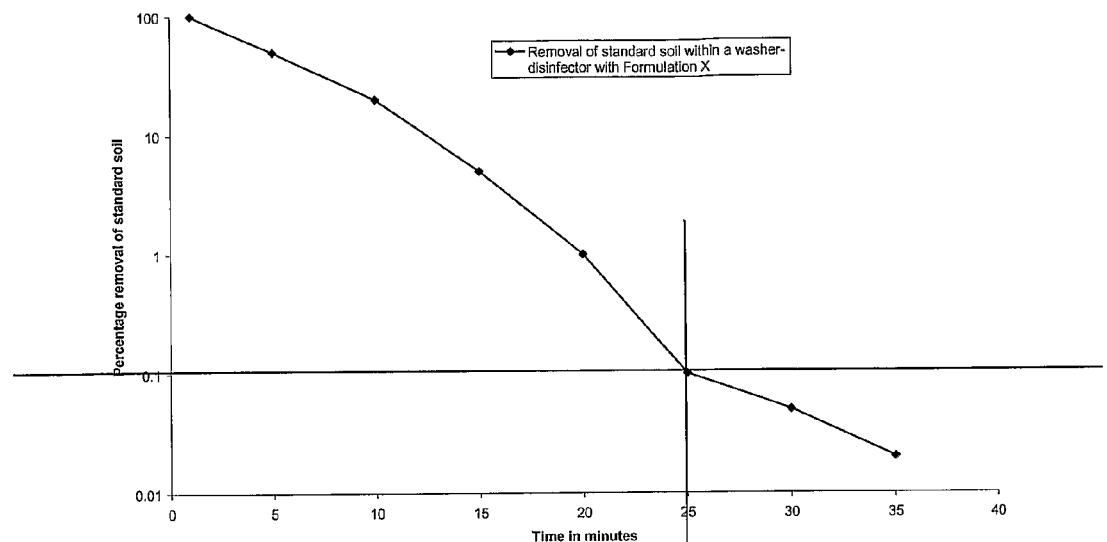
Figure 8:
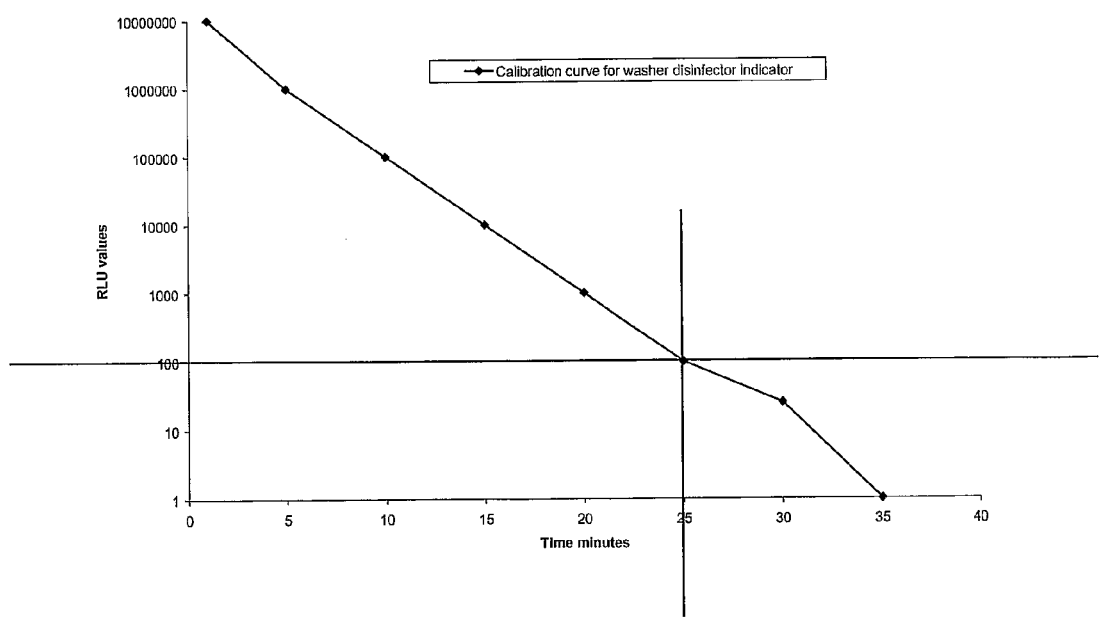

FIG. 8 shows the preparation of a calibration curve for a hospital washer-disinfector for removing standard soiling.

Figure 9:
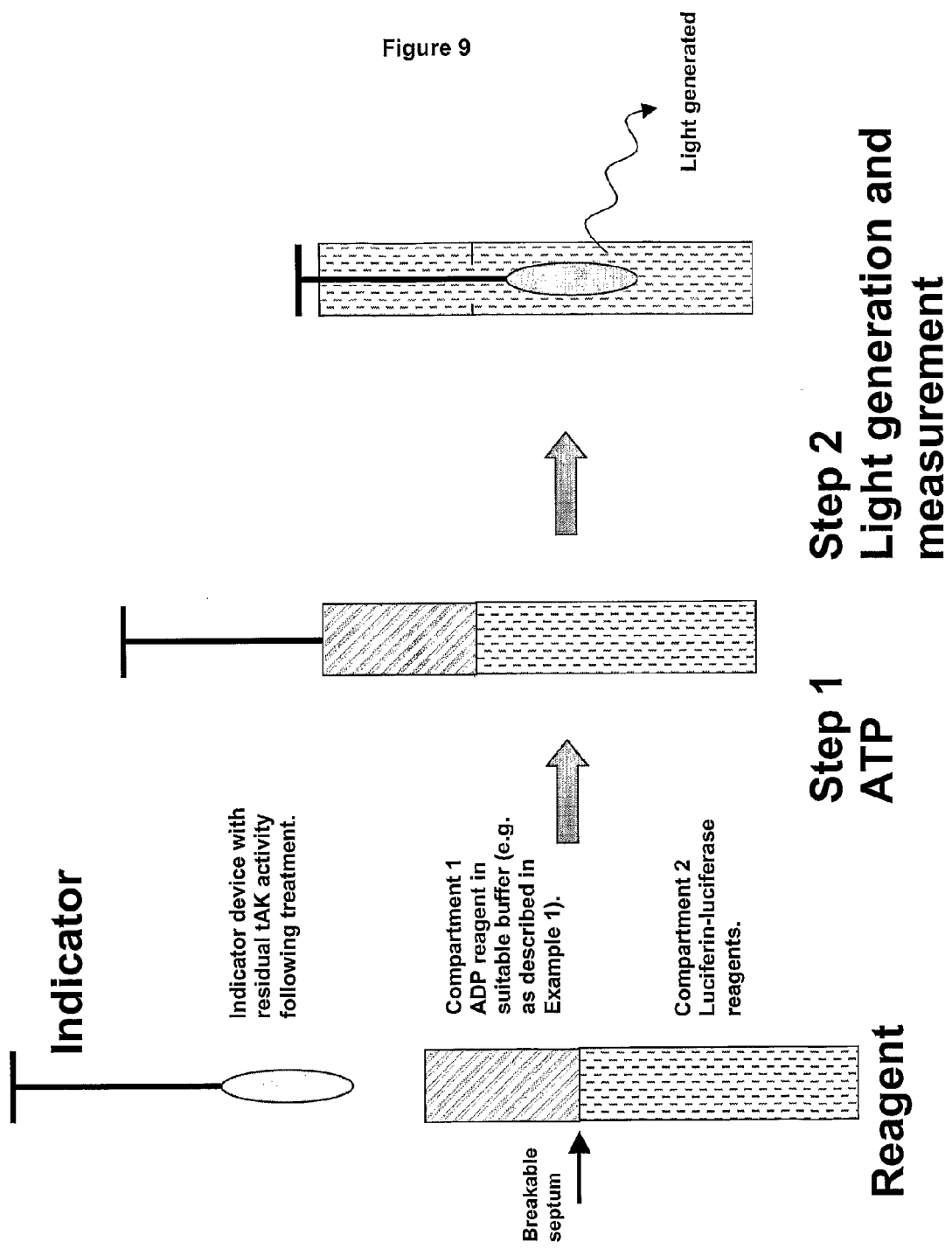

FIG. 9 shows the modification of a hand held hygiene monitor to allow rapid read-out assessment of tAK indicators.

| SEQ ID Nos | |
|---|---|
| SEQ ID 1 | Protein sequence of Adenylate kinase from *Sulfolobus solfataricus* |
| SEQ ID 2 | Protein sequence of Adenylate kinase from *Sulfolobus acidocaldarius* |
| SEQ ID 3 | Protein sequence of Adenylate kinase from *Sulfolobus tokodaii* |
| SEQ ID 4 | Protein sequence of Adenylate kinase from *Pyrococcus furiosus* |
| SEQ ID 5 | Protein sequence of Adenylate kinase from *Pyrococcus horikoshii* |
| SEQ ID 6 | Protein sequence of Adenylate kinase from *Pyrococcus abyssi* |
| SEQ ID 7 | Protein sequence of Adenylate kinase from *Methanococcus thermolithotrophicus* |
| SEQ ID 8 | Protein sequence of Adenylate kinase from *Methanococcus voltae* |
| SEQ ID 9 | Protein sequence of Adenylate kinase from *Methanococcus jannaschii* |
| SEQ ID 10 | Protein sequence of Adenylate kinase from *Methanopyrus kandleri* |
| SEQ ID 11 | Protein sequence of Adenylate kinase from *Methanotorris igneus* |
| SEQ ID 12 | Protein sequence of Adenylate kinase from *Pyrobaculum aerophilum* |
| SEQ ID 13 | Protein sequence of Adenylate kinase from *Thermotoga maritima* |
| SEQ ID 14 | Protein sequence of Adenylate kinase from *Aeropyrum pernix* |
| SEQ ID 15 | Protein sequence of Adenylate kinase from *Archaeoglobus fulgidus* |
| SEQ ID 16 | Protein sequence of Adenylate kinase from *Pyrococcus abyssi* (monomeric adenylate kinase (AdkE) |
| SEQ ID 17 | Protein sequence of Adenylate kinase from *Pyrococcus furiosus* genetically engineered to provide improved stability |
| SEQ ID 18 | Protein sequence of Adenylate Kinase from *Pyrococcus horikoshii* genetically engineered to provide improved stability |
| SEQ ID 19 | Protein sequence of Adenylate kinase from *Sulfolobus acidocaldarius* genetically engineered to provide improved stability |
| SEQ ID 20 | Protein sequence of Acetate kinase from *Thermatoga maritima* |
| SEQ ID 21 | Protein sequence of Pyruvate kinase from *Pyrococcus horikoshii* |
| SEQ ID 22 | Protein sequence of Pyruvate kinase from *Sulfolobus solfataricus* |
| SEQ ID 23 | Protein sequence of Pyruvate kinase from *Thermotoga maritima* |
| SEQ ID 24 | Protein sequence of Pyruvate kinase from *Pyrococcus furiosus* |
| SEQ ID 25 | Protein sequence of Acetate kinase from *Methanosarcina thermophila* |
| SEQ ID 26 | DNA sequence encoding the Adenylate kinase from *Sulfolobus acidocaldarius* |
| SEQ ID 27 | DNA sequence encoding the Adenylate kinase from *Sulfolobus acidocaldarius*, wherein codon usage has been optimised for expression of the gene in *E-coli*. |
| SEQ ID 28 | DNA sequence encoding the Adenylate kinase from *Thermotoga maritima* |
| SEQ ID 29 | DNA sequence encoding the Adenylate kinase from, *Thermotoga maritima*, wherein codon usage has been optimised for expression of the gene in *E-coli*. |
| SEQ ID 30 | DNA sequence encoding the Adenylate kinase from *Archaeoglobus fulgidus*, wherein codon usage has been optimised for expression of the gene in *E-coli*. |

EXAMPLE 1

Assay Protocol for *Sulfolobus acidocaldarius* AK 100 microlitres of a formulation of 1 mg/ml of adenylate kinase on a suitable solid support is the indicator and is subjected to the treatment process as required.

A heat inactivation step is optional. This involves heating the sample to a temperature permissive for the indicator AK but above that at which any mesophilic AKs are denatured. Typically this is by incubation at 80° C. for 10 minutes.

A washing step is optional and may be incorporated to remove any trace of materials used to perform the treatment if they are found to interfere with the assay.

The indicator is then added to a tube containing ADP substrate (e.g. reagents from Celsis, Biothema, Promega) at a concentration of 13.5 µM diluted in 15 mM MgAc, 1 mM EDTA buffer, pH 6.8 and incubated at 70° C. for 20 minutes.

The sample is cooled to room temperature and luciferin/luciferase substrate (ATP Reagent, Thermo Life Science) added. The assay is incubated for the required length of time and a luminometer is used to read the sample.

EXAMPLE 2

Purification of Native Adenylate Kinase Enzymes

Biomass was produced from twenty-four diverse thermophilic and hyperthermophilic microorganisms (Table 1).

Eight members of the archaea were represented along with sixteen diverse aerobic and anaerobic bacteria. AKs from each of these organisms was purified by affinity chromatography using selective absorption and desorption from Cibacron Blue 3A (Blue Sepharose). All enzymes were further characterised and purified by gel filtration (Superdex G200). This enabled identification of the major AK fraction and estimation of molecular mass.

EXAMPLE 3

Analysis of Thermostability of Native Adenylate Kinases

Figure 1:
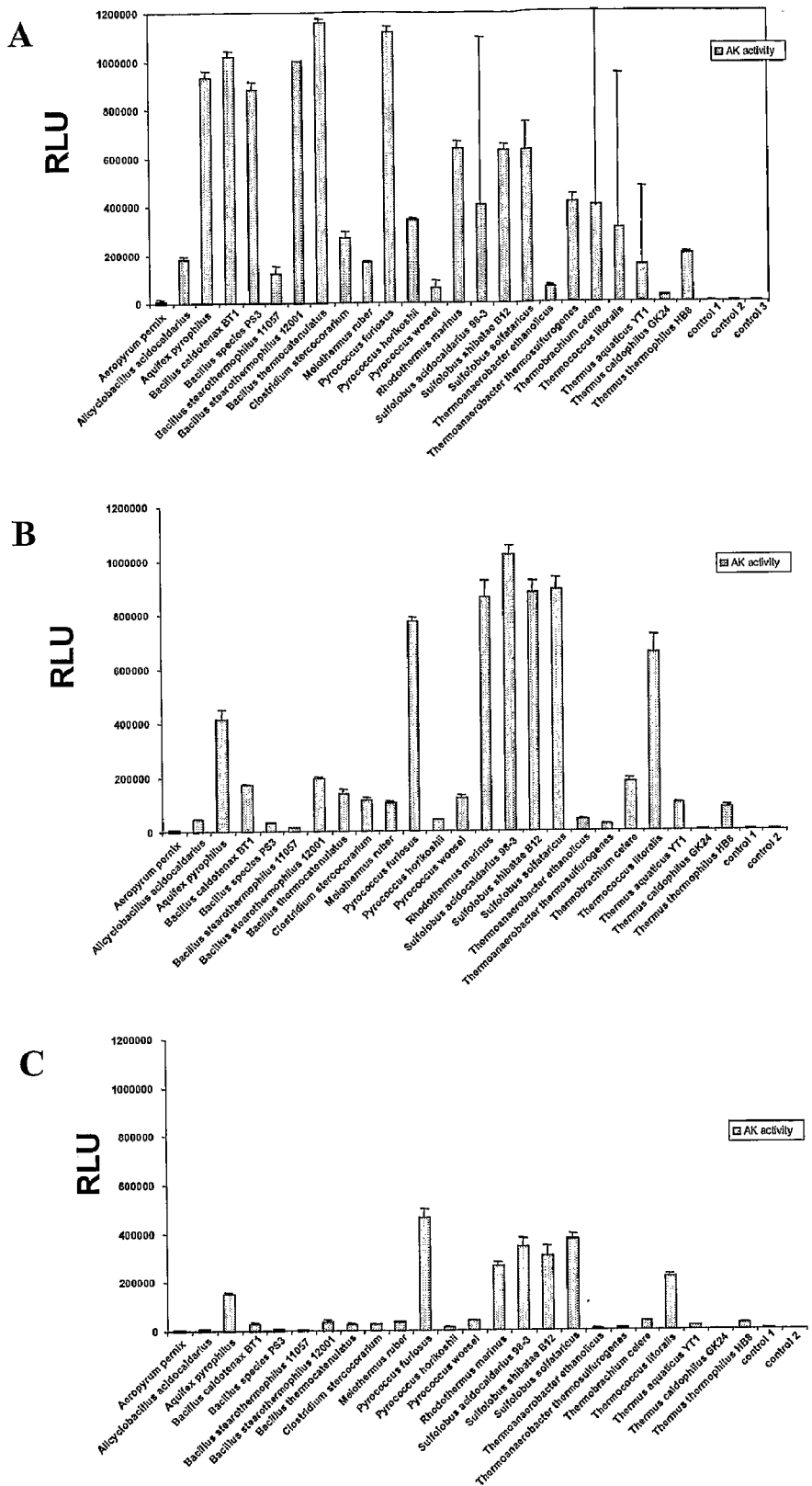
FIG. 1 shows activity of adenylate kinase (AK) enzymes after treatment at 70° C. (A), 80° C. (B) and 90° C. (C)
Figure 2:
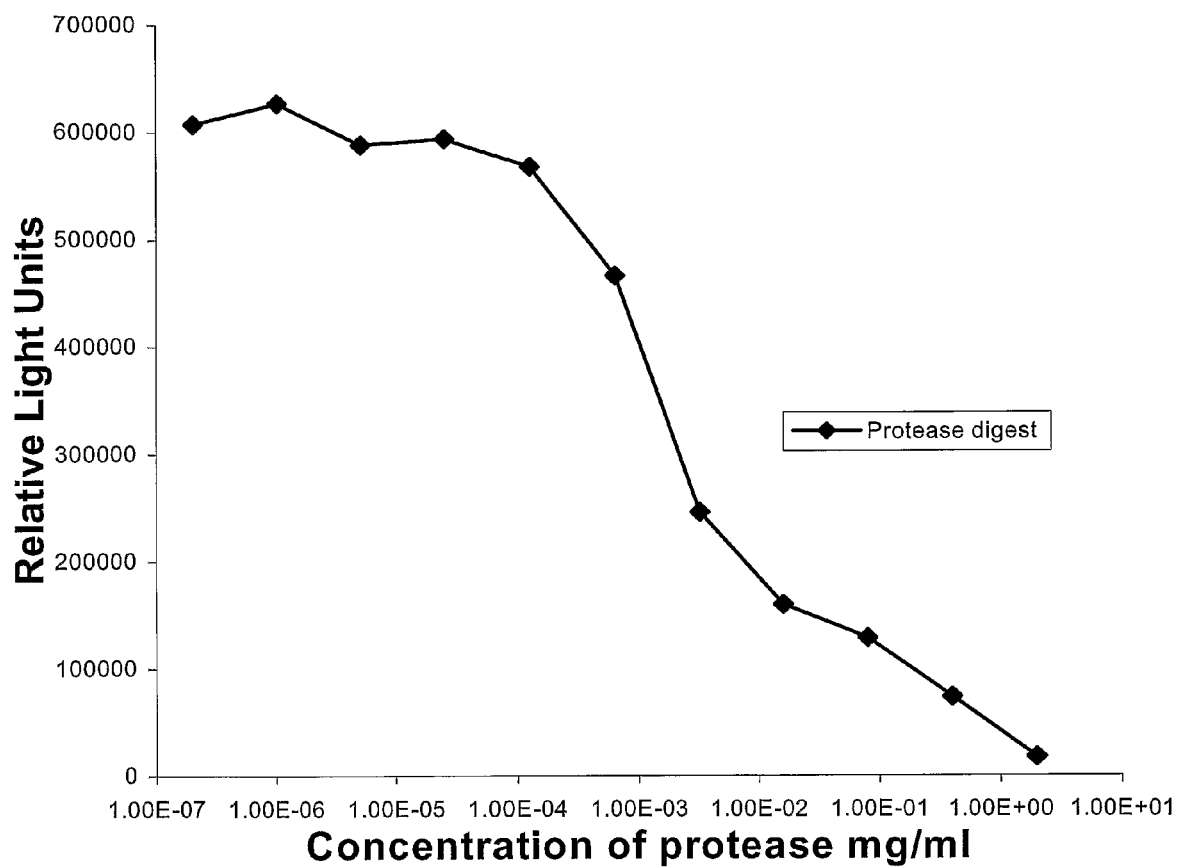
FIG. 2 shows residual enzyme activity after digestion of adenylate kinase (AK) with differing concentrations of alkaline protease.

The thermostability at 70, 80 and 90° C. of adenylate kinases isolated from biomass from thermophilic organisms was assessed, and the results shown in FIG. 1.

The adenylate kinases were isolated from the biomass by affinity chromatography using selective absorption and desorption from Cibacron Blue 3A (Blue Sepharose). The samples eluted from the columns were diluted 1:10 000 and then 10 µl of each added to a microtitre well. 2.5 µl of apyrase was added to each well to destroy the ATP present from the elution buffer, and incubated at 37° C. for 30 minutes. The apyrase was inactivated by heat treatment at 65° C. for 20 minutes.

ADP substrate was added and incubated at either 70 (panel A), 80 (panel B) or 90° C. (panel C) for 30 minutes and cooled to 25° C. before the addition of 10 µl of D-luciferin-luciferase reagent. The ATP produced was measured as RLU on a plate luminometer.

EXAMPLE 4

Expression and Purification of Recombinant Adenylate Kinases

Clones expressing representative thermostable AKs were secured and recombinant thermostable AKs from the *thermoacidophilic archaeon Sulfolobus acidocaldarius* and the thermophilic bacterium, *Bacillus stearothermophilus* produced. The plasmids were transformed into *E. coli* and the cell extracts shown to contain protein bands on electrophoresis corresponding to the expected molecular masses of the AKs. Thermostable AK activity was measured after incubation at the appropriate temperature (80° C. for the *Sulfolobus acidocaldarius* AK and 60° C. for the *Bacillus stearothermophilus* AK).

Purification methods for both thermostable AKs were established and included an initial heat treatment of incubation for 20 min at 80° C., to inactivate and aggregate proteins derived from *E. coli*, followed by affinity chromatography and gel filtration. The affinity chromatography involved adsorption of the enzyme to Blue Sepharose, followed by specific elution with a low concentration of AK co-factors (AMP+ATP and magnesium ions). The ATP and AMP (Sigma) in the elution buffer were degraded by incubation with mesophile apyrase, which is readily inactivated by subsequent heat treatment. Gel filtration chromatography was scaled up to utilise a preparation grade Superdex column to enable large quantities of both enzymes to be prepared.

Primers were designed for PCR amplification of the AK genes from the thermophilic organisms identified during the screening of candidate native enzymes.

The thermostable microorganisms were grown using individually defined growth conditions and genomic DNA isolated and used as templates for PCR amplification of the adenylate kinase genes from each organism. PCR amplified adenylate kinase genes from the thermophilic organisms, *Thermotoga maritima, Aeropyrum pernix, Sulfolobus acidocaldarius* and *Sulfolobus solfataricus* were sub-cloned into the vector, pET28a and transformed into a codon enhanced *E. coli* strain expressing rare tRNAs (Zdanovsky et al, 2000). This *E. coli* strain is suitable for enhancing expression levels of AT-rich genes.

The success of the transformation was assessed by a mini-expression study, and the results analysed by SDS-PAGE of the culture supernatants before and after induction with IPTG. SDS-PAGE was also used to analyse the supernatants after inclusion of a heat treatment step, which consisted of heating the sample to 80° C. for 20 minutes prior to running on the SDS-PAGE gel to remove heat labile proteins present in the sample.

Sequences:

```
Seq IDs
1 - Adenylate kinase from Sulfolobus solfataricus
MKIGIVTGIP GVGKTTVLSF ADKILTEKGI SHKIVNYGDY MLNTALKEGY

VKSRDEIRKL QIEKQRELQA LAARRIVEDL SLLGDEGIGL IDTHAVIRTP

AGYLPGLPRH VIEVLSPKVI FLLEADPKII LERQKRDSSR ARTDYSDTAV

INEVIQFARY SAMASAVLVG ASVKVVVNQE GDPSIAASEI INSLM

2 - Adenylate kinase from Sulfolobus acidocaldarius
MKIGIVTGIP GVGKSTVLAK VKEILDNQGI NNKIINYGDF MLATALKLGY

AKDRDEMRKL SVEKQKKLQI DAAKGIAEEA RAGGEGYLFI DTHAVIRTPS
```

```
GYLPGLPSYV ITEINPSVIF LLEADPKIIL SRQKRDTTRN RNDYSDESVI

LETINFARYA ATASAVLAGS TVKVIVNVEG DPSIAANEII RSMK

3 - Adenylate kinase from Sulfolobus tokodaii
MSKMKIGIVT GIPGVGKTTV LSKVKEILEE KKINNKIVNY GDYMLMTAMK

LGYVNNRDEM RKLPVEKQKQ LQIEAARGIA NEAKEGGDGL LFIDTHAVIR

TPSGYLPGLP KYVIEEINPR VIFLLEADPK VILDRQKRDT SRSRSDYSDE

RIISETINFA RYAAMASAVL VGATVKIVIN VEGDPAVAAN EIINSML

4 - Adenylate kinase from Pyrococcus furiosus
MPFVVIITGI PGVGKSTITR LALQRTKAKF RLINFGDLMF EEAVKAGLVK

HRDEMRKLPL KIQRELQMKA AKKITEMAKE HPILVDTHAT IKTPHGYMLG

LPYEVVKTLN PNFIVIIEAT PSEILGRRLR DLKRDRDVET EEQIQRHQDL

NRAAAIAYAM HSNALIKIIE NHEDKGLEEA VNELVKILDL AVNEYA

5 - Adenylate kinase from Pyrococcus horikoshii
MPFVVIITGI PGVGKSTITK LALQRTRAKF KLINFGDLMF EEALKLKLVK

HRDEMRKLPL EVQRELQMNA AKKIAEMAKN YPILLDTHAT IKTPHGYLLG

LPYEVIKILN PNFIVIIEAT PSEILGRRLR DLKRDRDVET EEQIQRHQDL

NRAAAITYAM HSNALIKIIE NHEDKGLEEA VNELVKILDL AVKEYA

6 - Adenylate kinase from Pyrococcus abyssi
MSFVVIITGI PGVGKSTITR LALQRTKAKF KLINFGDLMF EEAVKAGLVN

HRDEMRKLPL EIQRDLQMKV AKKISEMARQ QPILLDTHAT IKTPHGYLLG

LPYEVIKTLN PNFIVIIEAT PSEILGRRLR DLKRDRDVET EEQIQRHQDL

NRAAAIAYAM HSNALIKIIE NHEDKGLEEA VNELVEILDL AVKEYA

7 - Adenylate kinase from Methanococcus thermolithotrophicus
MKNKLVVVTG VPGVGGTTIT QKAMEKLSEE GINYKMVNFG

TVMFEVAQEE NLVEDRDQMR KLDPDTQKRI QKLAGRKIAE

MVKESPVVVD THSTIKTPKG YLPGLPVWVL NELNPDIIIV VETSGDEILI

RRLNDETRNR DLETTAGIEE HQIMNRAAAM TYGVLTGATV KIIQNKNNLL

DYAVEELISV LR

8 - Adenylate kinase from Methanococcus voltae
MKNKVVVVTG VPGVGSTTSS QLAMDNLRKE GVNYKMVSFG

SVMFEVAKEE NLVSDRDQMR KMDPETQKRI QKMAGRKIAE

MAKESPVAVD THSTVSTPKG YLPGLPSWVL NELNPDLIIV VETTGDEILM

RRMSDETRVR DLDTASTIEQ HQFMNRCAAM SYGVLTGATV

KIVQNRNGLL DQAVEELTNV LR

9 - Adenylate kinase from Methanococcus jannaschii
MMMMKNKVVV IVGVPGVGST TVTNKAIEEL KKEGIEYKIV NFGTVMFEIA

KEEGLVEHRD QLRKLPPEEQ KRIQKLAGKK IAEMAKEFNI VVDTHSTIKT

PKGYLPGLPA WVLEELNPDI IVLVEAENDE ILMRRLKDET RQRDFESTED

IGEHIFMNRC AAMTYAVLTG ATVKIIKNRD FLLDKAVQEL IEVLK

10 - Adenylate kinase from Methanopyrus kandleri
MGYVIVATGV PGVGATTVTT EAVKELEGYE HVNYGDVMLE IAKEEGLVEH

RDEIRKLPAE KQREIQRLAA RRIAKMAEEK EGIIVDTHCT IKTPAGYLPG

LPIWVLEELQ PDVIVLIEAD PDEIMMRRVK DSEERQRDYD RAHEIEEHQK

MNRMAAMAYA ALTGATVKII ENHDDRLEEA VREFVETVRS L
```

-continued

```
11 - Adenylate kinase from Methanotorris igneus
MKNKVVVVTG VPGVGGTTLT QKTIEKLKEE GIEYKMVNFG TVMFEVAKEE

GLVEDRDQMR KLDPDTQKRI QKLAGRKIAE MAKESNVIVD THSTVKTPKG

YLAGLPIWVL EELNPDIIVI VETSSDEILM RRLGDATRNR DIELTSDIDE

HQFMNRCAAM AYGVLTGATV KIIKNRDGLL DKAVEELISV LK

12 - Adenylate kinase from Pyrobaculum aerophilum
MKIVIVALPG SGKTTILNFV KQKLPDVKIV NYGDVMLEIA KKRFGIQHRD

EMRKKIPVDE YRKVQEEAAE YIASLTGDVI IDTHASIKIG GGYYPGLPDR

IISKLKPDVI LLLEYDPKVI LERRKKDPDR FRDLESEEEI EMHQQANRYY

AFAAANAGES TVHVLNFRGK PESRPFEHAE VAAEYIVNLI LRTRQKS

13 - Adenylate kinase from Thermotoga maritima
MMAYLVFLGP PGAGKGTYAK RIQEKTGIPH ISTGDIFRDI VKKENDELGK

KIKEIMEKGE LVPDELVNEV VKRRLSEKDC EKGFILDGYP RTVAQAEFLD

SFLESQNKQL TAAVLFDVPE DVVVQRLTSR RICPKCGRIY NMISLPPKED

ELCDDCKVKL VQRDDDKEET VRHRYKVYLE KTQPVIDYYG KKGILKRVDG

TIGIDNVVAE VLKIIGWSDK

14 - Adenylate kinase from Aeropyrum pernix
MKVRHPFKVV VVTGVPGVGK TTVIKELQGL AEKEGVKLHI VNFGSFMLDT

AVKLGLVEDR DKIRTLPLRR QLELQREAAK RIVAEASKAL GGDGVLIIDT

HALVKTVAGY WPGLPKHVLD ELKPDMIAVV EASPEEVAAR

QARDTTRYRV DIGGVEGVKR LMENARAASI ASAIQYASTV AIVENREGEA

AKAAEELLRL IKNL

15 - Adenylate kinase from Archaeoglobus fulgidus
MNLIFLGPPG AGKGTQAKRV SEKYGIPQIS TGDMLREAVA KGTELGKKAK

EYMDKGELVP DEVVIGIVKE RLQQPDCEKG FILDGFPRTL AQAEALDEML

KELNKKIDAV INVVVPEEEV VKRITYRRTC RNCGAVYHLI YAPPKEDNKC

DKCGGELYQR DDKEETVRE RYRVYKQNTE PLIDYYRKKG ILYDVDGTKD

IEGVWKEIEA ILEKIKS

16 - Monomeric adenylate kinase (AdkE) from Pyrococcus abyssi
MNILIFGPPG SGKSTQARRI TERYGLTYIA SGDIIRAEIK ARTPLGIEME

RYLSRGDLIP DTIVNTLIIS KLRRVRENFI MDGYPRTPEQ VITLENYLYD

HGIKLDVAID IYITKEESVR RISGRRICSK CGAVYHVEFN PPKVPGKCDI

CGGELIQRPD DRPEIVEKRY DIYSKNMEPI IKFYQKQGIY VRIDGHGSID

EVWERIRPLL DYIYNQENRR
```

EXAMPLE 5

Analysis of the Thermostability of Recombinant Adenylate Kinases

The thermal stability of recombinant tAK enzymes was assessed in crude *E. coli* cell lysates.

Cells were grown essentially as described in Example 4 and lysed by sonication. The AK activity of the crude extract was determined both before and after heat treatment at 80° C. for 30 minutes followed by 10-fold serial dilution The results (see FIG. 4) demonstrate that a wide variety of recombinant enzymes are suitable for the use in the method of the invention. Particularly preferred AKs are those from *T. maritima*, *A. fulgidus* and *S. solfataricus*. Such enzymes are likely to provide a greater dynamic range for the bioluminescent assay, if required, to provide still further sensitivity.

EXAMPLE 6

The Properties of Specific Thermostable Adenylate Kinases Demonstrate their Value as Indicators for TSE Inactivation The prion molecule shows a remarkably high propensity to stick to steel surfaces.

To develop an indicator for validation of prion decontamination procedures, a kinase having similar properties to the prion molecule would be advantageous. To explore this concept, the binding of different recombinant thermostable adenylate kinases to a given surface was assessed (see FIG. 5).

The binding of the kinases to previously blocked plates was assessed. The surface of a standard polystyrene microtitre plate was blocked by the addition of 5% skimmed milk. The milk was removed and dilutions of thermostable adenylate kinases from *Archaeoglobus fulgidus* (Afu), *Thermotoga maritime* (Tma) and *Sulfolobus acidocaldarius* (Sac) were applied to the plate. After washing, the amount of bound kinase was measured as described for the standard assay method (Example 1). The results demonstrate that the Sac kinase showed significantly higher binding to the blocked plate than either of the two alternative kinases. Whilst the specific activity of the enzymes was not identical, both Afu and Tma kinases showed higher activity than that from Sac, such that the real difference in binding is even more exaggerated than shown in the figure.

As skimmed milk is a commonly used blocking agent for reducing protein binding to plates, these results demonstrate that the Sac kinase has an extremely strong tendency for hydrophobic adsorption to the surface used in these experiments (polystyrene). This property of the enzyme, similar to that observed for the prion molecule to steel surfaces, means that it is an extremely effective indicator for assessing a wide range of TSE inactivation and/or removal processes. The Sac kinase binds in a very similar way to stainless steel, and shows a co-operativity of binding (i.e. there is a logarithmic (rather than linear) relationship between bound activity and amount of enzyme at low concentrations suggesting that it has aggregative properties on this surface similar to those seen for prion molecules).

This feature of the enzyme demonstrates its potential for direct absorbance type indicators where the kinase is adsorbed directly onto a suitable support rather than being covalently attached. The indicator in this case functions by assessing the ability of a process to remove the material from the surface and is widely applicable to monitoring washing and decontamination processes.

EXAMPLE 7

Genetic Modification of Adenylate Kinases to Improve Stability

Site-directed mutants were constructed in the AK gene from *P. furiosus*, *P. horikoshii* and *S. acidocaldarius* as shown in Examples 8-10 and SEQ IDs 17-19 respectively, using standard methods known to those familiar with the art.

In addition to specific changes identified in each gene, the regions underlined in the *S. acidocaldarius* sequence form the core packing region of the archaeal adenylate kinase trimer structure. Hence amino acid substitutions that disturb the packing of this region are likely to have a major effect in decreasing the thermal and physical stability of the enzyme. Conversely amino acid substitutions that improve the core packing, in particular hydrophobic residues with large side chains, may stabilise the enzyme to heat or other processes. Therefore in addition to the specific mutations already described a number of "selective" approaches were used with localised gene shuffling of related gene sequences in these regions (essentially as described in Stemmer (1994) Nature 370:389-391 and Crameri et al (1996) Nature Biotech. 14:315-319) and random PCR-based mutagenesis using degenerate oligonucleotides or modified nucleotide mixes (e.g. Vartanian et al (1996) Nucleic Acid Res. 24:2627-2633).

A number of these modifications show altered stability when assessed by recombinant expression in *E. coli* and rapid assay of adenylate kinase activity in lysed cells at high temperature.

EXAMPLE 8

Adenylate Kinases from *Pyrococcus furiosus* Genetically Engineered to Provide Improved Stability (SEQ ID NO. 17)

```
MPFVVIITGI PGVGKSTITR LALQRTKAKF RLINFGDLMF
EEAVKAGLVK HRDEMRKLPL (K TO E) IQRELQMKA AKKI
(T TO A) EMAKE HPILVDTHAT IKTPHGY (M TO L) LG
LPYEVVKTLN PNFIVIIEAT PSEILGRRLR DLKRDRDVET
EEQIQRHQDL NRAAAIAYAM HSNALIKIIE NHEDKGLEEA
VNELVKILDL AVNEYA
```

Mutations at one or more or all of the sites indicated modify the thermostability of the enzyme. In addition to the three defined changes highlighted, modification of the alanine at position 157 to another small hydrophobic residue (such as I, L) or larger hydrophobic residue (such as F) increases the thermostability of the recombinant protein. Hence, there are 35 variants possible through combination of modifications at these sites. Modification of amino acid 157 to a polar residue such as the T (as observed at the equivalent position in AdkA of *P. horikoshii*), S Y, D, E, K, R results in a decrease in stability.

EXAMPLE 9

Adenylate Kinases from *Pyrococcus horikoshii* Genetically Engineered to Provide Improved Stability (SEQ ID NO. 18)

The modification of either or both of the residues shown in bold and underlined increases the thermal stability of the enzyme (3 variants are possible).

```
MPFVVIITGI PGVGKSTITK LALQRTRAKF KLINFGDLMF
EEALKLGLVK HRDEMRKLPL EVQRELQMNA AKKIAEMAKN
YPILLDTHAT IKTPHGYLLG LPYEVIKILN PNFIVIIEAT
PSEILGRRLR DLKRDRDVET EEQIQRHQDL NRAAAIAYAM
HSNALIKIIE NHEDKGLEEA VNELVKILDL AVKEYA
```

EXAMPLE 10

Adenylate Kinase from *Sulfolobus acidocaldarius* Genetically Engineered to Provide Improved Stability (SEQ ID NO. 19)

The modification of the underlined residues shown can increase the thermal stability of the enzyme.

```
MKIGIVTGIP GVGKSTVLAK VKEILDNQGI NNKIINYGDF
MLATALKLGY AKDRDEMRKL SVEKQKKLQI DAAKGIAEEA
```

```
RAGGEGYLFI DTHAVIRTPS GY (A TO M) PGLPSYV

ITEINPSVIF LLEADPKIIL SRQKRDTTRN RNDYSDESVI

LETINFARYA ATASAVLAGS TVKVIVNVEG DPSIAANEII

RSMK
```

EXAMPLE 11

An Adenylate Kinase Indicator for the Validation of Inactivation of TSE

AK-based prion indicators were developed for use with protease inactivation of TSE material at elevated temperature and pH.

Indicator 1

A polycarbonate support was coated with a formulation of purified recombinant *S. acidocaldarius* AK (as described in Example 4). The enzyme was formulated at a concentration of 1 mg/ml in the presence of 5% (w/v) sorbitol, 10 mg/ml bovine serum albumen (Fraction V; Sigma chemical company) in phosphate buffered saline pH 7.4 (PBS). A volume of 100 μl was dried onto the support at 22° C. for 1 hour.

Indicator 2

A polystyrene support was coated with 100 microlitres of a formulation containing 1 mg/ml *S. acidocaldarius* AK, 1 mM tryptophan, 5% (w/v) sorbitol in Tris buffered saline (TBS) pH 7.4 and dried for 24 hours at 4 degrees C.

Indicator 3

A third indicator was prepared by cross-linking 100 microlitres of a 1 mg/ml formulation of a thermostable adenylate kinase from *S. solfataricus* onto a flexible polystyrene wand using a method based on disulfide bond formation. The recombinant thermostable adenylate kinase was derivitised with the heterobifunctional agent Sulfosuccinimidyl 6-(3'-[2-pyridyldithio]-propionamido)hexanoate (SPDP; Pierce chemical company, UK) at a ratio of between 1 and 3 SPDPs: protein. The derivatised kinase was then reduced by reaction with the reducing agent dithiothreitol (DTT), the reducing agent removed by dialysis, and the kinase reacted with a maleimide derivatised polystyrene wand.

Protease Treatment

An instrument wash bath was set up to operate at 60° C. and an alkaline protease formulation added to give between 1.5 and 2 mg/ml of enzyme buffered at pH 12 (as measured at the bath temperature). Suitable anionic detergents may also be included in the formulation if desired. The indicator was incubated for 30 minutes under the conditions described. The indicator was then removed and rinsed once with distilled water. The enzyme activity was then measured as described in Example 1 and luminescence measured using a luminometer.

Standard Curves for Adenylate Kinase Enzyme

Figure 3:
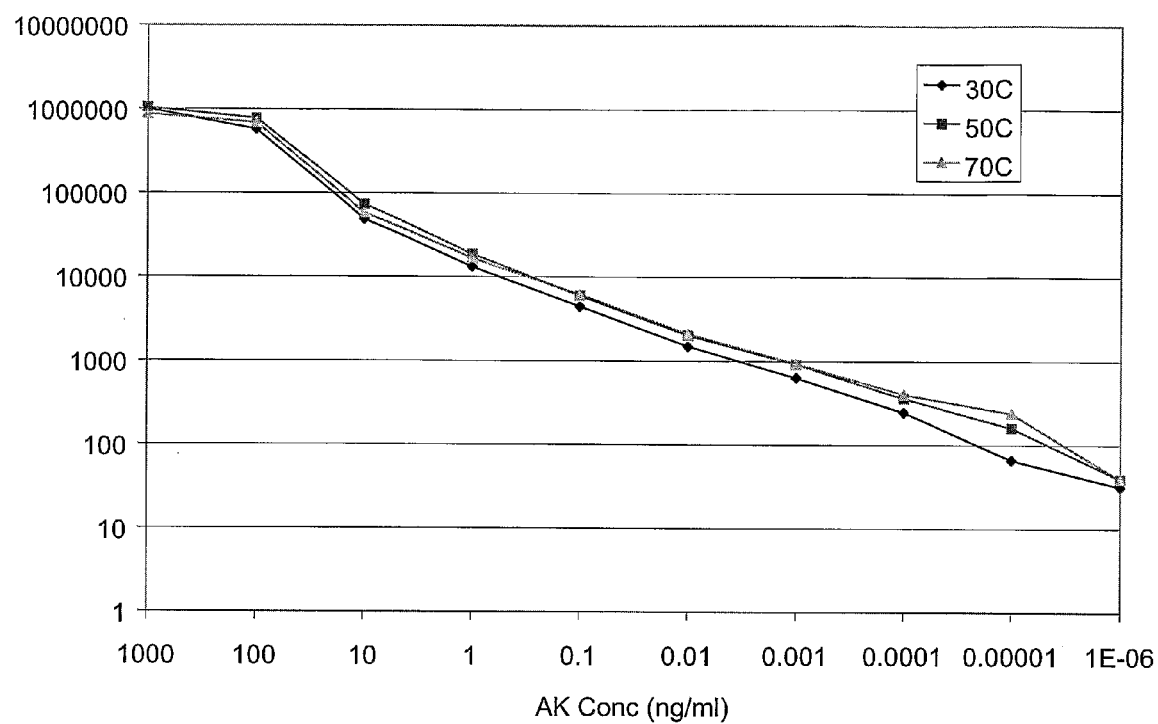
FIG. 3 shows standard curves correlating enzyme activity with residual concentration of adenylate kinase (AK).

Standard curves for the AK enzyme was prepared as follows. Serial dilutions of purified *Sulfolobus acidocaldarius* AK from 10 microgrammes/ml to 1 fg/ml were prepared in 50 mM Tris, 25 mM MESNA, pH 7.3. 100 microlitres of enzyme was added to each well of a microtitre plate and 100 microlitres of 135 micromolar ADP 15 mM MgAc, 1 mM EDTA added to each well. Three separate standard curves were prepared for incubation of the assay plate at 30 degrees C., 50 degrees C. and 70 degrees C. for 20 minutes. Following incubation 30 microlitres of luciferin/luciferase reagent (Biothema) was added and the signal read in a luminometer (Orion, Berthold) and the results shown in FIG. 3.

Validation of TSE Inactivation

The level of kinase activity was assessed against the standard curve for the kinase. For an indicator carrying 100 microgrammes of kinase with a luminescence value of greater than 1,000,000 Relative Light Units (RLU), as assessed from the standard curve, a luminescence value of less than 4000 RLU corresponds to a 6-log reduction in the concentration of kinase, and a luminescence value of less than 500 RLU corresponds to an 8-log reduction in the concentration of kinase.

Under the protease digestion conditions described above (2 mg/ml alkaline protease designated MC3 in a buffer formulation at pH12 and digestion for 30 minutes at 60 degrees C.) we demonstrated a reduction of approximately 8-logs in the levels of infectivity of the BSE-301V strain bioassayed in VM mice. Under the same conditions an AK indicator formulated as described above showed a reduction in RLU from in excess of 1,000,000 (untreated) to less than 500 RLU. Thus, an 8 log reduction in the concentration of kinase corresponds to an 8-log reduction in infectivity of BSE. Using this fact, it is possible to monitor kinase concentration and relate it to the reduction in levels of BSE infectivity.

Use of Validated Procedure

A set of surgical instruments used in routine surgery or routine neurosurgery for a patient not known to be incubating any form of CJD is returned to a hospital sterile services unit following use. The instruments are prepared for routine cleaning in a washer/disinfector set to operate at 60° C. for 30 minutes with a formulation of alkaline protease MC3. One or more AK indicators as described above are included in the processing bath. After treatment, and before instruments are sent on for normal autoclave sterilisation, the indicator is removed and a rapid assay carried out to confirm that the process is effective. An assay result that demonstrates a 6- or 8-log loss of activity, as defined by the parameters of the process, is required before any instruments can be processed further. Following a successful process, instruments may be prepared for other sterilisation procedures such as autoclaving as required.

EXAMPLE 12

Expression of Acetate and Pyruvate Kinases

Following the methods of Example 4, we expressed acetate and pyruvate kinases:—

```
20 - Acetate kinase from Thermatoga maritima
MRVLVINSGS SSIKYQLIEM EGEKVLCKGI AERIGIEGSR LVHRVGDEKH

VIERELPDHE EALKLILNTL VDEKLGVIKD LKEIDAVGHR VVHGGERFKE

SVLVDEEVLK AIEEVSPLAP LHNPANLMGI KAAMKLLPGV PNVAVFDTAF

HQTIPOKAYL YAIPYEYYEK YKIRRYGFHG TSHRYVSKRA AEILGKKLEE

LKIITCHIGN GASVAAVKYG KCVDTSMGFT PLEGLVMGTR SGDLDPAIPF
```

```
FIMEKEGISP QEMYDILNKK SGVYGLSKGF SSDMRDIEEA ALKGDEWCKL

VLEIYDYRIA KYIGAYAAAM NGVDAIVFTA GVGENSPITR EDVCSYLEFL

GVKLDKQKNE ETIRGKEGII STPDSRVKVL VVPTNEELMI ARDTKEIVEK IGR

21 - Pyruvate kinase from Pyrococcus horikoshii
MRRMKLPSHK TKIVATIGPA TNSKKMIKKL IEAGMNVARI NFSHGTFEEH

AKIIEMVREQ SQKLDRRVAI LADLPGLKIR VGEIKGGYVE LERGEKVTLT

TKDIEGDETT IPVEYKDFPK LVSKGDVIYL SDGYIVLRVE DVKENEVEAV

VISGGKLFSR KGINIPKAYL PVEAITPRDI EIMKFAIEHG VDAIGLSFVG

NVYDVLKAKS FLERNGAGDT FVIAKIERPD AVRNFNEILN AADGIMIARG

DLGVEMPIEQ LPILQKRLIR KANMEGKPVI TATQMLVSMT MEKVPTRAEV

TDVANAILDG TDAVMLSEET AVGKFPIEAV EMMARIAKVT EEYRESFGIT

RMREFLEGTK RGTIKEAITR SIIDAICTIG IKFILTPTKT GRTARLISRF

KPKQWILAFS TREKVCNNLM FSYGVYPFCM EEGFNENDIV RLIKGLGLVG

SDDIVLMTEG KPIEKTVGTN SIKIFQIA

22 - Pyruvate kinase from Sulfolobus solfataricus
MRKTKIVATL GPSSEEKVKE LAEYVDVFRI NFAHGDETSH RKYFDLIRTY

APESSIIVDL PGPKLRLGEL KEPIEVKKGD KIVFSQKDGI PVDDELFYSA

VKENSDILIA DGTIRVRVKS KAKDRVEGTV IEGGILLSRK GINIPNVNLK

SGITDNDLKL LKRALDLGAD YIGLSFVISE NDVKKVKEFV GDEAWVIAKI

EKSEALKNLT NIVNESDGIM VARGDLGVET GLENLPLIQR RIVRTSRVFG

KPVILATQVL TSMINSPIPT RAEIIDISNS IMQGVDSIML SDETAIGNYP

VESVRTLHNI ISNVEKSVKH RPIGPLNSES DAIALAAVNA SKVSKADVIV

VYSRSGNSIL RVSRLRPERN IIGVSPDPRL AKKFKLCYGV IPISINKKMQ

SIDEIIDVSA KLMQEKIKDL KFKKIVIVGG DPKQEAGKTN FVIVKTLEQQ KK

23 - Pyruvate kinase from Thermotoga maritima
MRSTKIVCTV GPRTDSYEMI EKMIDLGVNV FRINTSHGDW NEQEOKILKI

KDLREKKKKP VAILIDLAGP KIRTGYLEKE FVELKEGQIF TLTTKEILGN

EHIVSVNLSS LPKDVKKGDT ILLSDGEIVL EVIETTDTEV KTVVKVGGKI

THRRGVNVPT ADLSVESITD RDREFIKLGT LHDVEFFALS FVRKPEDVLK

AKEEIRKHGK EIPVISKIET KKALERLEEI IKVSDGIMVA RGDLGVEIPI

EEVPIVQKEI IKLSKYYSKP VIVATQILES MIENPFPTRA EVTDIANAIF

DGADALLLTA ETAVGKHPLE AIKVLSKVAK EAEKKLEFFR TIEYDTSDIS

EAISHACWQL SESLNAKLII TPTISGSTAV RVSKYNVSQP IVALTPEEKT

YYRLSLVRKV IPVLAEKCSQ ELEFIEKGLK KVEEMGLAEK GDLVVLTSGV

PGKVGTTNTI RVLKVD

24 - Pyruvate kinase from Pyrococcus furiosus
MRRVKLPSHK TKIVATIGPA TNSRKMIKQL IKAGMNVARI NFSHGSFEEH

ARVIEIIREE AQKLDRRVAI LADLPGLKIR VGEIKGGYVE LKRGEKVILT

TKDVEGDETT IPVDYKGFPN LVSKGDIIYL NDGYIVLKVE NVRENEVEAV

VLSGGKLFSR KGVNIPKAYL PVEAITPKDF EIMKFAIEHG VDAIGLSFVG

SVYDVLKAKS FLEKNNAEDV FVIAKIERPD AVRNFDEILN AADGIMIARG

DLGVEMPIEQ LPILQKKLIR KANMEGKPVI TATQMLVSMT TEKVPTRAEV
```

```
TDVANAILDG TDAVMLSEET AIGKFPIETV EMMGKIAKVT EEYRESFGLS

RIREFMEIKK GTIKEAITRS IIDAICTIDI KFILTPTRTG RTARLISRFK

PKQWILAFST NERVCNNLMF SYGVYPFCLE EGFDENDIVR LIKGLGLVES

DDMVLMTEGK PIEKTVGTNS IKIFQIA

25 - Acetate kinase from Methanosarcina thermophila
MKVLVINAGS SSLKYQLIDM TNESALAVGL CERIGIDNSI ITQKKFDGKK

LEKLTDLPTH KDALEEVVKA LTDDEFGVIK DMGEINAVGH RVVHGGEKFT

TSALYDEGVE KAIKDCFELA PLHNPPNMMG ISACAEIMPG TPMVIVFDTA

FHQTMPPYAY MYALPYDLYE KHGVRKYGFH GTSHKYVAER

AALMLGKPAE ETKIITCHLG NGSSITAVEG GKSVETSMGF TPLEGLAMGT

RCGSIDPAIV PFLMEKEGLT TREIDTLMNK KSGVLGVSGL SNDFRDLDEA

ASKGNRKAEL ALEIFAYKVK KFIGEYSAVL NGADAVVFTA GIGENSASIR

KRILTGLDGI GIKIDDEKNK IRGQEIDIST PDAKVRVFVI PTNEELAIAR

ETKEIVETEV KLRSSIPV
```

EXAMPLE 13

Thermostable Adenylate Kinase as an Indicator for Proteolytic Inactivation of TSE Agent A 20 mg/ml stock of alkaline protease was diluted using a solution of 10 μg/ml recombinant *S. acidocaldarius* AK in buffered 0.2M KCl pH 12, to generate a range of protease concentrations from 2 mg/ml down to 0.001 μg/ml. A volume of 100 μl of material was added to a polystyrene thermocycler plate and incubated for 10 minutes at 60° C. to allow digestion of the AK by the alkaline protease. The solution was neutralised by addition of 10 μl of 10× Phosphate buffer pH 7. 100 μl/well of 135 μM ADP in 15 mM MgAc, 1 mM EDTA buffer was added. The wells were then incubated for 20 mins at 70° C. in a thermocycler. 30 μl/well of Luciferin/Luciferase (ATP) reagent (Biothema) was added and the wells read on the luminometer immediately. The results of the assay are shown in FIG. 2.

These results show the remarkable stability of the AK enzyme to digestion by alkaline protease under conditions identified as being useful for the decontamination of surgical instruments. To relate the reduction observed following digestion with alkaline protease to the levels of activity remaining after treatment a standard curve such as that shown in FIG. 3 is used. In turn this is related to the degree of reduction in the levels of infectivity using a titration curve of TSE. For use as an indicator, the assay is designed such that the standard curve for enzyme activity is clearly marked with a limit/threshold value that corresponds to an acceptable level of decontamination by the process.

EXAMPLE 14

Validation of the Performance of Cloth Washing Cycles Using Biological Detergents Preparation of Indicator 1

A first indicator is prepared by cross-linking a thermostable adenylate kinase from *S. solfataricus* onto a flexible polystyrene wand using a method based on disulfide bond formation. In this method, the thermostable adenylate kinase is derivitised with a heterobifunctional agent such as Sulfosuccinimidyl 6-(3'-[2-pyridyldithio]-propionamido)hexanoate (SPDP; Pierce chemical company, UK) at a ratio of between 1-3 SPDP:protein. The derivatised kinase is then reduced by reaction with a reducing agent such as dithiothreitol (DTT), or 2-mercaptoethanesulfonic acid (MESNA), the reducing agent removed by dialysis, and the kinase reacted with a maleimide-derivatised polystyrene surface. Typically, 0.1 mg of kinase is present on the indicator.

Preparation of Indicator 2

A second indicator is prepared by the non-specific adherence of a thermostable adenylate kinase from *S. acidocaldarius* onto a high-protein binding polystyrene strip. The kinase is prepared at a concentration of 0.5-2 mg/ml in a bicarbonate buffer (pH 9.6), optionally containing the stabilising agent sorbitol at between 0.1 and 2% w/v. The kinase in binding buffer is then incubated with the high protein-binding polystyrene strip for a period of 1-2 hours at 22° C. (or 4° C. overnight). The residual kinase is removed by washing in a phosphate buffered saline. Typically, 0.1 mg of kinase is present on the indicator.

Validation of Wash Cycles

The washer is loaded with the items to be washed, and the indicator is fixed within a suitable holder on the inside of a washer (to facilitate its recovery). The wash cycle is then performed. At completion of the cycle, the indicator is removed and the residual activity of the kinase is assessed using a "reader" that is based on the assay methods described in Example 1. This reader is calibrated to indicate an acceptable "threshold" level of residual kinase activity within the indicator. This "threshold" level is derived from previous calibration and assessment of suitable performance within the process.

If the reader indicates that the residual kinase activity is equal to or below this threshold level, then the load is cleared for further processing.

EXAMPLE 15

Validation of a Process for the Inactivation of Norwalk-Like Virus (Also Termed Norovirus, Norwalk Virus or Winter Vomiting Disease) on Hard Surfaces Using a Protease Formulation Preparation of the Indicator An indicator is prepared by immobilising 0.1 mg of a thermostable adenylate kinase from *S. acidocaldarius* on a thin polystyrene strip using the disulfide mediated cross-linking as described in Example 14.

Validation

The indicator strip is placed on the potentially contaminated surface. Both the surface and the indicator strip are then coated with a highly active alkaline protease, proteinase K, that has been formulated within a paste. (Formulating the proteinase K in a paste improves contact between the enzyme with the surface/indicator.) The paste is left on the surface/indicator for 1-2 hours.

At the end of the treatment, the indicator is removed and the level of residual kinase activity is assessed using the "reader" described in Example 14. If the residual kinase activity is equal to or below the "threshold" level of the reader, then the surface is cleared as safe for use.

EXAMPLE 16

Validation of the Protease Degradation of Ricin

Preparation of Indicator

An indicator is prepared by immobilising 0.1 mg of a thermostable acetate kinase from *Thermotoga maritima* onto a polycarbonate strip using the standard sulfhydryl-maleimide coupling method described in the text and in Example 14.

Validation

The indicator strip is either immersed in a protease solution along with the object to be decontaminated, as in Example 11, or is attached to the surface to be decontaminated, as in Example 15.

The object/surface is then treated with the protease solution for the required length of time. At the end of the treatment, the indicator is removed and the level of residual kinase activity is assessed using a "reader" as described in Example 14. If the residual kinase activity is equal to or below the "threshold" level of the reader, then the object/surface is cleared as safe for use.

EXAMPLE 17

Validation of the Gas Phase Ozone Inactivation of a TSE Agent

Preparation of Indicator 1

A first indicator is prepared by covalently cross-linking 0.1 mg of a thermostable adenylate kinase from *S. acidocaldarius* onto a rigid polyvinyl chloride (PVC) support using the SPDP-maleimide method as described in Example 14.

Preparation of Indicator 2

A second indicator is prepared by reacting the *S. acidocaldarius* adenylate kinase with Bis-[β-(4-Azidosalicylamido) ethyl]disulfide (BASED; Pierce chemicals) in the presence of an amine reactive PVC surface. This leads to rapid covalent attachment of the kinase to the surface via amide linkages.

Validation

The indicator and the TSE-contaminated article are exposed to the gas phase ozone inactivation process. At the end of the process, the indicator is removed and the residual level of kinase activity is assessed using a "reader" as described in Example 14. If the residual kinase activity is equal to or below the "threshold" level of the reader, then the article is cleared as safe for use.

EXAMPLE 18

Validation of Liquid Chemical Sterilisation Systems (e.g. Endoclens) for Cleaning Endoscopes Preparation of Indicator 1

An indicator is prepared by chemically cross-linking (using the SPDP-based method described in Example 14) 0.1 mg of a thermostable adenylate kinase from *A. fulgidus* to the internal surface of a tube of a similar overall internal diameter to the endoscope tube.

Preparation of Indicator 2

A second indicator is prepared without derivatisation of the adenylate kinase. The gene sequence of the adenylate kinase from *Pyrococcus furiosus* is modified such that the recombinant protein includes an additional cysteine at the amino terminus of the sequence as shown in SEQ ID 4. The recombinant protein is expressed and purified as described previously and is reduced with DTT to ensure that the sulfhydryl group is available. This can then be reacted directly with maleimide reactive plastic to generate the cross-linking required. The formulation of the cysteine-containing enzyme at around 1-2 mg/ml is similar to that required for the derivitised method described in Example 14.

Validation

The indicator apparatus is connected in series to the endoscope on the automatic reprocessing apparatus and the endoscope is then processed in the normal way. At the end of the process, the indicator is detached and assessed for the level of residual kinase activity using a "reader" as described in Example 14. If the residual kinase activity is equal to or below the "threshold" level of the reader, then the endoscope is cleared as safe for use.

EXAMPLE 19

Validation of Cleaning of Surgical Instruments in Hospital Washer-Disinfectors Preparation of Indicator 1

An indicator is prepared by non-covalently attaching 0.1 mg of a thermostable adenylate kinase from *S. acidocaldarius* to a stainless steel surface. In this example the protein is not covalently linked to the indicator device as the indicator is designed to measure the removal of surface soiling by the process. The kinase is formulated at between 1-2 mg/ml preferably in a bicarbonate buffer at around pH 9.6. The material is adsorbed onto the metal surface by incubation at room temperature for 1-2 hours. The metal surface may be modified to make it more hydrophobic if required (e.g. for high stringency washes additional attachment may be needed to ensure sufficient signal is retained on the indicator). Any unattached kinase is removed by washing the indicator under conditions that will not displace a significant proportion of the adhered indicator kinase.

Preparation of Indicator 2

A second indicator is prepared by adhering (using the methods described for Indicator 1) 0.1 mg of the adenylate kinase from *S. acidocaldarius* to a stainless steel surface as part of a formulation containing standard soils currently used for validating cleaning processes of this type. This enables the indicator technology to be correlated with methods acceptable to regulatory bodies as part of routine validation and maintenance of washer-disinfectors.

Validation

The indicator is included within the batch of surgical instruments to be processed, and the washer-disinfector cycle is run. At the end of the run, the indicator is removed and assessed for the level of residual kinase activity using a "reader" as described in Example 14. If the residual kinase activity is equal to or below the "threshold" level of the reader, then the instruments are cleared as safe for use.

EXAMPLE 20

Validation of Processes for Sterilising Bulk Liquids

Preparation of Indicator 1

A first indicator is prepared by covalently attaching 0.1 mg of pyruvate kinase from *Sulfolobus solfataricus* to a polystyrene strip.

Preparation of Indicator 2

A second indicator is prepared by attaching 0.1 mg of the thermostable adenylate kinase from *A. fulgidus* to the inner face of a semi-permeable membrane such as a dialysis tube. The *A. fulgidus* kinase contains a naturally occurring reactive cysteine residue (i.e. not disulfide-bonded within the native enzyme), which can be reacted with BMPH (Pierce). This generates a group capable of reacting with oxidised carbohydrates, as generated, for example, by the treatment of Visking tubing with a suitable oxidising agent. The enzyme is formulated as described in Example 14 and reacted with the oxidised membrane surface to generate a covalently linked indicator.

Validation

The indicator is then attached within the bulk liquid and the sterilisation process (such as autoclaving, the passage of oxidative gases or other chemical sterilisation) is carried out.

The indicator is removed from the bulk liquid on completion of the process, and the residual activity of the kinase is compared to a defined threshold as described in Example 14.

EXAMPLE 21

Calibration of Residual Adenylate Kinase Enzyme Activity Following Protease Digestion An illustration of a calibration curve for the assessment of suitable levels of inactivation of a prion agent is shown in FIG. 6.

The example shown is for the protease treatment of surgical instruments under conditions defined as pH 12, 30° C. for 30 minutes.

The protease concentration is defined by assessing the level of prion inactivation at different concentrations of protease under the conditions described (Panel A). In the illustration, the protease MC3 is capable of providing a level of inactivation equivalent to a 6-log reduction in infectious dose at a concentration of 1 mg/ml under the conditions defined. At an equivalent concentration of the protease, and under the same conditions, the residual activity of adenylate kinase left on a *S. acidocaldarius* indicator, prepared essentially as described in Example 11, is of the order of 10 RLU (Panel B). A value of less than 10 RLU is therefore required to allow a batch of instruments to be passed for re-use.

Optionally an additional safety margin is built in such that an RLU value of less than 1 is required, correlating to the level of residual adenylate kinase activity following treatment of the indicator with a concentration of protease that gives a 7-log reduction (1-log greater inactivation than the set standard) in prion infectivity.

EXAMPLE 22

Calibration of Residual Adenylate Kinase Enzyme Activity Following Ozone Treatment An illustration of a calibration curve for the assessment of suitable levels of inactivation of a prion agent by an ozone treatment method is shown in FIG. 7.

The example shown is for an ozone treatment that releases a fixed rate of ozone into the sterilisation chamber over a defined period. Levels of ozone are then calculated by increasing or decreasing the time, with a concomitant increase or decrease in ozone concentration.

In panel A, the levels of prion inactivation according to fractions or multiples of the standard cycle time are shown. 2.5 standard cycles therefore represents a 6-log inactivation of the prion. At an equivalent multiple of the ozone cycle the residual level of adenylate kinase left on an indicator, prepared essentially as described in Example 17, is of the order of 1000 RLU.

A value of less than 1000 RLU is therefore required to allow a batch of instruments to be passed for re-use. Optionally an additional safety margin is built in for the indicator such that an RLU value of less than 100 is required, corresponding to the level of residual adenylate kinase activity following treatment of the indicator with concentration of ozone that gives a 7-log reduction (1-log greater inactivation than the set standard) in prion infectivity.

EXAMPLE 23

Calibration for an Indicator Designed to Monitor Routine Cleaning of Surgical Instruments in Hospital Washer-Disinfectors FIG. 8 shows an illustration of a calibration curve for assessing routine washing of surgical instruments using either a biological (enzyme containing) or detergent based formulation.

The indicator device is prepared as described in Example 19.

Panel A shows the percentage removal of standard soil from a defined medical instrument by the washer disinfector run with a defined washer formulation. The times of the wash cycle are modified to identify the appropriate level of performance. Panel B shows the residual *S. acidocaldarius* kinase activity from an indicator device prepared as in Example 17 and washed under the same conditions as for the standardly soiled instrument.

The residual level of the soil is defined as 0.1% of the starting material within this test and this correlates with a wash time of 25 minutes. The RLU value for the indicator washed for 25 minutes is approximately 100 RLU. The indicator may therefore be used within a 30 minute wash cycle to provide an indication of acceptable "soil" removal at the 0.1% level with an RLU threshold of 100 or at a 0.05% level with an RLU cut-off of approximately 25.

EXAMPLE 24

Modification of a Hand Held Hygiene Monitor to Allow Rapid Read-Out Assessment of the Kinase Indicators Many assay formats are potentially available to assess the levels of kinase activity associated with the indicators of the invention. These include tube luminometers, microtitre plate luminometers and a variety of other formats.

One format that has particular utility for the assessment of kinase activity on the indicator of the invention is the handheld hygiene monitor. The current technology detects ATP, via a luciferin-luciferase enzyme system, either directly on a surface or by lysing bacteria or other cells removed from the surface.

Those familiar with the art will recognise that this system is amenable to adaptation for the detection of kinases on indicator devices as the system already contains the ability to produce and measure light in response to the presence of ATP. By changing the reagent formulation to add an ADP substrate for the kinase it is possible to rapidly measure the presence of the enzyme on the indicator.

In practice, the indicator is added to a batch of material and treated. The indicator is then removed and inserted into a reagent tube to allow the generation of ATP. The formulation of this reagent tube is essentially as described in the method for Example 1 with high purity ADP reagents. The tube is incubated for a defined length of time, as defined for the type of indicator and process being monitored. At the end of the incubation, the reagent sample containing the ATP generated by the presence of the residual tAK is released into a second compartment containing the luciferin-luciferase, and measurable light is generated.

This device differs from the standard hygiene monitor as the first ATP-generation step is not required for the detection of ATP. The simplest way of constructing such a device is to have a tube with 2 compartments separated by a breakable septum as illustrated in FIG. 9. The indicator inserted into the tube at the first position (step 1) allows ATP generation and at the end of the incubation is pushed, either automatically or by hand, to the position shown in step 2 where light generation takes place. A wide variety of alternative constructions of such a device are possible. Optionally, heat denaturation steps to remove endogenous kinase activity and/or apyrase treatments to remove endogenous ATP can be carried out. The ATP generation step can be carried out at an elevated temperature if required.

TABLE 1

|   | Organism | Domain | Growth | $T_{opt}$ | $pH_{opt}$ |
|---|---|---|---|---|---|
| 1 | *Aeropyrum pernix* | Archaeon | Aerobe | 95° C. | 7.0 |
| 2 | *Alicyclobacillus acidocaldarius* | Bacterium | Aerobe | 65° C. | 3.5 |
| 3 | *Aquifex pyrophilus* | Bacterium | Microaerophile eberophile | 85° C. | 6.5 |
| 4 | *Bacillus caldotenax* BT1 | Bacterium | Aerobe | 65° C. | 7.0 |
| 5 | *Bacillus* species PS3 | Bacterium | Aerobe | 65° C. | 7.0 |
| 6 | *Bacillus stearothermophilus* 11057 | Bacterium | Aerobe | 65° C. | 7.0 |
| 7 | *Bacillus stearothermophilus* 12001 | Bacterium | Aerobe | 65° C. | 7.0 |
| 8 | *Bacillus thermocatenulatus* | Bacterium | Aerobe | 65° C. | 7.0 |
| 9 | *Clostridium stercocorarium* | Bacterium | Anaerobe | 55° C. | 7.0 |
| 10 | *Meiothermus ruber* | Bacterium | Aerobe | 60° C. | 6.5 |
| 11 | *Pyrococcus furiosus* | Archaeon | Anaerobe | 95° C. | 7.5 |
| 12 | *Pyrococcus horikoshii* | Archaeon | Anaerobe | 95° C. | 7.0 |
| 13 | *Pyrococcus woesei* | Archaeon | Anaerobe | 95° C. | 7.0 |
| 14 | *Rhodothermus marinus* | Bacterium | Aerobe | 70° C. | 6.5 |
| 15 | *Sulfolobus acidocaldarius* 98-3 | Archaeon | Aerobe | 75° C. | 2.5 |
| 16 | *Sulfolobus shibatae* B21 | Archaeon | Aerobe | 75° C. | 2.5 |
| 17 | *Sulfolobus solfataricus* P2 | Archaeon | Aerobe | 75° C. | 2.5 |
| 18 | *Thermoanaerobacter ethanolicus* | Bacterium | Anaerobe | 65° C. | 6.0 |
| 19 | *Thermoanaerobacter thermosulfurogenes* | Bacterium | Anaerobe | 65° C. | 6.5 |
| 20 | *Thermobrachium celere* | Bacterium | Anaerobe | 60° C. | 7.0 |
| 21 | *Thermococcus litoralis* | Archaeon | Anaerobe | 85° C. | 6.5 |
| 22 | *Thermus aquaticus* YT1 | Bacterium | Aerobe | 70° C. | 8.0 |
| 23 | *Thermus caldophilus* GK24 | Bacterium | Aerobe | 70° C. | 8.0 |
| 24 | *Thermus thermophilus* HB8 | Bacterium | Aerobe | 70° C. | 8.0 |

List of thermophilic organisms cultured to produce biomass for isolation of thermostable AKs.

The invention claimed is:

1. A method for validating a treatment process for reducing the amount or activity of a contaminating biological agent in a sample, comprising:
   (i) exposing an indicator and the contaminating biological agent to the treatment process,
   wherein the indicator is a thermostable kinase,
   the contaminating biological agent comprises at least one member selected from the group consisting of bacteria, viruses, spores, proteins, peptides and prions, and
   the treatment process comprises an exposure to at least one member selected from the group consisting of pH, temperature, pressure, enzyme, detergent, chemical sterilant, gas-phase sterilant, and high-temperature autoclaving with steam;
   (ii) measuring residual kinase activity of the thermostable kinase after the treatment; and
   (iii) comparing said residual kinase activity of the thermostable kinase to the kinase activity of the thermostable kinase before the treatment;
   wherein a reduction in the kinase activity of the thermostable kinase after the treatment, as compared to the kinase activity of the thermostable kinase before the treatment, can be correlated with a reduction in the amount or activity of the contaminating biological agent.

2. The method of claim 1, wherein the thermostable kinase is immobilised as part of a solid support.

3. The method of claim 1, wherein the thermostable kinase comprises adenylate kinase, acetate kinase or pyruvate kinase.

4. The method of claim 2, wherein the solid support comprises an indicator strip, a dip stick or a bead.

5. The method of claim 1, wherein the contaminating biological agent comprises a transmissible spongiform encephalopathy.

6. The method of claim 1, wherein the thermostable kinase has an amino acid sequence selected from the group consisting of SEQ ID Nos:1-25.

7. The method of claim 1, wherein the thermostable kinase is encoded by a nucleic acid sequence selected from the group consisting of SEQ ID Nos:26-30.

8. A method for validating a treatment process, comprising:
   (i) obtaining a sample that may contain a contaminating biological agent, wherein the contaminating biological agent comprises at least one member selected from the group consisting of bacteria, viruses, spores, proteins, peptides and prions; and
   (ii) exposing a mixture comprising the sample and a defined amount of a thermostable kinase to the treatment process, wherein the treatment process comprises an exposure to at least one member selected from the group consisting of pH, temperature, pressure, enzyme, detergent, chemical sterilant, gas-phase sterilant, and high-temperature autoclaving with steam; wherein the treatment process reduces an amount or activity of the contaminating biological agent;
   (iii) measuring a residual kinase activity and optionally calculating a reduction in kinase activity; and
   (iv) comparing said residual kinase activity to a predetermined kinase activity, or comparing said reduction in kinase activity to a predetermined reduction in kinase activity, wherein the predetermined kinase activity or predetermined reduction in kinase activity corresponds to a confirmed reduction in the amount or activity of the contaminating biological agent under identical treatment process conditions.

9. The method of claim 8, wherein the infectious contaminating biological agent comprises a transmissible spongiform encephalopathy.

10. The method of claim 8, wherein the thermostable kinase comprises an adenylate kinase, an acetate kinase or a pyruvate kinase.

11. The method of claim 8, wherein the thermostable kinase has an amino acid sequence selected from the group consisting of SEQ ID Nos:1-25.

12. The method of claim 8, wherein the thermostable kinase is encoded by a nucleic acid sequence selected from the group consisting of SEQ ID Nos:26-30.

13. A method of correlating the reduction in the amount or activity of a contaminating biological agent in a sample with the thermostable kinase activity of a biological process indicator, comprising:

(i) preparing a first sample comprising a defined amount of the contaminating biological agent and a second sample containing a defined amount of a thermostable kinase;

(ii) subjecting the first and second samples to a treatment process comprising an exposure to at least one member selected from the group consisting of pH, temperature, pressure, enzyme, detergent, chemical sterilant, gas-phase sterilant, and high-temperature autoclaving with steam;

(iii) measuring the residual kinase activity of the thermostable kinase and optionally calculating the reduction in kinase activity;

(iv) measuring residual amount or activity of the contaminating biological agent and optionally calculating the reduction in the amount or activity of the contaminating biological agent; and (v) repeating steps (i) to (iv), wherein at least one parameter of the treatment process is changed;

wherein the contaminating biological agent comprises at least one member selected from the group consisting of bacteria, viruses, spores, proteins, peptides and prions.

14. The method of claim 13, wherein the contaminating biological agent comprises a transmissible spongiform encephalopathy.

15. A method for validating a treatment process for reducing the amount or activity of a contaminating biological agent in a sample, comprising:
(i) directly exposing an indicator and the contaminating biological agent to the treatment process,
wherein the indicator is a thermostable kinase,
the contaminating biological agent comprises at least one member selected from the group consisting of bacteria, viruses, spores, proteins, peptides and prions, and
the treatment process comprises an exposure to at least one member selected from the group consisting of pH, temperature, pressure, enzyme, detergent, chemical sterilant, gas-phase sterilant, and high-temperature autoclaving with steam;

(ii) measuring residual kinase activity of the thermostable kinase after the treatment; and (iii) comparing said residual kinase activity of the thermostable kinase to the kinase activity of the thermostable kinase before the treatment;

wherein a reduction in the kinase activity of the thermostable kinase after the treatment, as compared to the kinase activity of the thermostable kinase before the treatment, can be correlated with a reduction in the amount or activity of the contaminating biological agent.

16. A method for validating a treatment process, comprising:
(i) obtaining a sample that may contain a contaminating biological agent, wherein the contaminating biological agent comprises at least one member selected from the group consisting of bacteria, viruses, spores, proteins, peptides and prions; and
(ii) directly exposing a mixture comprising the sample and a defined amount of a thermostable kinase to the treatment process, wherein the treatment process comprises an exposure to at least one member selected from the group consisting of pH, temperature, pressure, enzyme, detergent, chemical sterilant, gas-phase sterilant, and high-temperature autoclaving with steam; wherein the treatment reduces an amount or activity of the contaminating biological agent;

(iii) measuring a residual kinase activity and optionally calculating a reduction in kinase activity; and (iv) comparing said residual kinase activity to a predetermined kinase activity, or comparing said reduction in kinase activity to a predetermined reduction in kinase activity, wherein the predetermined kinase activity or predetermined reduction in kinase activity corresponds to a confirmed reduction in the amount or activity of the contaminating biological agent under identical treatment process conditions.

17. A method of correlating the reduction in the amount or activity of a contaminating biological agent in a sample with thermostable kinase activity of a biological process indicator, comprising:
(i) preparing a first sample comprising a defined amount of the contaminating biological agent and a second sample containing a defined amount of the thermostable kinase;

(ii) subjecting the first and second samples to a treatment comprising direct exposure to at least one member selected from the group consisting of pH, temperature, pressure, enzyme, detergent, chemical sterilant, gas-phase sterilant, and high-temperature autoclaving with wet or dry steam;

(iii) measuring the residual kinase activity of the thermostable kinase and optionally calculating the reduction in kinase activity;

(iv) measuring residual amount or activity of the contaminating biological agent and optionally calculating the reduction in the amount or activity of the contaminating biological agent;

(v) repeating steps (i) to (iv), wherein at least one of the treatment parameters is changed; and wherein the contaminating biological agent comprises at least one member selected from the group consisting of bacteria, viruses, spores, proteins, peptides and prions.

18. The method of claim 15, wherein the contaminating biological agent comprises a transmissible spongiform encephalopathy.

19. The method of claim 15, wherein the thermostable kinase has an amino acid sequence selected from the group consisting of SEQ ID Nos:1-25.

20. The method of claim 15, wherein the thermostable kinase is encoded by a nucleic acid sequence selected from the group consisting of SEQ ID Nos:26-30.

21. The method of claim 16, wherein the contaminating biological agent comprises a transmissible spongiform encephalopathy.

22. The method of claim 16, wherein the thermostable kinase comprises an adenylate kinase, an acetate kinase or a pyruvate kinase.

23. The method of claim 17, wherein the contaminating biological agent comprises a transmissible spongiform encephalopathy.

* * * * *

UNITED STATES PATENT AND TRADEMARK OFFICE
CERTIFICATE OF CORRECTION

PATENT NO. : 8,389,208 B2
APPLICATION NO. : 10/599098
DATED : March 5, 2013
INVENTOR(S) : J. Mark Sutton et al.

Page 1 of 1

It is certified that error appears in the above-identified patent and that said Letters Patent is hereby corrected as shown below:

In the claims:

Col. 80, claim 9, line 52, please delete "infectious" before contaminating.
Col. 80, claim 13, line 66, please delete "the" before thermostable.

Signed and Sealed this
Fifth Day of August, 2014

Michelle K. Lee
*Deputy Director of the United States Patent and Trademark Office*

UNITED STATES PATENT AND TRADEMARK OFFICE
CERTIFICATE OF CORRECTION

PATENT NO.       : 8,389,208 B2
APPLICATION NO.  : 10/599098
DATED            : March 5, 2013
INVENTOR(S)      : Sutton et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1914 days.

Signed and Sealed this

First Day of September, 2015

Michelle K. Lee
*Director of the United States Patent and Trademark Office*